United States Patent
Fox et al.

(10) Patent No.: US 10,875,840 B2
(45) Date of Patent: Dec. 29, 2020

(54) METHODS FOR INDUCING BIOORTHOGONAL REACTIVITY

(71) Applicants: Joseph Fox, Landenberg, PA (US); Xinqiao Jia, Newark, DE (US); Will Trout, Wilmington, DE (US); Joel Rosenthal, Newark, DE (US); Han Zhang, Columbia, MD (US); Yinzhi Fang, Newark, DE (US); Colin Thorpe, Newark, DE (US); Shuang Liu, Newark, DE (US); Yixin Xie, Newark, DE (US)

(72) Inventors: Joseph Fox, Landenberg, PA (US); Xinqiao Jia, Newark, DE (US); Will Trout, Wilmington, DE (US); Joel Rosenthal, Newark, DE (US); Han Zhang, Columbia, MD (US); Yinzhi Fang, Newark, DE (US); Colin Thorpe, Newark, DE (US); Shuang Liu, Newark, DE (US); Yixin Xie, Newark, DE (US)

(73) Assignee: UNIVERSITY OF DELAWARE, Newark, DE (US)

( * ) Notice: Subject to any disclaimer, the term of this patent is extended or adjusted under 35 U.S.C. 154(b) by 0 days.

(21) Appl. No.: 16/062,423

(22) PCT Filed: Dec. 15, 2016

(86) PCT No.: PCT/US2016/066793
§ 371 (c)(1),
(2) Date: Jun. 14, 2018

(87) PCT Pub. No.: WO2017/106427
PCT Pub. Date: Jun. 22, 2017

(65) Prior Publication Data
US 2018/0362504 A1 Dec. 20, 2018

Related U.S. Application Data

(60) Provisional application No. 62/267,450, filed on Dec. 15, 2015.

(51) Int. Cl.
| | | |
|---|---|---|
| C07D 257/08 | (2006.01) |
| C07D 401/04 | (2006.01) |
| C07D 401/14 | (2006.01) |
| C07D 403/14 | (2006.01) |
| C07D 403/04 | (2006.01) |
| C12P 17/16 | (2006.01) |

(52) U.S. Cl.
CPC ........ C07D 401/14 (2013.01); C07D 257/08 (2013.01); C07D 401/04 (2013.01); C07D 403/04 (2013.01); C07D 403/14 (2013.01); C12P 17/165 (2013.01); C12Y 111/01007 (2013.01)

(58) Field of Classification Search
CPC .. C07D 257/08; C07D 401/14; C07D 401/04; C07D 403/14; C07D 403/04
USPC .......................................... 544/179; 514/183
See application file for complete search history.

(56) References Cited

U.S. PATENT DOCUMENTS

| | | | | |
|---|---|---|---|---|
| 4,237,127 A | * | 12/1980 | Parsons ................ | A01N 43/713 514/183 |
| 5,274,091 A | * | 12/1993 | Coburn ................ | C07D 231/12 544/179 |
| 8,236,949 B2 | * | 8/2012 | Fox ........................ | C07C 59/62 544/179 |
| 2004/0115647 A1 | | 6/2004 | Paterson et al. | |
| 2007/0026365 A1 | | 2/2007 | Friedrich et al. | |
| 2007/0038475 A1 | | 2/2007 | Schlessinger et al. | |
| 2008/0256006 A1 | | 10/2008 | Buscema et al. | |

(Continued)

FOREIGN PATENT DOCUMENTS

WO WO-2017106427 A1 * 6/2017 ..... C12Y 111/01007

OTHER PUBLICATIONS

C.L. Lim et al., 16 Bulletin of the Korean Chemical Society, 374-377 (1995) (Year: 1995).*
H. Zhang et al., 138 Journal of the American Chemical Society, 5978-5983 (Apr. 14, 2016) (Year: 2016).*
G-W Rao et al., 16 Bioorganic & Medicinal Chemistry Letters (2006) (Year: 2006).*
J. Ebner et al., Catalytic Oxidations with Oxygen: An Industrial Perspective, In: Active Oxygen in Chemistry. Structure Energetics and Reactivity in Chemistry Series (SEARCH Series), vol. 2. (1995) (Year: 1995).*

(Continued)

*Primary Examiner* — Venkataraman Balasubramanian
(74) *Attorney, Agent, or Firm* — Ratnerprestia

(57) ABSTRACT

A method for catalytically converting a dihydrotetrazine 1 into a tetrazine 2, wherein one R group on the dihydrotetrazine 1 is a substituted or unsubstituted aryl, heteroaryl, alkyl, alkenyl, alkynyl, carbonyl, or heteroatom-containing group, and the other R group is selected from the group consisting of H and substituted or unsubstituted aryl, heteroaryl, alkyl, alkenyl, alkynyl, carbonyl,- or heteroatom-containing groups; 1, 2 wherein the method comprises oxidizing dihydrotetrazine 1 in a reaction medium in the presence of a catalyst and a stoichiometric oxidant.

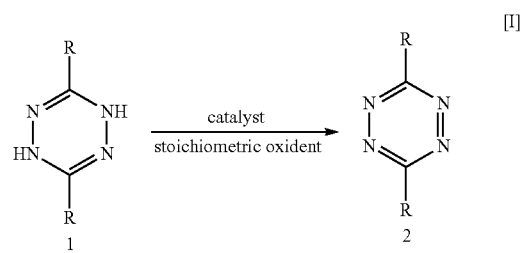

9 Claims, 9 Drawing Sheets

(56) References Cited

U.S. PATENT DOCUMENTS

2009/0023916 A1* 1/2009 Fox .................. C07C 59/62 540/450
2013/0052136 A1 2/2013 Chamney et al.

OTHER PUBLICATIONS

M.L. Blackman et al., 130 Journal of the American Chemical Society, 13518-13519 (2008) (Year: 2008).*
L.I. Robbins et al., 71 Journal of Organic Chemistry, 2480-2485 (2006) (Year: 2006).*
J. Kerth et al., 27 Propellants, Explosives, Pyrotechnics, 111-118 (2002) (Year: 2002).*
R.A. Bowie et al., Journal of the Chemical Society, Perkin Transactions 1, 2395-2399 (1972) (Year: 1972).*
G. Cocquet et al., 56 Tetrahedron, 2975-2984 (2000) (Year: 2000).*
X. Hu et al., 7 Nature Communications, 1-12 (2016) (Year: 2016).*
Chen et al., "Reactive Oxygen Species (ROS) Inducible DNA Cross-Linking Agents and Their Effect on Cancer Cells and Normal Lymphocytes", Journal of Medicinal Chemistry, 2014, vol. 57, pp. 4498-4510.
International Search Report and Written Opinion for International Application No. PCT/US2015/066793, dated Feb. 26, 2016—7 pages.
Lam et al., "Improving FRET Dynamic Range with Bright Green and Red Fluorescent Proteins", Nat. Methods, Oct. 2012, vol. 9, No. 10, pp. 1005-1012.
Selvaraj et al., "An Efficient and Mild Oxidant for the Synthesis of S-tetrazines", Tetrahedron Letters, 2014; vol. 55, No. 34, pp. 4795-4797.
Taylor et al., "Design and Synthesis of Highly Reactive Dienphiles for the Tetrazine-trans-Cyclooctene Ligation", J. Am. Chem. Soc., Jun. 29, 2011; vol. 133, No. 25, pp. 9646-9649.
Zhang et al., "Interfacial Bioorthogonal Cross-Linking", ACS Macro Lett., 2014, vol. 3, pp. 727-731.
International Preliminary Report on Patentability for International Application No. PCT/US2016/066793, dated Jun. 19, 2018, 6 pages.

\* cited by examiner

A *Interfacial polymerization* produces dihydrotetrazine containing fibers that can be activated for bioorthogonal chemistry

B

METHODS FOR INDUCING BIOORTHOGONAL REACTIVITY

CROSS REFERENCE TO RELATED APPLICATIONS

This application claims priority benefit of a national stage application under 35 U.S.C. 371 of International Application No. PCT/US2016/066793, titled "Methods For Inducing Bioorthogonal Reactivity," filed Dec. 15, 2016, which claims priority to U.S. Provisional Patent Application No. 62/267,450, filed Dec. 15, 2015, the entire contents of which are incorporated herein by reference for all purposes.

STATEMENT REGARDING FEDERALLY SPONSORED RESEARCH

This invention was made with government support under NSF Grant Nos. CHE-0840401 and CHE-1229234 awarded by National Science Foundation and NIH Grant Nos. P20GM104316, P30GM110758, S10RR026962 and S10OD016267 awarded by National Institutes of Health. The government has certain rights in the invention.

BACKGROUND OF THE INVENTION

Bioorthogonal chemistry has evolved into a field with broad-reaching applications in biology, medicine and materials science. Driving the field has been the vigorous development of unnatural transformations that proceed selectively in the presence of Nature's functional groups. Recently, bioorthogonal chemistry has been utilized in payload release strategies, with the aim of triggering diverse events including drug delivery, gene expression, and modulating materials properties. There has also been a growing interest in using external stimuli to induce bioorthogonal reactivity. In particular, photoinducible reactions have emerged as a method for turning on bioorthogonal reactions with temporal and spatial control. Key advances include tetrazole and cyclopropenone based ligations, where photolysis produces reactive nitrile imines and cyclooctyne derivatives, respectively. Such 'photoclick' reactions generally utilize short-wavelength light to unleash more reactive species. The direct use of red or near IR light to induce bioorthogonal reactivity has not been described. Lin has recently described two-photon based photoinducible tetrazole reactions that utilize near IR light, and Popik has shown that cyclopropenones can be photodecarbonylated by a two photon process. While two-photon methods provide high spatial resolution, their very small focal volumes currently limit many practical applications. Recently, near-IR photodecaging strategies have been described based on cyanine, BODIPY, and phthalocyanine dyes. A current challenge for red- and near-IR photodecaging strategies lies is the need to improve the kinetics of photorelease.

SUMMARY OF THE INVENTION

The invention provides a method for catalytically converting a dihydrotetrazine 1 into a tetrazine 2, wherein one R group on the dihydrotetrazine 1 is a substituted or unsubstituted aryl, heteroaryl, alkyl, alkenyl, alkynyl, carbonyl, or heteroatom-containing group, and the other R group is selected from the group consisting of H and substituted or unsubstituted aryl, heteroaryl, alkyl, alkenyl, alkynyl, carbonyl, or heteroatom-containing groups;

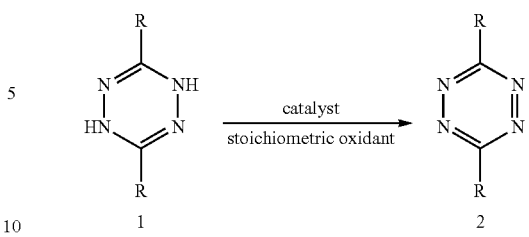

wherein the method comprises oxidizing dihydrotetrazine 1 in a reaction medium in the presence of a catalyst and a stoichiometric oxidant.

The invention also provides compounds according to the following structures, useful in performing the methods described herein or resulting from performing those method:

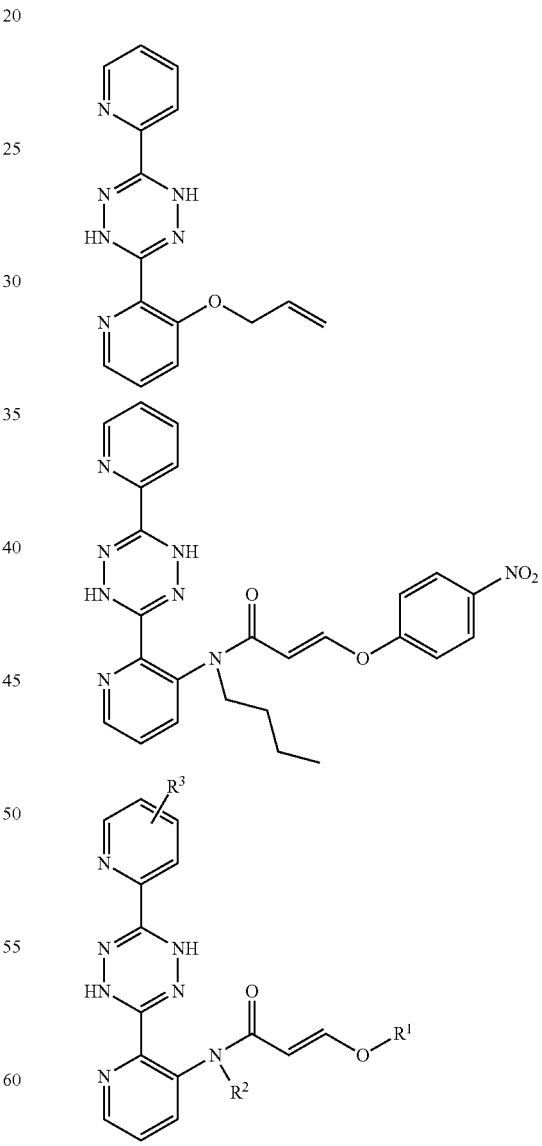

wherein $R^1$, $R^2$ and $R^3$ are each individually selected from the group consisting of H, aryl, heteroaryl, alkyl, alkenyl, alkynyl, carbonyl, and heteroatom-containing groups;

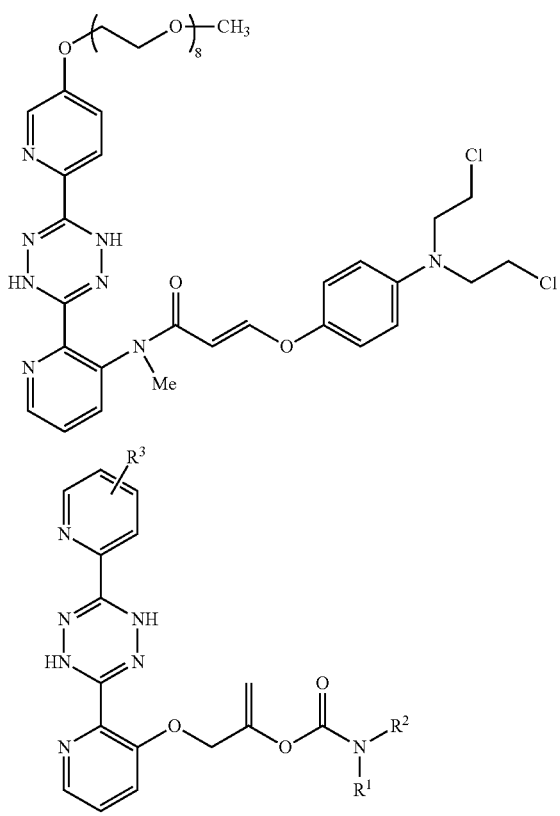

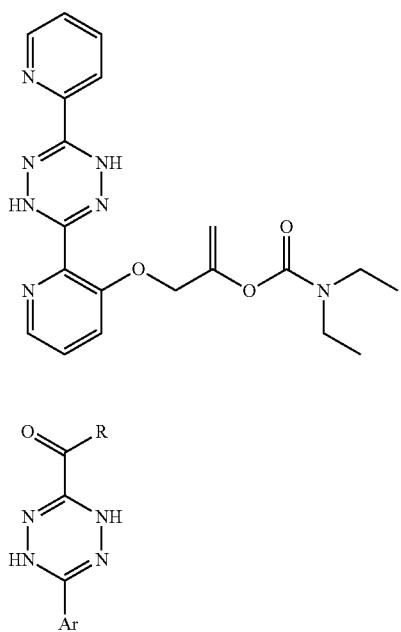

wherein $R^1$, $R^2$ and $R^3$ are each individually selected from the group consisting of H, aryl, heteroaryl, alkyl, alkenyl, alkynyl, carbonyl, and heteroatom-containing groups;

wherein R is selected from the group consisting of H, aryl, heteroaryl, alkyl, alkenyl, alkynyl, and heteroatom-containing groups, and Ar is an aromatic or heteroaromatic group

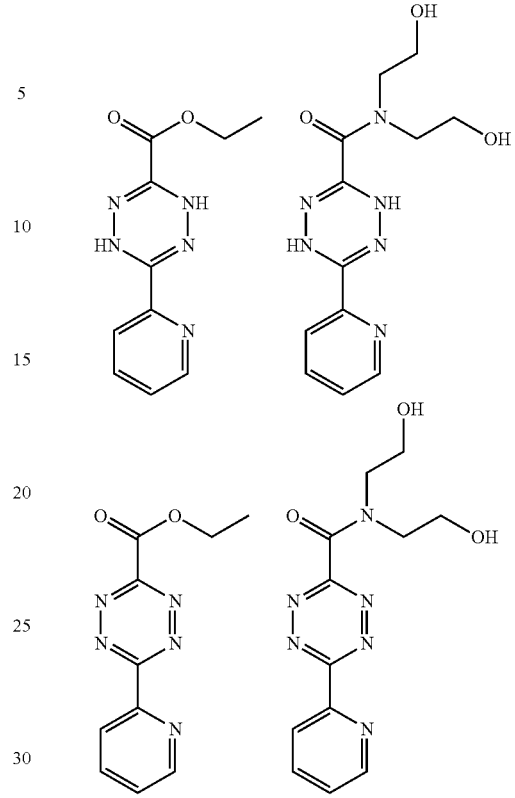

DETAILED DESCRIPTION OF THE INVENTION

Rapid bioorthogonal reactivity can be induced by controllable, catalytic stimuli using air as the oxidant. Methylene blue (4 μM) irradiated with red light (660 nm) catalyzes the rapid oxidation of a dihydrotetrazine ("DHTz") to a tetrazine ("Tz"), thereby turning on reactivity toward trans-cyclooctene dienophiles. Alternately, the aerial oxidation of dihydrotetrazines can be efficiently catalyzed by nanomolar levels of horseradish peroxidase under peroxide-free conditions. Selection of dihydrotetrazine/tetrazine pairs of sufficient kinetic stability in aerobic aqueous solutions is key to the success of these approaches. In this work, polymer fibers carrying dihydrotetrazines were catalytically activated and covalently modified by trans-cyclooctene conjugates of small molecules, peptides and proteins. In addition to visualization with fluorophores, fibers conjugated to a cell adhesive peptide exhibited a dramatically increased ability to mediate contact guidance of cells.

Figure 1:
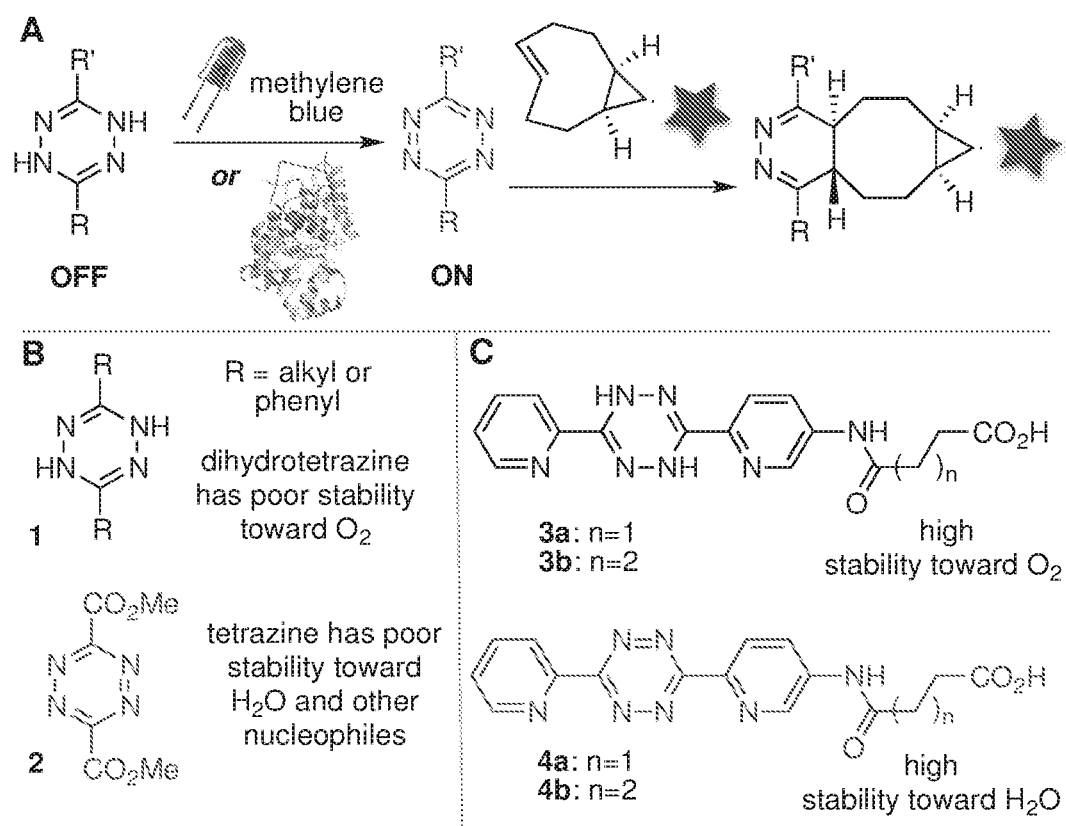
FIG. 1 shows dihydrotetrazine/tetrazine pairs according to the invention.

Described herein are the first examples of catalytic turn-on of the tetrazine ligation, where rapid bioorthogonal reactivity can be induced by a controllable, catalytic stimulus (FIG. 1, panel A). Inverse electron demand Diels-Alder adduction of a conformationally strained trans-cycloalkene (the star represents an arbitrary functional group) with the tetrazine occurs with an extremely high reaction rate. Either visible light and a photosensitizer, or very low loadings of horseradish peroxidase can be used to catalyze the oxidation of a dihydrotetrazine to a tetrazine.

Dienophiles other than trans-cycloalkenes can be used as well. For example, in some embodiments the invention provides compositions and methods in which a muted drug (e.g., a nitrogen mustard or doxorubicin) can be delivered locally to a tumor. See Scheme 1. Here an antibody-catalyst construct (either a photocatalyst, HRP catalyst, or synthetic Fe-porphyrin catalyst) can be retargeted to a tumor, and with a later injection of the prodrug could be used to trigger the oxidation reaction locally in vivo. The inventors have demonstrated that this conjugation/release works and is faster than can be observed by NMR.

Scheme 1

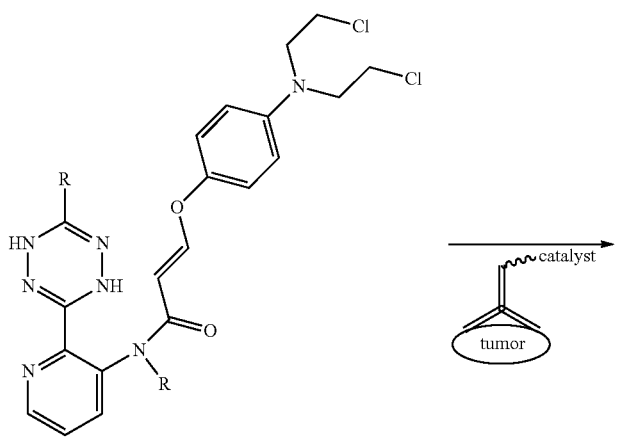

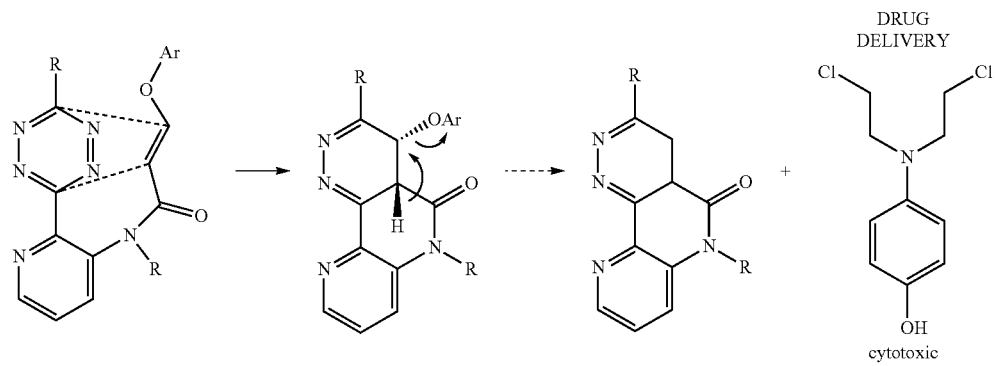

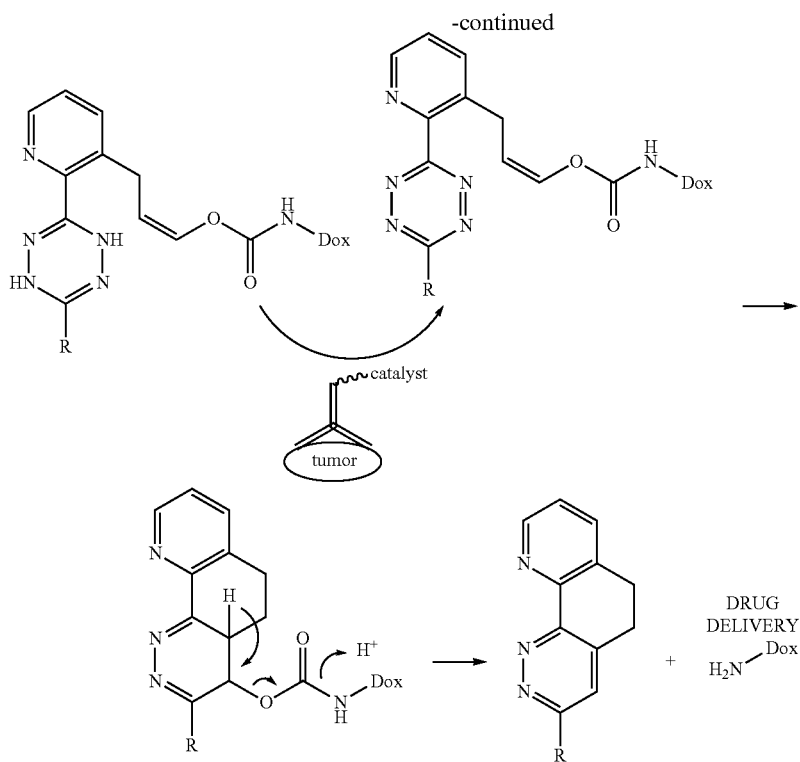

A challenge to the development of catalytic methods for turning on the tetrazine ligation was the identification of a DHTz/Tz pair that would be stable in both oxidation states (FIG. 1, panel B). For most redox couples, either the DHTz is too readily oxidized in air (e.g., 1), or the Tz is too reactive toward water and other nucleophiles (e.g., 2). The inventors show here that the dipyridyl DHTz/Tz pair (3/4) has good stability in both states (FIG. 1, panel C). Dihydrotetrazines 3 are highly resistant toward background oxidation in organic solvents, and a number of derivatives have been synthesized and shown stable even to silica gel chromatography. In ambient light, a 35 µM solution of 3a in MeOH was shown to retain 99 and 98% of the DHTz oxidation state after 1 and 2 hours, respectively. Aqueous solutions of 3a were handled in glassware that had been first rinsed with 2.0 mM EDTA in PBS to remove adventitious metal impurities. After standing in the dark at 25° C. in PBS buffer, a solution of 3a was monitored by UV-vis and shown to retain 99 and 96% of the DHTz oxidation state over 30 min and 2.5 hours respectively. In ambient light at 25° C. in PBS buffer, a solution of 3a was shown to retain 97 and 94% of the DHTz oxidation state after 1 and 2 hours, respectively. In PBS containing 10% mouse serum, 90% of 3a was retained in the DHTz oxidation state after 1 h. Analogs of tetrazines 4 have been described previously and used broadly for applications in nuclear medicine and cell imaging. In PBS buffer at 25° C., tetrazine 4a (800 µM) shows 98% and 83% fidelity after 2 h and 24 h, respectively. The stability of a radiolabeled derivative of tetrazine 4b has been studied by Robillard at 37° C. in PBS, serum and blood, with 97%, 87% and 59% retention of the tetrazine observed after 2 hours.

Figure 2:
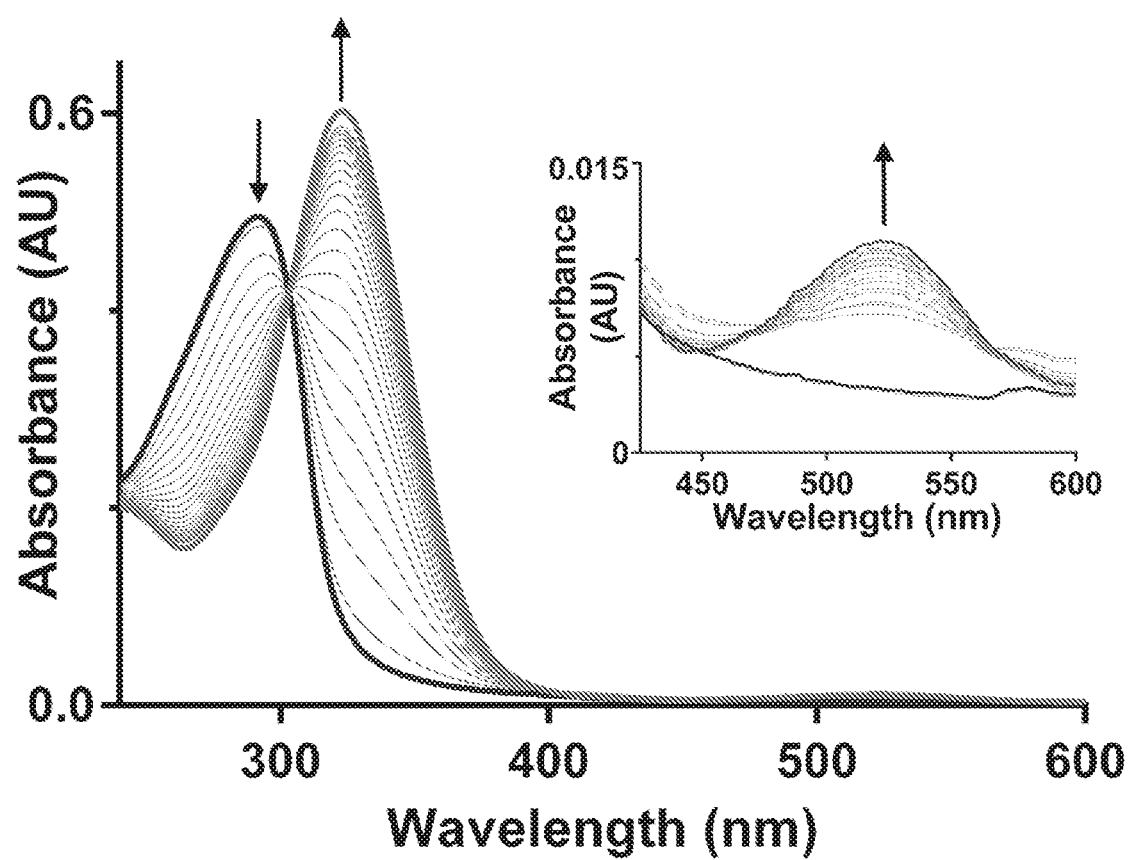
FIG. 2 shows UV-vis spectra of several compounds used in the practice of the invention.

Compound 3a has a maximum in the UV-vis spectrum at 292 nm, and 4a has a maximum at 325 nm with a less intense peak at 525 nm (FIG. 2). As a reference for their catalytic studies, the inventors first monitored the electrochemical oxidation of 3a in phosphate buffer, for which the voltammogram displays a single peak centered at 0.02 V. Under mildly oxidizing conditions (0.18 V relative to Ag/AgCl), a 1.1 mM solution of 3a turns pink and the oxidation to 4a proceeds cleanly with an isosbestic point at 303 nm. This isosbestic point was also conserved in the photocatalytic and enzymatic (FIG. 2) oxidations of 3a described below, and the spectroscopic changes at 292 and 325 nm were routinely used for monitoring reaction progress.

Upon addition of horseradish peroxidase (15 nM) the UV-vis spectrum was monitored every 10 seconds. With 50% conversion after 100 seconds, complete conversion of 3a to 4a is observed after 600 seconds, as evidenced by the decrease in the absorption at 292 nm and increase at 325 nm with an isosbestic point at 303 nm. Similar spectral changes are observed when 3a is electrochemically oxidized to 4a in aqueous solution, or when the oxidation of 3a to 4a is photocatalyzed by methylene blue.

The inventors have found that a number of photosensitizers in the presence of long wavelength visible light were found to catalyze the oxidation of 3a to 4a in the presence of air. Methylene blue was considered a particularly attractive sensitizer due to its clinical relevance, low molecular weight, low toxicity, high solubility, and an absorption spectrum ($\lambda_{max}$ 665 nm) that extends to the near IR. Further, methylene blue has previously been explored for applications in photodynamic therapy based on oxidation of indole-3-acetic acid. Rose bengal ($\lambda_{max}$ 550 nm), used in a range of biomedical applications, was also identified as an excellent sensitizer. Other successful sensitizers (irradiation wavelength) include acridine orange (528 nm), coomassie brilliant blue (528 nm), rhodamine B (590 nm), BODIPY (475 nm), safranin (528 nm), phenol red (528 nm), carboxylfluorescein (528 nm), and SiR Silarhodamine (purchased from Spirochrome, http://spirochrome.com/product/sir-cooh/, SC004-1 mg).

Figure 3:
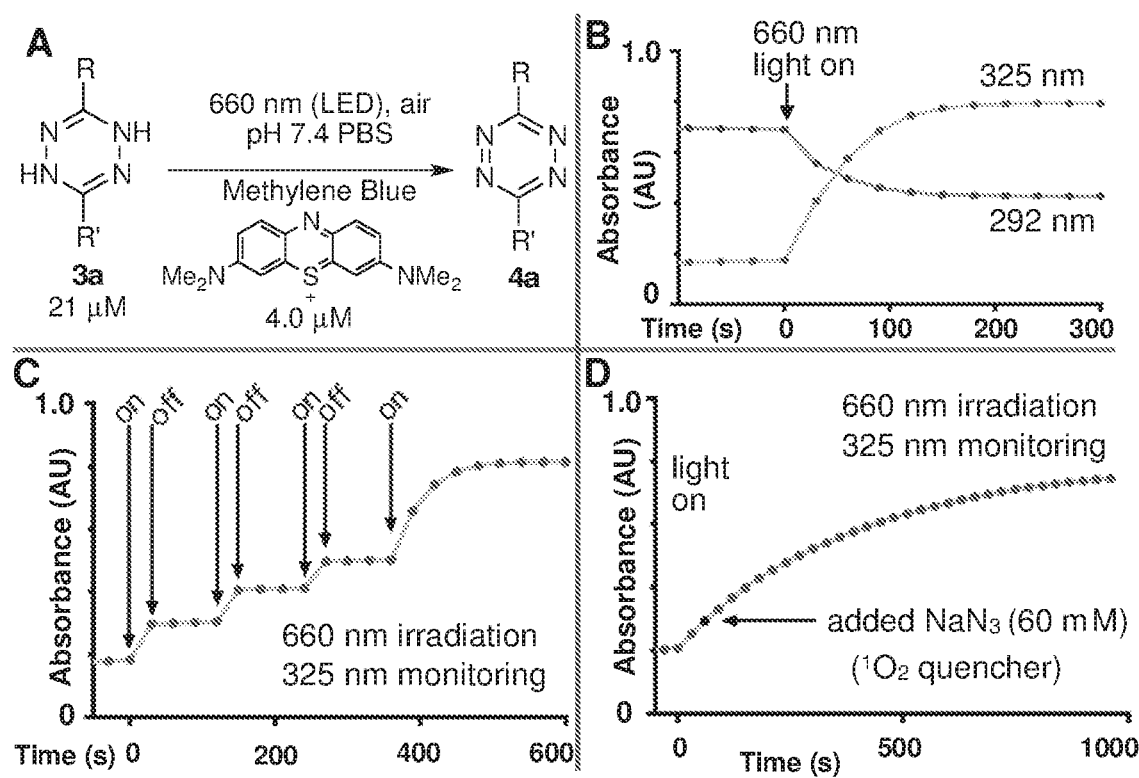
FIG. 3 shows the progress of photooxidation of a tetrahydrotetrazine to a tetrazine according to the invention.

Experiments to study the catalytic photooxidation were conducted at 25° C. in a thermostatted cuvette with stirring capability and a single top-mounted LED. A custom 3D printed light fixture was used to mount the LED directly above the cuvette and block ambient light. As shown in FIG. 3, panel B, irradiation of 3a (21 µM) with a 660 nm LED (9.1 mW/cm$^2$) in the presence of methylene blue (4 µM) in pH 7.4 PBS caused conversion to tetrazine 4a with quantitative yield within 200 seconds. Methylene blue (4 µM) also catalyzed the conversion of 3a to 4a in the presence of ambient light, with 47% conversion noted after 2 h. The light dependence of the methylene blue catalyzed oxidation was demonstrated by turning the LED on and off (FIG. 3, panel C). Similar light dependent on/off behavior was exhibited with either rose bengal or carboxyfluorescein with irradiation centered at 528 nm (2.3 mW/cm$^2$. Both methylene blue and rose bengal are known $^1O_2$ sensitizers, and the inventors therefore queried the influence of a $^1O_2$ quencher on the oxidation rate of 3a. Neither the methylene blue (FIG. 3, panel D) nor the rose bengal catalyzed photooxidations are impeded by the addition of 60 mM Na N$_3$. By contrast, the rate of the reaction between 2,5-diphenylisofuran with $^1O_2$ was greatly reduced when 23 mM NaN$_3$ was added. These experiments strongly imply that $^1O_2$ is not the oxidant of 3a under photocatalytic conditions. The mechanism of photooxidation more likely involves electron transfer and is the subject of ongoing study.

As a model of hypoxia, the inventors also demonstrated catalytic oxidation of 3a to 4a in solutions that were depleted in oxygen. Thus, a PBS solution of 3a was sparged with 98% nitrogen and 2% air, such that the final $O_2$ concentration was 5 µM. Addition of methylene blue (7 µM) and irradiation at 660 nm with monitoring by UV-vis indicated that conversion of 3a to 4a was complete within 30 minutes.

Figure 4:
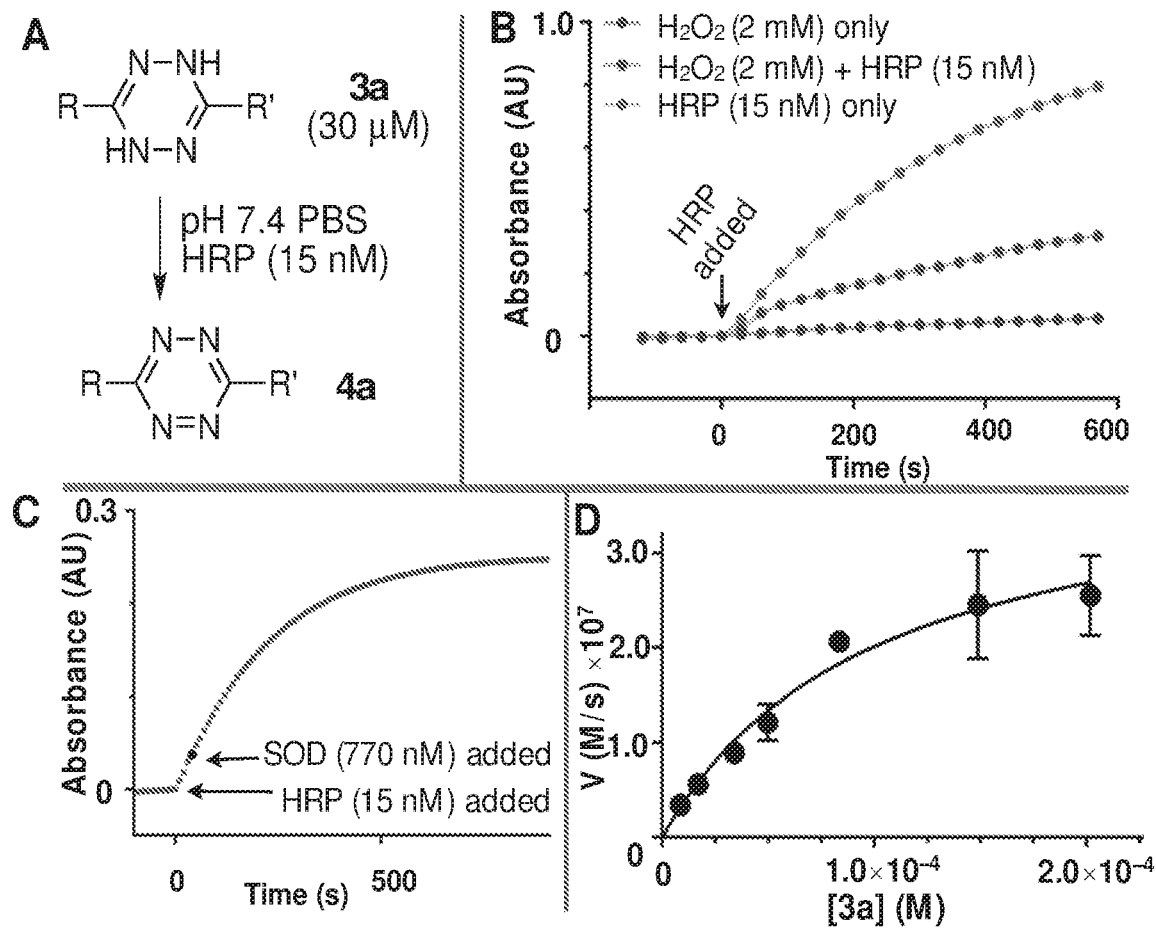
FIG. 4 shows the progress of horseradish peroxidase catalyzed oxidation of a tetrahydrotetrazine to a tetrazine according to the invention.

As a complement to these photocatalyzed reactions, the inventors observed that HRP can efficiently catalyze the oxidation of 3a in the dark at low enzyme concentration (15 nM) (FIG. 4). While HRP typically requires $H_2O_2$ as the terminal oxidant, the addition of HRP to a peroxide-free solution of 3a (30 µM) in PBS led to the rapid formation of 4a (FIG. 4, panel B). The rate of formation of 4a was significantly slower in the presence of 2 mM $H_2O_2$, and was near baseline in the presence of $H_2O_2$ but absence of HRP.

Neither cytochrome c nor hemoglobin were effective catalysts of DHTz oxidation, with only slow conversion of 3a to 4a even with heme concentrations that were nearly 3 orders of magnitude higher than that used with HRP. As shown in FIG. 4, panel C, the addition of superoxide dismutase (SOD, 770 nM) in PBS does not suppress the rate of the oxidation of 3a by HRP, providing evidence that superoxide is not responsible for the oxidation. Finally, it was observed that the oxidation of 3a by HRP in PBS containing EDTA (2.0 mM) follows Michaelis-Menten kinetics, with $K_m=1.0\times10^{-4}$ M, $k_{cat}=27$ s$^{-1}$, and $k_{cat}/K_m=2.7\times10^5$ M$^{-1}$ s$^{-1}$ (FIG. 4, panel D).

The light and enzyme-catalyzed reactions developed here enable the functionalization of polymeric materials with potential biomedical applications. The inventors previously disclosed [Adv Mater, 2015, 27, 2783-90] the production of peptide-containing polymer fibers through interfacial bioorthogonal polymerization based on tetrazine ligation using bis-tetrazine and bis-TCO monomers dissolved in immiscible solvents. These hydrogel-like polymer fibers, with diameters ranging from 6 to 11 µm when dry, are cytocompatible, biologically active and mechanically robust; they resemble many fibrous structures found in the human body and can be woven into complex, higher order assemblies for tissue engineering purposes. However, the use of interfacial polymerization to fabricate protein-containing polymer fibers is not trivial due to the possibility of protein denaturation by the required organic solvent.

Figure 5:
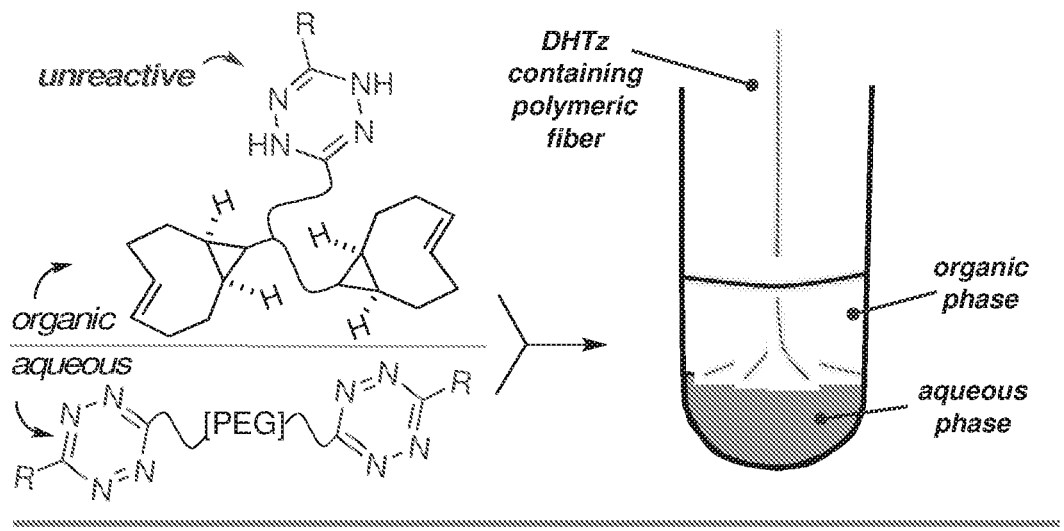
FIG. 5 is a schematic representation of interfacial polymerization involving a dihydrotetrazine-derived monomer according to the invention.
Figure 5:
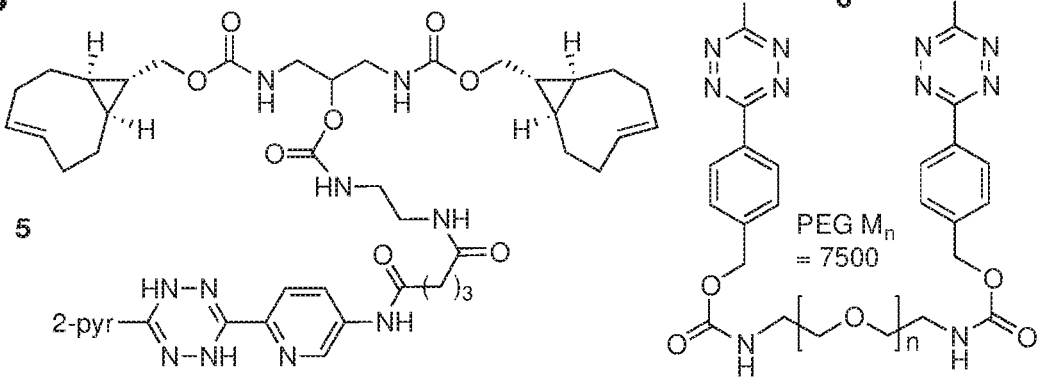
Figure 5:
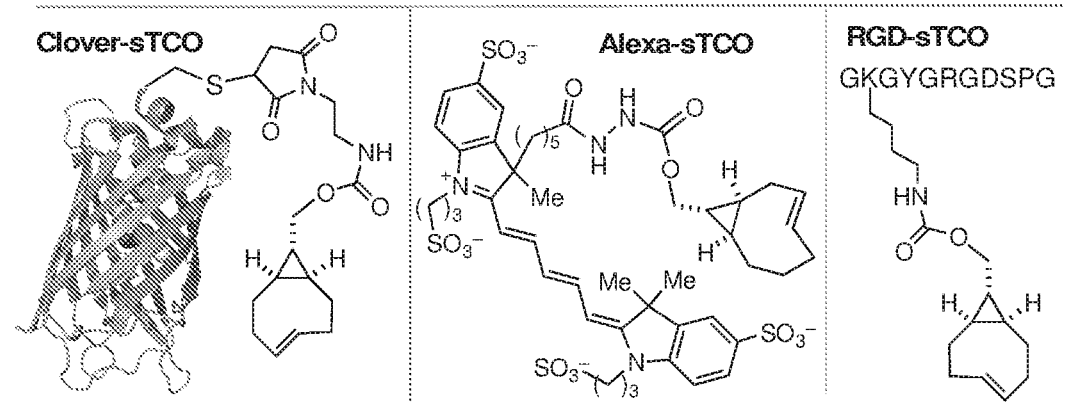

The inventors hypothesized that fibers could be synthesized with dihydrotetrazines and subsequently be activated and functionalized through bioconjugation. Thus, an aqueous solution of a water soluble bis-tetrazine monomer was combined with an organic soluble bis-sTCO containing a tethered dihydrotetrazine (FIG. 5, panel A). Again, meter-long, mechanically robust polymer fibers were continuously pulled from the liquid-liquid interface without fiber breakage (Video 1), confirming that the molecular weight of the polymer exceeds that required for chain entanglement. Subsequent oxidation by long wavelength photocatalysis was used to generate reactive tetrazine functionality, and the fibers could then be functionalized by sTCO conjugates of proteins, fluorophores or peptides. Shown in FIG. 5, panel B are the monomers 5 and 6 that were used to create the DHTz fibers. Notably, the DHTz containing bis-sTCO 5 was readily purified, stored and handled without special precautions. The sTCO conjugates used to elaborate the fibers are displayed in FIG. 5, panel B.

Figure 6:
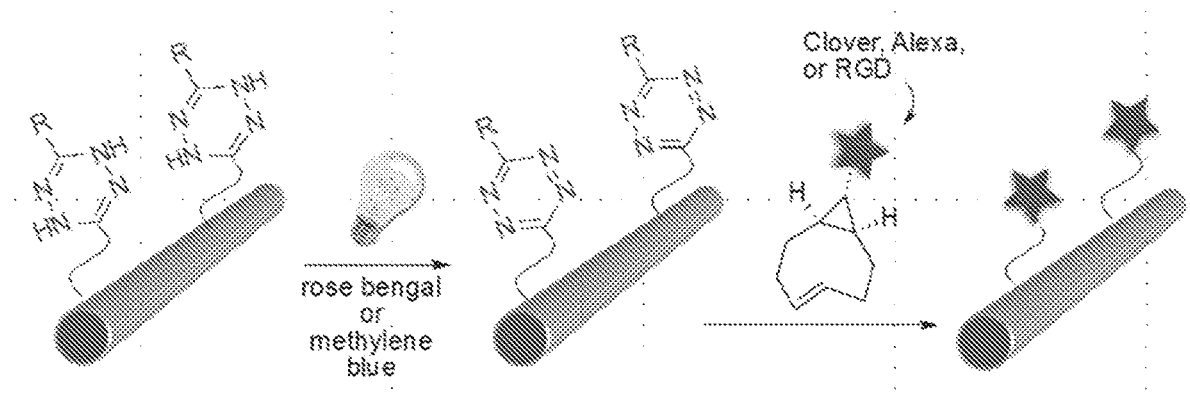
FIG. 6 is a schematic representation of fiber activation and subsequent conjugation according to the invention.

As shown in FIG. 6, the DHTz-fibers could be activated and then post-synthetically modified by treatment with Alexa-sTCO, Clover-sTCO or RGD-sTCO. The fibers were immersed in 100 µM sensitizer in PBS and irradiated with a simple incandescent bulb for 5 min. Methylene blue was used to activate fibers toward conjugations of Clover-sTCO or RGD-sTCO, and rose bengal was used as the sensitizer in experiments with Alexa-sTCO due to the spectral overlap of the Alexa dye with methylene blue. After irradiation, the fibers were rinsed, allowed to react with an sTCO conjugate for 1 min, and rinsed again. Confocal microscopy images of activated fibers conjugated by Alexa-sTCO or Clover sTCO showed that this short incubation time afforded labeling that was localized to the exterior of the fibers. Control experiments illustrated that dye conjugation was not efficient if the sensitizer or light was excluded. The inventors also found that HRP-catalyzed oxidation of dihydrotetrazines can be used to activate fibers toward bioconjugation, although in this instance photocatalytic activation is faster and more efficient.

The photocatalytic activation of tetrazines was also employed in the post-synthetic modification of the fibers with peptidic cues that promote cell adhesion and contact guidance. RGD-sTCO was conjugated to activated fibers through tetrazine ligation, and the resulting fibers were immobilized in silicone wells coated with poly(2-hydroxyethyl acrylate) to eliminate cellular adhesion to the culture wells. Here, imaging studies revealed fibroblasts selectively attached to RGD-tagged fibers and elongated along the long axis of the fibers, adopting a healthy fibroblastic morphology. Cell attachment and spreading was not observed in control experiments where the sensitizer and/or the RGD-sTCO were excluded. Instead, cells clustered to form multicellular spheroids, indicating the initiation of nemesis. These studies demonstrate the ability to functionalize biomimetic fibers with molecules that can enable visualization or promote cell adhesion.

As disclosed herein, photocatalytic and enzymatic methods for turning on the tetrazine ligation provide a new tool for modulating the cell adhesive properties of a biomaterial. The inventors hypothesized that an intramolecular version of the Diels-Alder reaction would be rapid even when using an unstrained alkene, thereby enabling the synthesis of a drug delivery construct.

Figure 7:
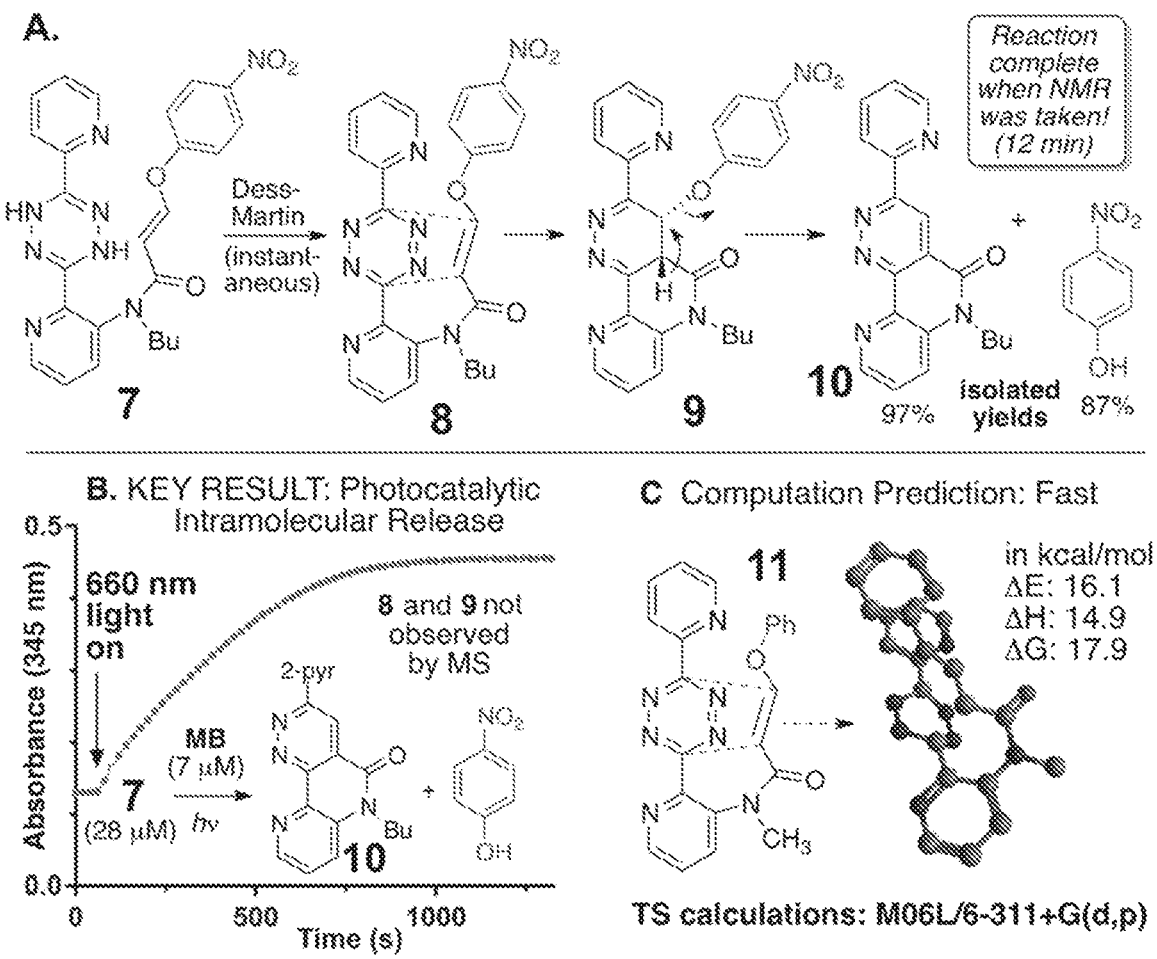
FIG. 7 shows experimental results demonstrating the viability of near infrared (NIR) photocatalytic payload release according to the invention.

Shown in FIG. 7 are results that demonstrate the viability of NIR photocatalytic payload release. As shown in FIG. 7, panel C, high-level transition state calculations predicted that the intramolecular reaction of 11 would be rapid. Encouraged by calculation, the inventors synthesized the compound 7, where p-nitrophenol serves as a model payload that can be readily monitored by UV and NMR (FIG. 7, panel A). To study the Diels-Alder/elimination sequence (8→9→10), the inventors chose to oxidize 7 with Dess-Martin periodinane—a reagent that instantaneously oxidizes dihydrotetrazines to tetrazines. They found that 7 reacts rapidly with Dess-Martin reagent, and upon the first ability to monitor by $^1$H NMR in CDCl$_3$ observed only product 10 and p-nitrophenol, which can be isolated in 97% and 87% yields, respectively. Upon LED irradiation (660 nm, 9.1 mW/cm$^2$) of 7 (28 μM) in MeOH in the presence of catalytic methylene blue (7 μM), complete oxidation/Diels-Alder/payload release within 15 minutes was observed (FIG. 7, panel B). In this photocatalytic reaction, aliquots by ESI-MS were analyzed, and intermediates 8 and 9 were not detected.

Figure 8:
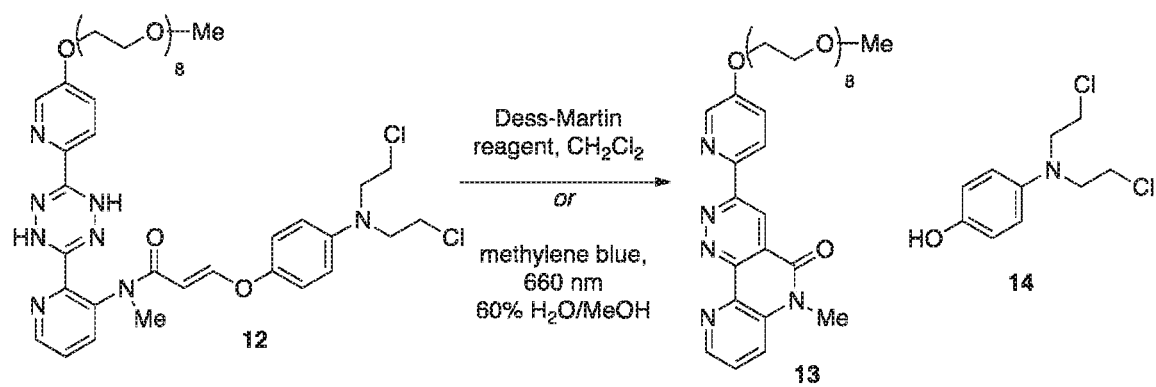
FIG. 8 shows a compound capable of functioning as a prodrug that, in the presence of an appropriate catalyst, can produce a phenolic nitrogen mustard drug, according to the invention.

Based on these findings, the inventors synthesized the compound 12, seen in FIG. 8, which has the potential to function as a prodrug that, in the presence of an appropriate catalyst, can produce the phenolic nitrogen mustard drug 14. Upon oxidation with Dess-Martin reagent, compound 12 was converted to the product 13 and the mustard 14. Monitoring by TLC and $^1$H NMR showed that the reaction was complete within 10 minutes. The reaction of 12 to produce 13 and 14 could also be promoted by irradiating a solution of 12 in 60% H$_2$O/MeOH for 30 min with a 660 nm LED light source in the presence of catalytic amounts of methylene blue with monitoring by UV-Vis. The complete conversion to product 13 could be observed by UV-vis within 30 minutes.

Inventive Methods

The invention provides a method for catalytically converting a dihydrotetrazine 1 into a tetrazine 2, wherein one R group on the dihydrotetrazine 1 is a substituted or unsubstituted aryl, heteroaryl, alkyl, alkenyl, alkynyl, carbonyl, or heteroatom-containing group, and the other R group is selected from the group consisting of H and substituted or unsubstituted aryl, heteroaryl, alkyl, alkenyl, alkynyl, carbonyl,- or heteroatom-containing groups;

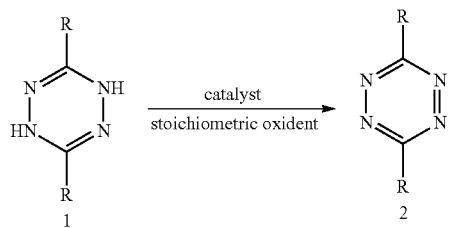

wherein the method comprises oxidizing dihydrotetrazine 1 in a reaction medium in the presence of a catalyst and a stoichiometric oxidant.

The method may further comprise trapping the tetrazine with a dienophile, which may be an alkene or an alkyne, for example a strained alkene or strained alkyne. Specific examples include substituted trans-cyclooctenes or substituted cyclooctynes. The dienophile may be present with the dihydrotetrazine in the reaction medium before the catalyst is added. The method may unite one or more bimolecular entities selected from the group consisting of proteins, DNA, and RNA, or it may attach a fluorescent molecule or fluorescent protein to another small molecule or a biomolecule. The method may attach a molecule to the surface of a fiber or a glass slide.

The dihydrotetrazine 1 used in performing a method according to the invention may have one R group on the dihydrotetrazine that is a substituted or unsubstituted aryl, heteroaryl, alkyl, alkenyl, alkynyl, carbonyl, or heteroatom-containing group, and the other R group is an aryl, heteroaryl, alkyl, or heteroatom-containing group to which is attached an alkene or alkyne moiety; wherein the alkene or alkyne moiety reacts intramolecularly with the tetrazine by Diels-Alder cycloaddition to form an adduct. In such cases said alkene moiety is attached, that moiety can bear a leaving group directly attached to the C1 or C2 carbon thereof, and the adduct undergoes elimination to produce a cycloadduct and liberate the leaving group. The leaving group may be an OR$^1$, SR$^1$, or NR$^1$R$^2$ group, wherein R$^1$ and R$^2$ are each individually selected from the group consisting of H, aryl, heteroaryl, alkyl, alkene, alkyne, carbonyl, and heteroatom-containing groups. Or, the leaving group may be OR$^1$ in which R$^1$ is an aryl or heteroaryl group, wherein the elimination produces a phenol or a heterophenol. Or, the leaving group may be O(CO)NR$^1$R$^2$, wherein R$^1$ and R$^2$ are each individually selected from the group consisting of H, aryl, heteroaryl, alkyl, alkene, alkyne, carbonyl, and heteroatom-containing groups. Elimination of the leaving group may result in formation of a biologically active material, for example a drug. The color and/or fluorescence properties of the products formed after said elimination differ from those prior to said oxidizing.

The catalyst may be a photocatalyst, and the method includes exposing the reaction mixture to light to activate the catalyst. The light may have a wavelength of 650 nm or longer.

The photocatalyst may be one of the following compounds or a derivative thereof:

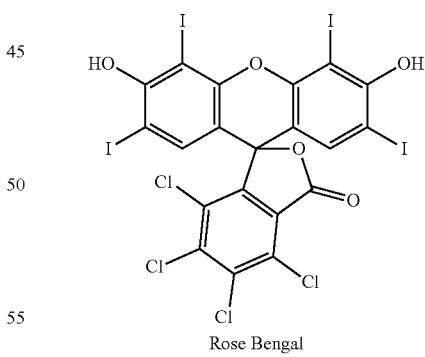

Rose Bengal

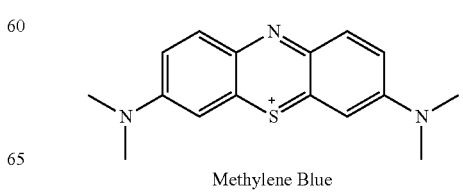

Methylene Blue

13
-continued
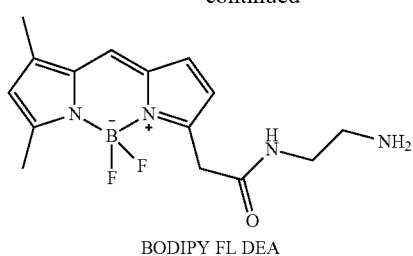
BODIPY FL DEA
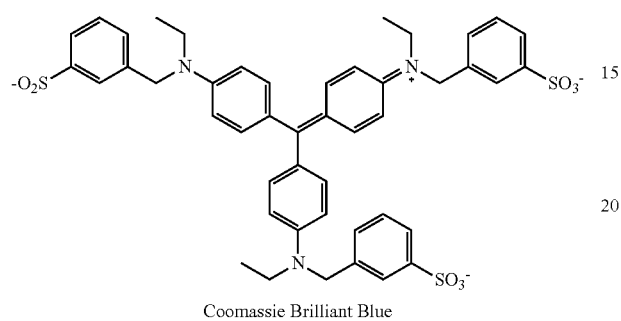
Coomassie Brilliant Blue
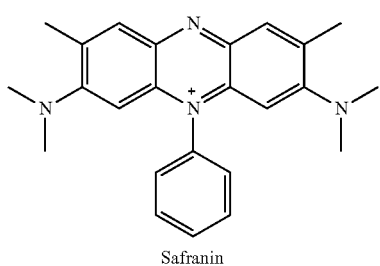
Safranin
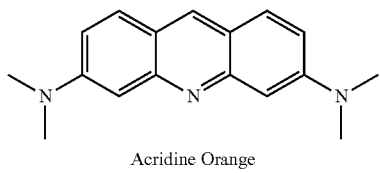
Acridine Orange
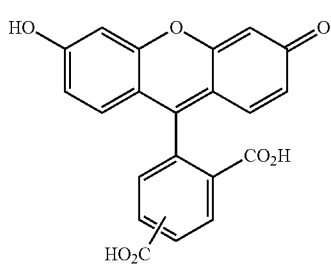
Fluoroceins
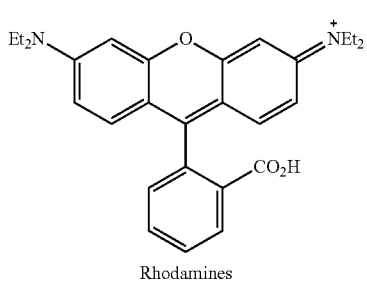
Rhodamines
14
-continued
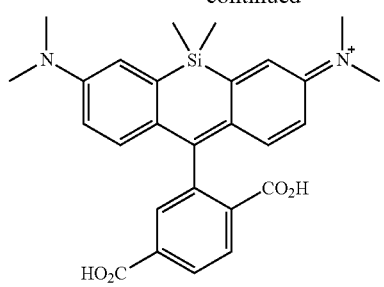
Si-Rhodamine
(purchased from spirochrome SC004-1 mg)
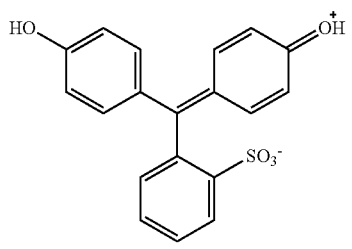
Phenol Red
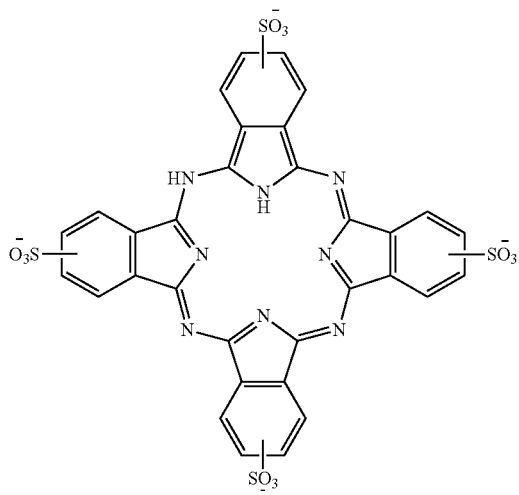
Phthalocyanine tetrasulfonate
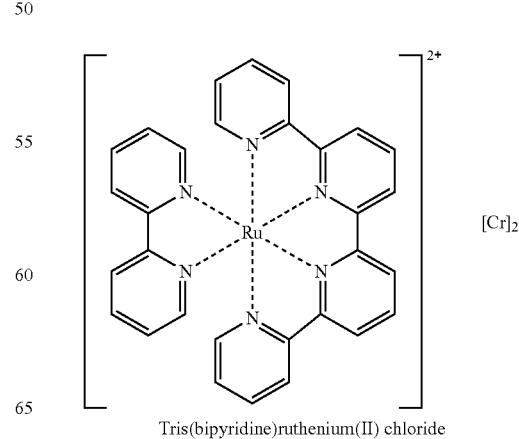
Tris(bipyridine)ruthenium(II) chloride -continued

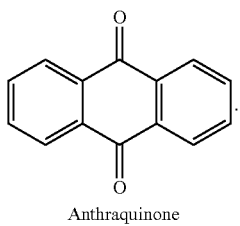
Anthraquinone

Or, the catalyst may be an enzyme, for example horseradish peroxidase. The catalyst may also be a metal compound, for example $FeCl_2$ or a metal-ligand complex.

Exemplary metal-ligand complexes include iron-ligand complexes, for example an iron-porphyrin.

Specific examples include Fe(III)tetrakis (1-methyl-4-pyridyl) porphyrin pentachloride and Fe(III)5,10,15,20-tetrakis(4-sulfonatophenyl)porphyrinato chloride.

The stoichiometric oxidant may be $O_2$, optionally atmospheric $O_2$. The $O_2$ may be at a concentration lower than that found under atmospheric conditions. Alternatively, the stoichiometric oxidant may be hydrogen peroxide or a disulfide.

The methods described herein may be carried out in a biological milieu, for example cell media, blood, serum, and cell lysates.

Inventive Compounds

The invention provides compounds useful in performing the methods described herein, or resulting from performing them. Examples of such compounds follow:

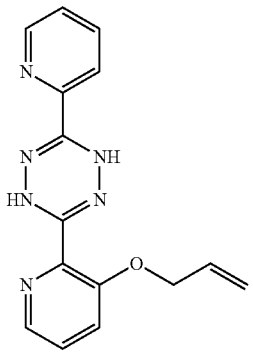

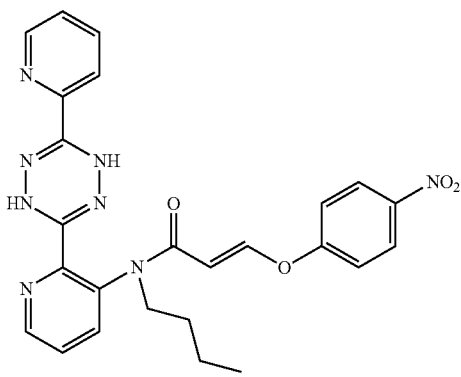

-continued

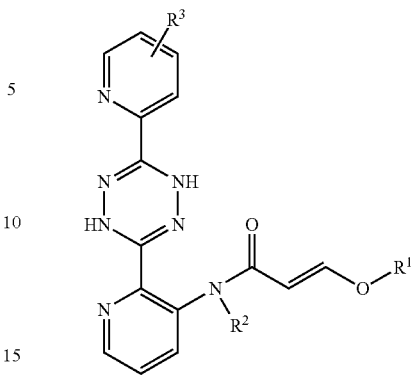

wherein $R^1$, $R^2$ and $R^3$ are each individually selected from the group consisting of H, aryl, heteroaryl, alkyl, alkenyl, alkynyl, carbonyl, and heteroatom-containing groups;

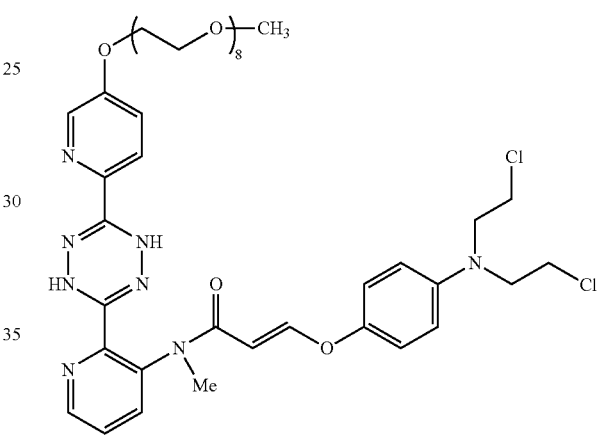

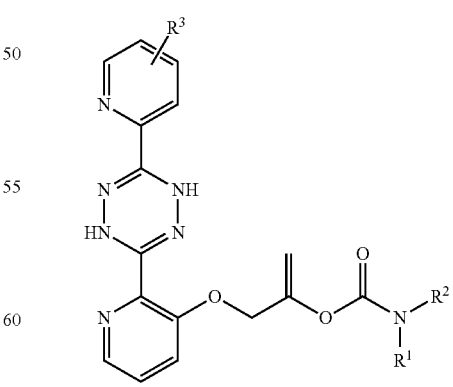

wherein $R^1$, $R^2$ and $R^3$ are each individually selected from the group consisting of H, aryl, heteroaryl, alkyl, alkenyl, alkynyl, carbonyl, and heteroatom-containing groups;

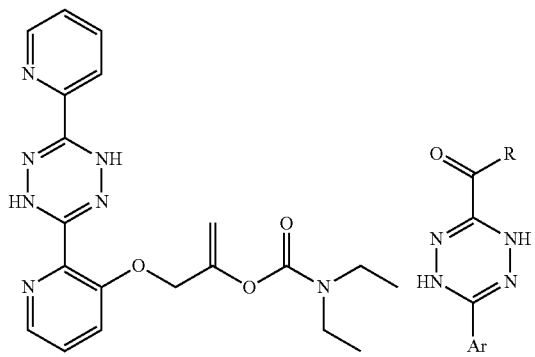

wherein R is selected from the group consisting of H, aryl, heteroaryl, alkyl, alkenyl, alkynyl, and heteroatom-containing groups, and Ar is an aromatic or heteroaromatic group

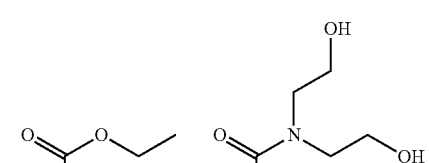

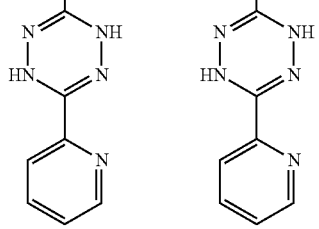

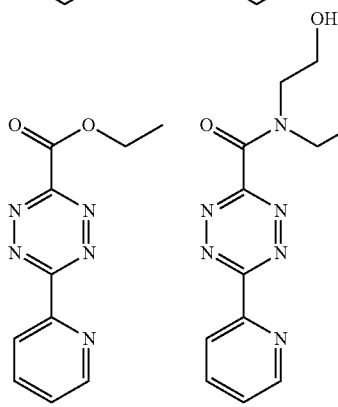

EXAMPLES

Synthetic Procedures

General Considerations

All reactions were carried out in glassware that was flame-dried under vacuum and cooled under nitrogen. THF was purified by distillation from Na/benzophenone. Phosphate-buffered saline (PBS) was prepared from diluting PBS 10× stock solution (Fisher Scientific). Flash Chromatography was performed using normal phase Silicycle silica gel (40-63D, 60 Å). An APT pulse sequence was used for $^{13}$C NMR spectra, where methylene and quaternary carbons appear 'up' (u), and methine and methyl carbons appear 'down' (dn). Other solvents and reagents were purchased from commercial sources without additional purification.

Synthesis of 4-oxo-4-((6-(6-(pyridin-2-yl)-1,4-dihydro-1,2,4,5-tetrazin-3-yl)pyridin-3-yl)amino)butanoic Acid (3a)

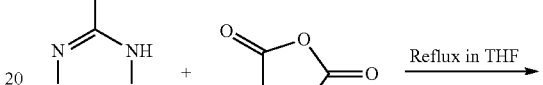

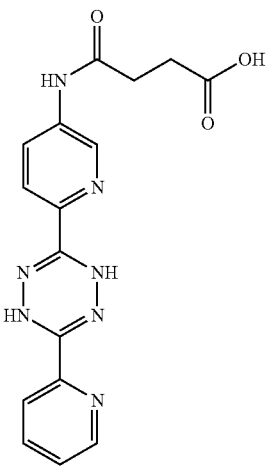

3a, 90%

To a dry round-bottom flask was added 6-(6-(pyridin-2-yl)-1,4-dihydro-1,2,4,5-tetrazin-3-yl)pyridin-3-amine (200 mg, 0.79 mmol, prepared as described in R. Selvaraj, J. M. Fox, *Tetrahedron Lett.* 2014, 55, 4795-4797), succinic anhydride (400 mg, 4.00 mmol) and anhydrous THF (8 mL). The mixture was refluxed for 24 hours at 60° C. and then cooled by an ice bath. The precipitate was filtered and sequentially washed by THF (2 mL) and ethyl acetate (3×3 mL) and dried to yield the title compound (251 mg, 0.71 mmol, 90%) as an orange solid.

Synthesis of 5-oxo-5-((6-(6-(pyridin-2-yl)-1,4-di-hydro-1,2,4,5-tetrazin-3-yl)pyridin-3-yl)amino)pentanoic Acid (3b)

Synthesis of 4-oxo-4-((6-(6-(pyridin-2-yl)-1,2,4,5-tetrazin-3-yl)pyridin-3-yl)amino)butanoic Acid (4a)

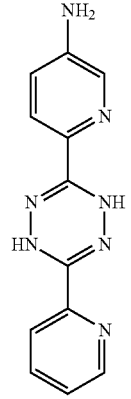
+
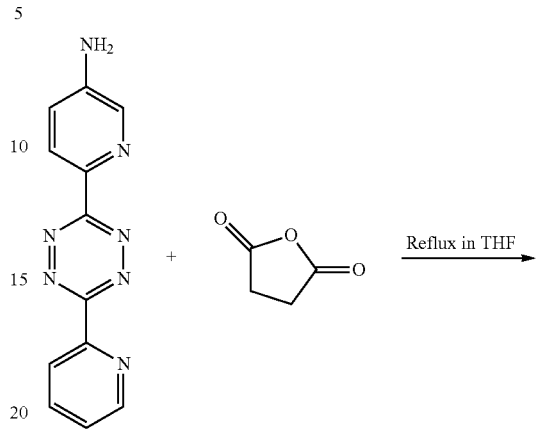

Reflux in THF

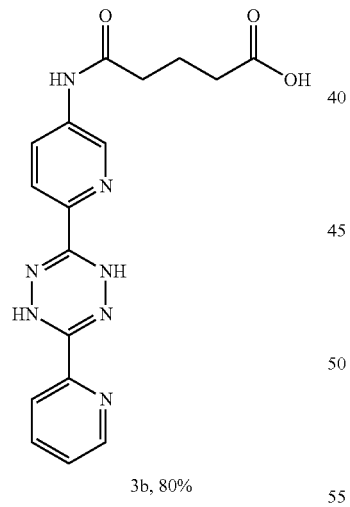

3b, 80%

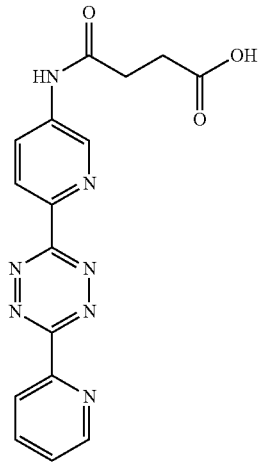

4a, 46%

To a dry round-bottom flask was added 6-(6-(pyridin-2-yl)-1,4-dihydro-1,2,4,5-tetrazin-3-yl)pyridin-3-amine (1.87 g, 7.39 mmol, prepared as described in R. Selvaraj, J. M. Fox, *Tetrahedron Lett.* 2014, 55, 4795-4797), glutaric anhydride (1.01 g, 8.87 mmol) and anhydrous THF (70 mL). The mixture was refluxed for 24 hours at 60° C. and then cooled by an ice bath. The precipitate was filtered on a Buchner funnel and sequentially rinsed by THF (10 mL) and ethyl acetate (3×10 mL) and dried to yield the title compound (2.16 g, 5.89 mmol, 80%) as an orange solid.

To a flame dried flask under nitrogen, 6-(6-(pyridin-2-yl)-1,2,4,5-tetrazin-3-yl) pyridin-3-amine (50 mg, 0.20 mmol, prepared as described in R. Selvaraj, J. M. Fox, *Tetrahedron Lett.* 2014, 55, 4795-4797) and succinic anhydride (114 mg, 1.14 mmol) were added. The flask was charged with tetrahydrofuran (4 mL) and heated to 70° C. for 21 hours. The reaction solution was cooled to room temperature before diluting with ethyl acetate (4 mL) and further chilling to 0° C. for 15 minutes. Filtering and rinsing with ethyl acetate and diethyl ether (3×5 mL) yielded a dark, cherry red powder. The solid was dissolved in 1.5 mL warm dimethylformamide and purified by chromatography (10-100% acetone in hexanes then 1% acetic acid in acetone on 10% triethylamine in hexanes treated silica). After drying in vacuo, the recovered pink solid was rinsed with ice water yielding the title compound (32 mg, 46%). An additional 12 mg (24%) of 6-(6-(pyridin-2-yl)-1,2,4,5-tetrazin-3-yl)pyridin-3-amine was recovered during chromatography.

21

Synthesis of 2,5-dioxopyrrolidin-1-yl 5-oxo-5-((6-(6-(pyridin-2-yl)-1,4-dihydro-1,2,4,5-tetrazin-3-yl)pyridin-3-yl)amino)pentanoate (S1)

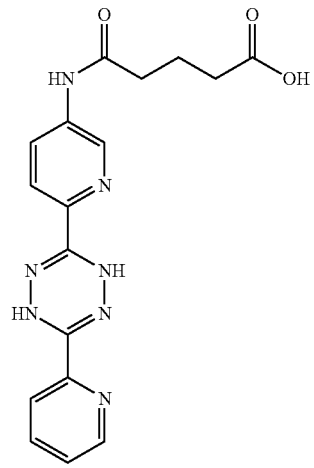

+

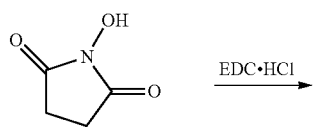 EDC·HCl

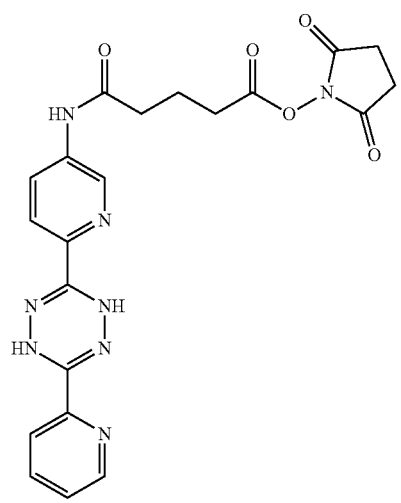

S1, 80%

To a dry round-bottom flask was added 1 (200 mg, 0.54 mmol), N-hydroxysuccinimide (125 mg, 1.09 mmol), N-(3-dimethylaminopropyl)-N'-ethylcarbodiimide hydrochloride (209 mg, 1.09 mmol) and anhydrous DMF (2 mL). The mixture was stirred for 1 hour at room temperature. DMF was removed by rotary evaporation at 50° C. using an efficient vacuum pump (<1 torr). The crude product was dissolved in acetone and then concentrated onto silica gel. Purification by column chromatography using a gradient (10%-70%) of acetone in hexanes yielded 202 mg (0.44 mmol, 80%) of the title compound as an orange solid.

22

Synthesis of bis(((E)-bicyclo[6.1.0]non-4-en-9-yl)methyl)(2-hydroxypropane-1,3-diyl)dicarbamate (S2)

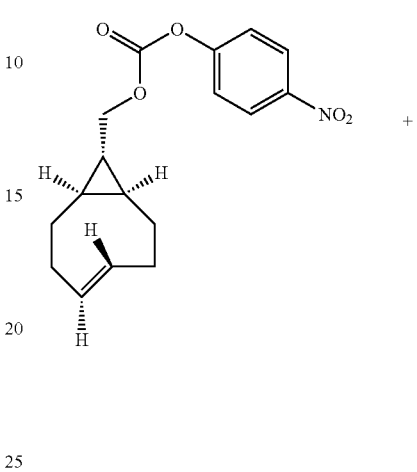 +

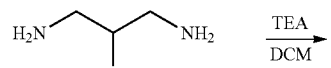

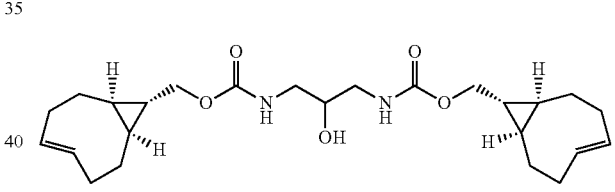

S2, 87%

A dry round-bottom flask was sequentially charged via syringe with a solution of 1,3-diamino-2-propanol (120 mg, 1.33 mmol) in anhydrous dichloromethane (20 mL) followed by anhydrous triethylamine (744 µL, 5.37 mmol) and (1R,8S,9R,4E)-bicyclo[6.1.0]non-4-en-9-ylmethyl(4-nitrophenyl) carbonate (930 mg, 2.93 mmol, prepared as described in M. T. Taylor, M. L. Blackman, O. Dmitrenko, J. M. Fox, *J. Am. Chem. Soc.* 2011, 133, 9646-9649). The mixture was stirred overnight at room temperature, diluted with dichloromethane (30 mL) followed by exhaustive aqueous wash (5×50 mL). The organic layer was dried with MgSO$_4$, filtered and then the solvent was removed with a rotary evaporator. Purification by column chromatography first using 10% ethyl acetate in hexanes then switching to 30% acetone in hexanes yielded the title compound (520 mg, 1.16 mmol, 87%) as a colorless oil.

Synthesis of bis(((E)-bicyclo[6.1.0]non-4-en-9-yl)methyl)(2-(((4-nitrophenoxy)carbonyl)oxy)propane-1,3-diyl)dicarbamate (S3)

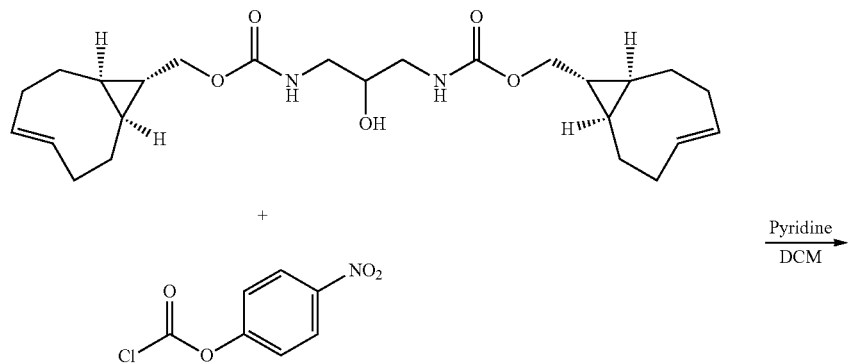

A dry round-bottled flask was charged with S2 (500 mg, 1.12 mmol). Anhydrous dichloromethane (30 mL) and pyridine (0.23 mL, 2.80 mmol) were added to the flask. A solution of 4-nitrophenylchloroformate (271 mg, 1.34 mmol) in anhydrous dichloromethane (4 mL) was added to the flask via syringe and the solution was stirred for 1 h at room temperature. Saturated aq. NH₄Cl was added to the mixture and the layers were separated, and the aqueous layer was extracted twice with dichloromethane. The organic layers were combined, dried with MgSO₄ and filtered, and the solvent was removed using a rotary evaporator. Purification by column chromatography (10% to 30% ethyl acetate/hexanes) yielded 450 mg (0.74 mmol, 66%) of the title compound as a white solid.

Synthesis of bis(((E)-bicyclo[6.1.0]non-4-en-9-yl)methyl)(2-(((2-aminoethyl)carbamoyl)oxy)propane-1,3-diyl)dicarbamate (S4)

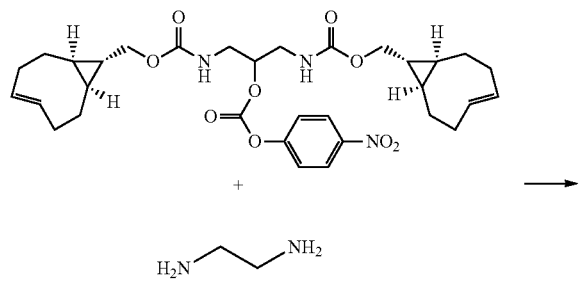

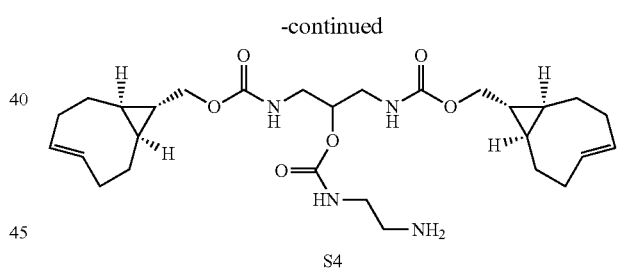

A dry round-bottom flask was sequentially charged via syringe with ethylenediamine (218 μL, 3.27 mmol) followed by a solution of S3 (100 mg, 0.16 mmol) in anhydrous dichloromethane (4 mL). The solution was stirred for 1 h at room temperature, diluted with dichloromethane (15 mL) and followed by exhaustive aqueous washes (5×30 mL). The organic layer was dried with MgSO₄, filtered and concentrated down with a rotary evaporator to afford the title compound (80 mg, 92% crude yield) as a pale yellow solid. The crude product was carried to the next step of synthesis without further purification.

Synthesis of bis(((E)-bicyclo[6.1.0]non-4-en-9-yl)methyl)(2-(((2-(5-oxo-5-((6-(6-(pyridin-2-yl)-1,4-dihydro-1,2,4,5-tetrazin-3-yl)pyridin-3-yl)amino)pentanamido)ethyl)carbamoyl)oxy)propane-1,3-diyl) dicarbamate (5)

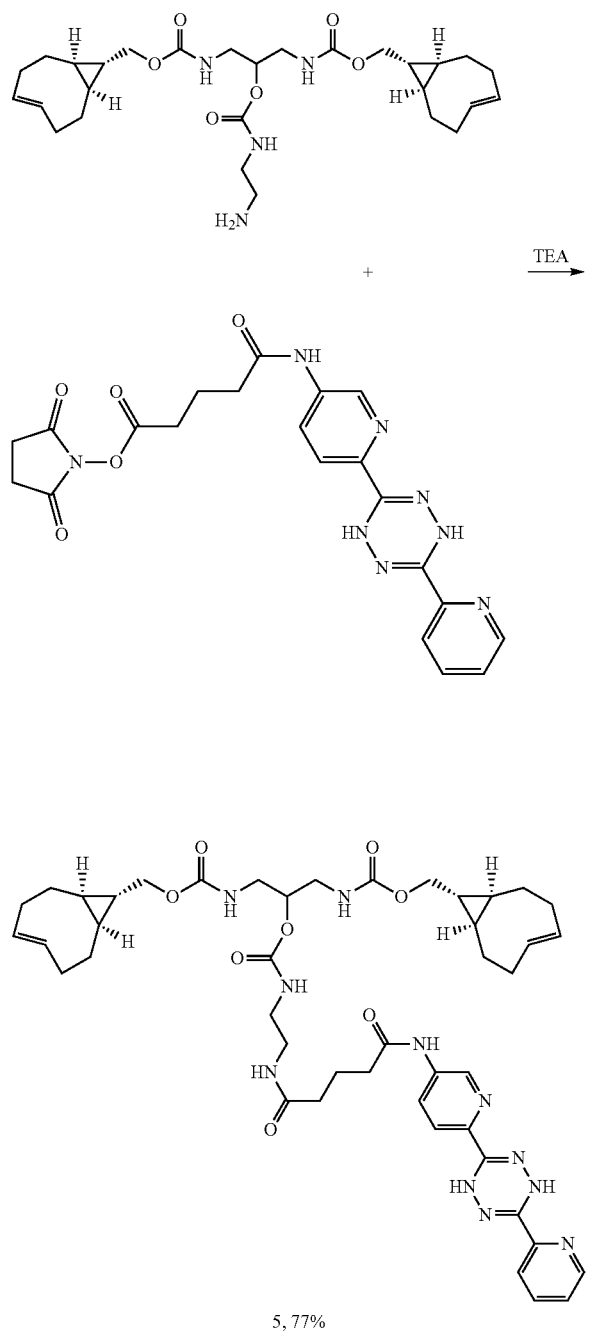

5, 77%

To a dry round-bottom flask was added S4 (39 mg, 73.3 µmol), S1 (25 mg, 53.9 µmol) and a solution of triethylamine (17 µL, 0.12 mmol) in dichloromethane (2 mL). The mixture was stirred for 1 hour under room temperature and then concentrated onto silica gel using a rotary evaporator. Purification by column chromatography using a gradient (20%-70%) of acetone in hexanes yielded the title compound (37 mg, 42.0 µmol, 77%) as an orange solid.

N-Terminal Cysteine-Tagged Clover-GFP

The Clover construct sequence (A. J. Lam, F. St-Pierre, Y. Gong, J. D. Marshall, P. J. Cranfill, M. A. Baird, M. R. McKeown, J. Wiedenmann, M. W. Davidson, M. J. Schnitzer, et al., Nat. Methods 2012, 9, 1005-12) coding for this green fluorescent protein with an additional N-terminal extension (MGSGSCGSGS), was ordered from GeneWiz (http://www.genewiz.com/) and inserted into the pET28a vector via XbaI and NcoI restriction sites. Plasmids were transformed and expressed in BL21(DE3) cells. Cells were grown at 37° C. in 2 L of Luria-Bertani medium containing 30 µg/mL kanamycin and induced by the addition of 1.0 mM isopropyl β-D-1-thiogalactopyranoside when the absorbance at 600 nm reached 0.6 AU. Cells were grown for 6 h and collected by centrifugation (at 3,000 g for 10 minutes at 4° C.). Cell pellets were resuspended in 50 mM phosphate buffer, pH 7.5, containing 500 mM NaCl, 1 mM phenylmethylsulfonyl fluoride, 300 µg/mL lysozyme, and 1 µM leupeptin. Cells were disrupted by two passes through a French pressure cell (at 10,000 psi), and the resulting homogenate was briefly sonicated to shear DNA. The suspension was clarified by centrifugation (at 17,000 g for 30 minutes at 4° C.), and the supernatant was rocked with 3 mL of a nickel affinity resin (Sigma HIS-Select Nickel Affinity Gel) for 1 hour at 4° C. The resin-bound protein was loaded into a small column and washed with 40 mL of 50 mM phosphate buffer, pH 7.5, containing 500 mM NaCl, followed by 40 and 20 mL washes of the same buffer with an additional 5 and 20 mM imidazole respectively. The constructs were then eluted from the column with 20 mL of 50 mM phosphate buffer, pH 7.5, containing 500 mM NaCl and 200 mM imidazole, and then dialysed overnight against 4 L of 50 mM phosphate buffer, pH 7.5, containing 1 mM EDTA. The protein was then concentrated to 1 mL and stored at −20° C. The protein construct was >95% pure by SDS-PAGE.

Figure 9:
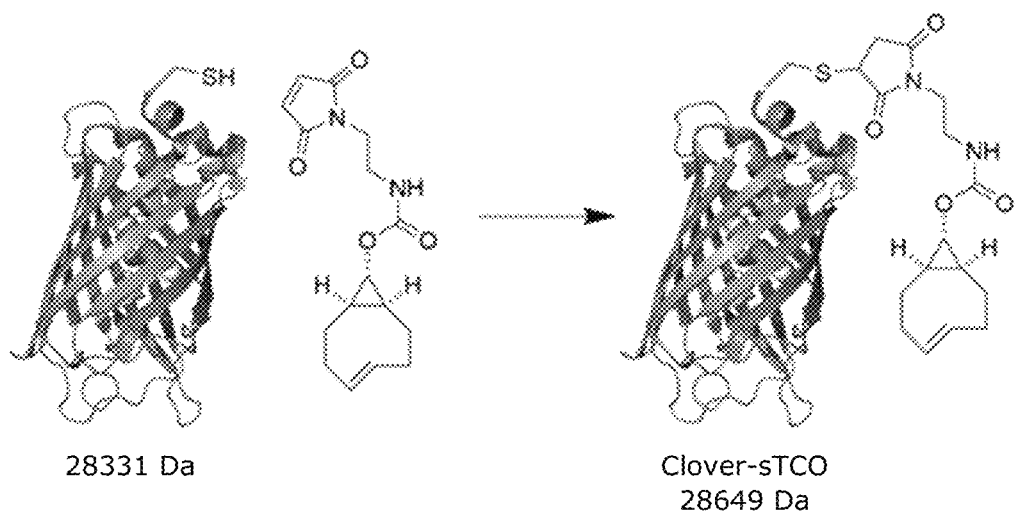
FIG. 9 shows an exemplary preparation of Clover-sTCO, according to the invention.

Preparation of Clover-sTCO, as Shown in FIG. 9

A 0.5 mL solution of 1.02 mM Clover protein solution in phosphate buffer (50 mM, 1 mM EDTA, pH 7.5) was reduced with an aqueous solution of tris(hydroxypropyl)phosphine (THP) (50 µL of a 100 mM solution, 10 mM final concentration) for 2 hours at room temperature. The reduced protein was loaded onto a desalting column (GE Healthcare PD-10) pre-equilibrated and eluted with phosphate buffer (50 mM, 1 mM EDTA, pH 7.5). Approximately 1.2 mL of pure fractions was collected, containing fully reduced 104 µM Clover protein. The thiol content of the resulting solution was verified by treating a small volume with Ellman's reagent. Concentration was determined by UV-Vis spectrometry using the Clover extinction coefficient of 111,000 $M^{-1}$ $cm^{-1}$. Approximately 1.2 mL of a 104 µM reduced Clover solution in phosphate buffer (50 mM, 1 mM EDTA, pH 7.5) was incubated with a 10 mM DMSO solution of sTCO-Maleimide1 (62.4 µL, final concentration 520 µM) for 30 minutes. The reaction solution was concentrated using a centrifugal filter (Millipore Ultracel 3 k MWCO) at 4,000 rpm for 15 minutes. The concentrated solution was loaded onto a desalting column (GE Healthcare PD-10) pre-equilibrated and eluted with phosphate buffer (50 mM, 1 mM EDTA, pH 7.5). Approximately 1.0 mL of 103 µM-conjugated Clover protein was collected.

Synthesis of RGD-sTCO

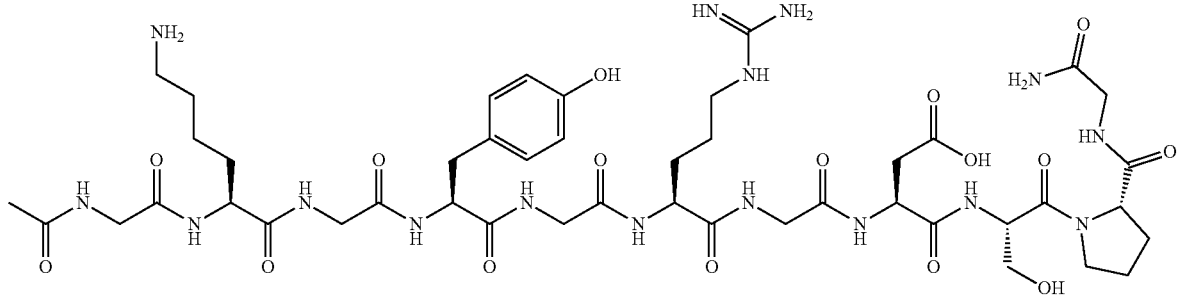 [SMILES: CC(=O)NCC(=O)N[C@@H](CCCCN)C(=O)NCC(=O)N[C@@H](Cc1ccc(O)cc1)C(=O)NCC(=O)N[C@@H](CCCNC(=N)N)C(=O)NCC(=O)N[C@@H](CC(=O)O)C(=O)N[C@@H](CO)C(=O)N1CCC[C@H]1C(=O)NCC(N)=O]

A cell-adhesive peptide with sequence of GKGYGRGD-SPG was prepared on a PS3 peptide synthesizer (Protein technologies Tucson, Ariz.) using the Rink Amide resin (EMD Millipore, Ill.) following standard Fmoc solid phase peptide synthesis protocols. The Rink Amide-MBNA resin (0.25 mmol) was swollen in DMF for 15 minutes on the peptide synthesizer before the Fmoc group was removed by a piperidine/DMF solution (20 vol %). After the resin was thoroughly washed with DMF, a 4-fold excess of Fmoc-protected amino acid (1.0 mmol) HBTU (379 mg, 1.0 mmol) and 4-methylmorpholine DMF solution were added to the reaction vessel for standard amine-carboxylic acid coupling. A coupling time of 1 hour was used for all the amino acids. After each coupling step, excess reactants were washed off using DMF, and the Fmoc group was removed before the addition of the next residue. At the end of the peptide synthesis, the amine group at the N-terminus was acetylated with acetic anhydride (5 mL, 20% in DMF, with 0.3 mL DIPEA) for 20 min. The peptide was cleaved and deprotected in TFA/H$_2$O/triisopropylsilane (95/2.5/2.5, v/v) for 3 hours and precipitated in cold diethyl ether, leaving and amide functionality at the C-terminus of the peptide product. HPLC purification followed by lyophilization afforded the title compound as dry powder.

RGD Peptide (42 mg, 38.5 μmol) was dissolved in 550 μL of anhydrous DMF and N,N-diisopropylethylamine (17 μL, 97.6 μmol) was added followed by (1R,8S,9R,4E)-bicyclo[6.1.0]non-4-en-9-ylmethyl(4-nitrophenyl) carbonate[1] (18 mg, 56.7 μmol). The reaction was stirred at room temperature for 3 hours. The resulting solution was added dropwise to 35 mL of diethyl ether. The crude product was obtained by precipitation followed by centrifugation (5,000 rpm, 5 minutes). The precipitation/centrifugation procedure was repeated two additional times and then the crude product was purified by HPLC using a gradient of 5% to 95% acetonitrile in pH neutral water (i.e. without TFA or formic acid modifier). Collected fractions were lyophilized and stored in −20° C. freezer. HPLC purification afforded 39 mg of sTCO-RGD conjugate (30.8 μmol, 80%).f

DHTz Drug Release

Intermolecular Diels-Alder/aromatization sequence between 3,6-di(pyridin-2-yl)-1,2,4,5-tetrazine and vinyl diethylcarbamate

RGD-sTCO

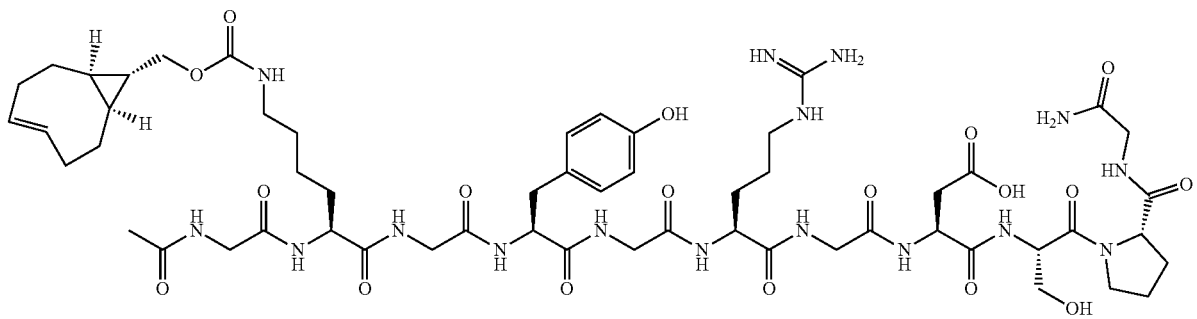

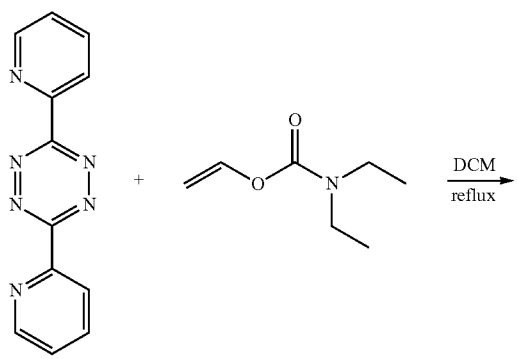

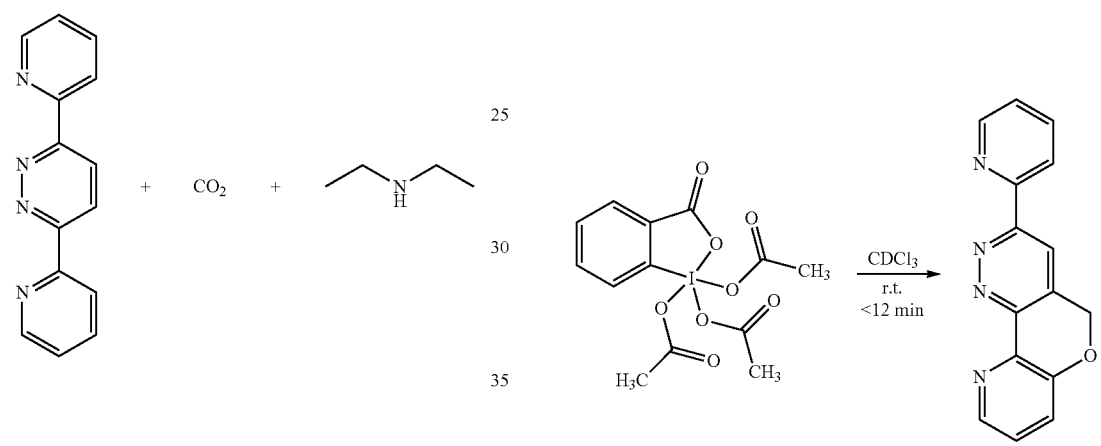

Dess-Martin periodinane oxidation and Intramolecular Diels-Alder/Aromatization Sequence: 3-(pyridin-2-yl)-5H-pyrido[2',3':5,6]pyrano[4,3-c]pyridazine

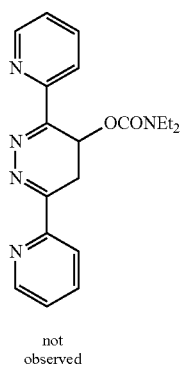

not observed

In a typical experiment, vinyl diethylcarbamate (60.0 mg, 0.420 mmol, 5.00 equiv) and 3,6-di(pyridin-2-yl)-1,2,4,5-tetrazine and vinyl diethylcarbamate (20.0 mg, 0.0846 mmol, 1.00 equiv) were dissolved in 2 mL CD$_3$OD. The reaction was stirred at room temperature for 48 hours, after which $^1$H NMR was taken. Diethyl amine (36% NMR yield) was released and shown on NMR. Aromatization product was also present on NMR.

NMR experiment: A typical Dess-Martin oxidation and intramolecular Diels-Alder/aromatization reaction sequence was performed in CDCl$_3$ and $^1$H NMR. Thus, 3-(3-(allyloxy)pyridin-2-yl)-6-(pyridin-2-yl)-1,4-dihydro-1,2,4,5-tetrazine (10.3 mg, 0.034 mmol, 1.00 equiv) was dissolved in 1 mL CDCl$_3$ in a 7 mL vial. Dess-Martin periodinane (22.2 mg, 0.051 mmol, 1.50 equiv) was added to the reaction. The mixture was stirred at room temperature for 3 min. The mixture was then transferred to a NMR tube and $^1$H NMR experiment was performed quickly. The overall time duration (from the beginning of reaction to final NMR spectrum) was 12 minutes. No alkene peak of 3-(3-(allyloxy)pyridin-2-yl)-6-(pyridin-2-yl)-1,4-dihydro-1,2,4,5-tetrazine was shown on proton NMR, indicating the intramolecular Diels-Alder was finished.

Preparative experiment: Dess-Martin periodinane (30.0 mg, 0.0707 mmol, 2.00 equiv.) was added to a DCM 4.00 mL solution of 3-(3-(allyloxy)pyridin-2-yl)-6-(pyridin-2-yl)-1,4-dihydro-1,2,4,5-tetrazine (10.4 mg, 0.0353 mmol, 1.00 equiv). After 30 min, the reaction mixture was quenched with 10 mL NaHCO$_3$ (sat.) and 10 mL DCM. The aqueous layer was extract with 10 mL DCM three times. The organic layers were combined, dried over MgSO$_4$ and concentrated via rotary evaporator. Purification by flash chromatography (1%-2% methanol/dcm) gave 3-(pyridin-2-yl)-5H-pyrido[2',3':5,6]pyrano[4,3-c]pyridazine (9.00 mg, 97%) as a white solid.

UV-Vis experiment with HRP and 3-((2-(6-(pyridin-2-yl)-1,4-dihydro-1,2,4,5-tetrazin-3-yl)pyridin-3-yl)oxy)prop-1-en-2-yl diethylcarbamate

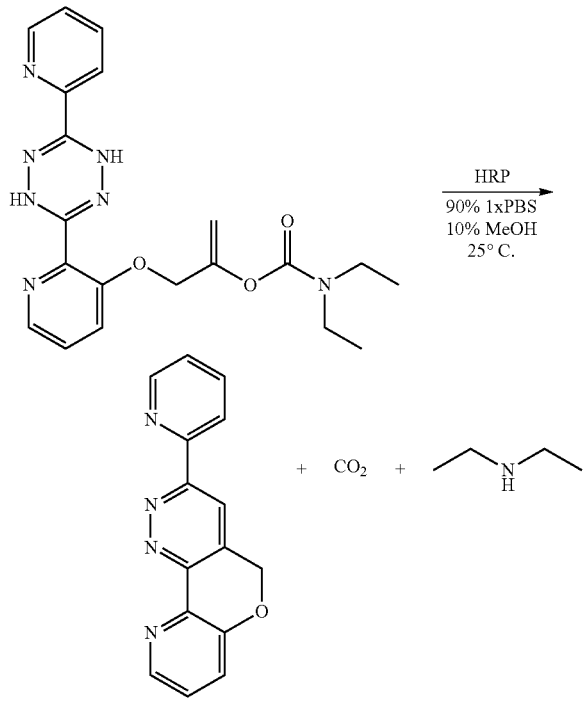

50 µM 3-((2-(6-(pyridin-2-yl)-1,4-dihydro-1,2,4,5-tetrazin-3-yl)pyridin-3-yl)oxy) prop-1-en-2-yl diethylcarbamate (in 90% 1xPBS, 10% MeOH, no EDTA, 25 degree) was mixed with 15 µL HRP (2.06 µM). The reaction was monitored by UV-Vis over 60 min. Aromatized product was formed eventually.

Synthesis Procedure for Dihydrotetrazine Substrates: N-(tert-butyl)-3-methylpicolinamide

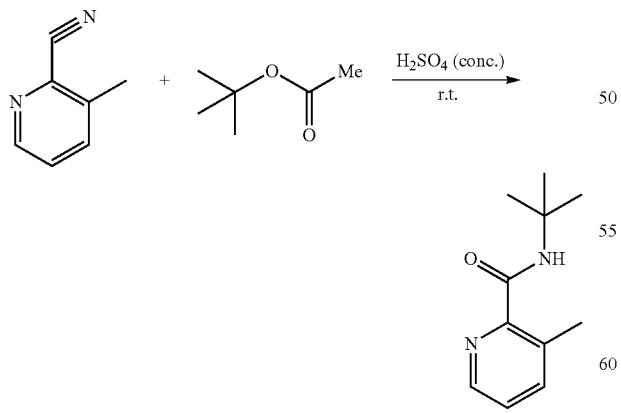

To a solution of 2-cyano-3-methylpyridine (1.20 g, 12.0 mmol) in tert-butyl acetate (10.0 mL) was added concentrated $H_2SO_4$ (1.00 mL), and the mixture was stirred at room temperature overnight before it was diluted with water. The mixture was then carefully neutralized by adding $NH_4OH$ at 0° C. and then extracted twice with 1:1 hexane-EtOAc. The combined organics were washed with saturated brine, dried ($Na_2SO_4$), filtered, and concentrated. The residue was chromatographed on silica gel to give N-(tert-butyl)-3-methylpicolinamide (1.85 g, 95%) as a colorless solid.

3-(but-3-en-1-yl)-N-(tert-butyl)picolinamide

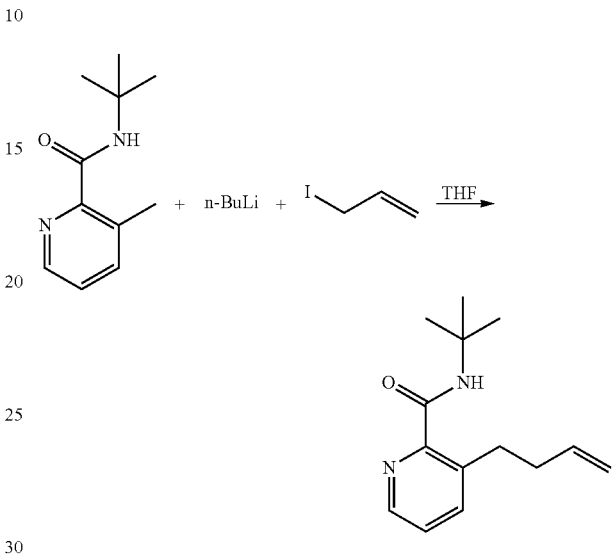

N-(tert-butyl)-3-methylpicolinamide (1.45 g, 7.54 mmol, 1.00 equiv.) was dissolved in 29.0 mL dry THF. The solution was chilled to −40° C. nBuLi (6.03 mL 15.08 mmol, 2.00 equiv., 2.50 M in) was added dropwise to the solution at −40° C. The reaction was stirred at −40° C. for 10 min. Allyl iodide was added to the reaction dropwise. The reaction mixture was further stirred for 30 min, during which time the solution was allowed to be warmed up to room temperature. The reaction was then quenched with 2.00 mL water. THF was removed via rotary evaporator. The reaction mixture was diluted with 30 mL Brine and 30 mL ethyl acetate. The aqueous layer was extracted with 30 mL ethyl acetate three times. The organic layers were combined, dried over $MgSO_4$ and concentrated. Purification by flash chromatography (5% ethyl acetate/hexane) gave 3-(but-3-en-1-yl)-N-(tert-butyl)picolinamide (1.49 g, 85%) as a yellow oil.

3-(but-3-en-1-yl)picolinonitrile

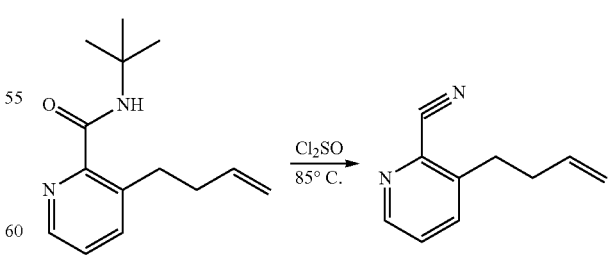

A mixture of 3-(but-3-en-1-yl)-N-(tert-butyl)picolinamide (1.00 g, 4.06 mmol, 1.00 equiv) and thionyl chloride (10.0 mL 138 mmol, 34.0 equiv.) was heated at 85° C. for 3 hours. The mixture was then cooled down to room temperature. Excess amount of thionyl chloride was removed via distillation. The mixture was quenched with 10 mL 10% NaOH solution and 10 mL DCM. The aqueous layer was extract with 10 mL DCM for three times. The organic layers were combined, dried over MgSO₄ and concentrated.

Purification by flash chromatography (5%-15% ethyl acetate/hexane) gave 3-(but-3-en-1-yl)picolinonitrile (0.524 g, 75%) as a yellow oil.

3-(3-(but-3-en-1-yl)pyridin-2-yl)-6-(pyridin-2-yl)-1,4-dihydro-1,2,4,5-tetrazine

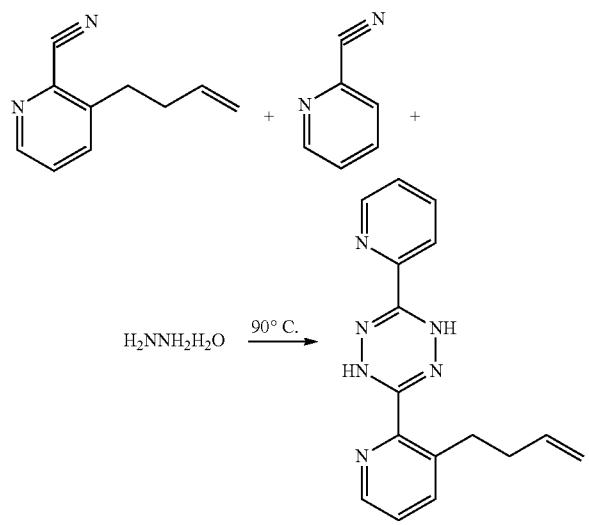

To a 25 mL round bottom flask, 3-(but-3-en-1-yl)picolinonitrile (228 mg, 1.44 mmol, 1.00 equiv.), picolinonitrile (451 mg, 4.33 mmol, 3.00 equiv.) and hydrazine monohydrate (0.564 mL 11.5 mmol, 8.00 equiv.) were added. The reaction mixture was stirred at 90° C. for overnight. After the reaction, 10 mL Brine and 10 mL ethyl acetate were added to the mixture. The aqueous layer was extract with 10 mL ethyl acetate for four times. The organic layers were combined, dried over MgSO₄ and concentrated. Purification by flash chromatography (5% ethyl acetate/hexane) gave 3-(3-(but-3-en-1-yl)pyridin-2-yl)-6-(pyridin-2-yl)-1,4-dihydro-1,2,4,5-tetrazine (84 mg, 20%) as a yellow solid.

3-(allyloxy)picolinonitrile

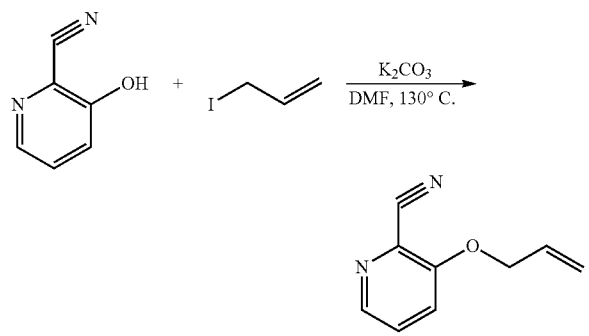

To a stirred DMF (29.5 mL) solution of 3-hydroxypicolinonitrile (500 mg, 4.16 mmol, 1.00 equiv) and potassium carbonate (3.45 g, 24.96 mmol, 6.00 equiv) was added allyl iodide (1.15 mL, 12.5 mmol, 3.00 equiv). The reaction was heated up to 130° C. overnight. The reaction mixture was cooled to room temperature. DMF was removed via high vacuum rotary evaporation. The mixture was diluted with 30 mL Brine and extracted with ethyl acetate (3×30 mL). The organics were combined and dried over MgSO₄, filtered, and concentrated via rotary evaporation. Purification by flash column chromatography (15%-30% ethyl acetate/hexane) afforded the title compound as yellow oil (503 mg, 76% yield).

3-(3-(allyloxy)pyridin-2-yl)-6-(pyridin-2-yl)-1,4-dihydro-1,2,4,5-tetrazine

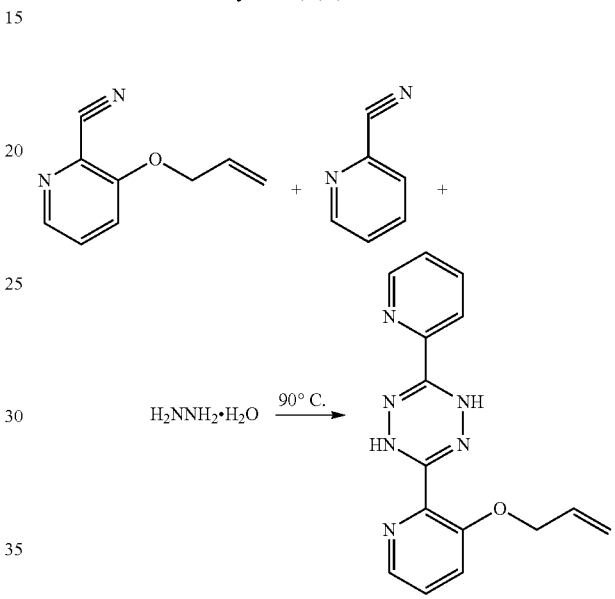

A 10 mL single neck round-bottom flask was charged with 3-(allyloxy)picolinonitrile (200 mg, 1.25 mmol, 1.00 equiv). In a separate flask, 2-cyanopyridine (0.361 mL, 3.74 mmol, 3.00 equiv) was melted by gentle warming, and added to the flask containing 3-(allyloxy)picolinonitrile. Hydrazine hydrate (0.609 mL, 12.5 mmol, 10.00 equiv) was added, and the flask was fitted with reflux condenser and heated to 90° C. overnight under N₂. The reaction mixture was cooled to r.t. and 10 mL Brine was added. The aqueous layer was extract with 3×10 mL ethyl acetate. The organics were combined and dried over MgSO₄, filtered, and concentrated via rotary evaporation. Purification by flash column chromatography (20%-30% ethyl acetate/hexane) afforded the title compound as yellow solid (84.4 mg, 23% yield).

prop-1-en-2-yl diethylcarbamate

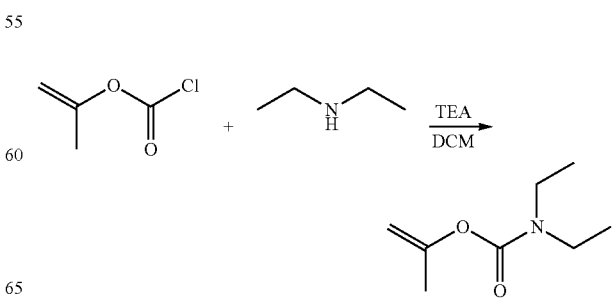

Diethyl amine (1.37 mL, 12.3 mmol, 2.00 equiv) and triethyl amine (2.78 mL, 19.9 mmol, 3.00 equiv) were dissolved in dry DCM (32 mL) and cooled to 0° C. Isopropenyl chloroformate (800 mg, 6.64 mmol, 1.00 equiv) was added dropwise and the reaction mixture was warmed to room temperature. The reaction was allowed to stir overnight. The reaction mixture was quenched with the addition of H$_2$O, DCM and aqueous layers were separated. The aqueous layer also further extract with 2×30 mL DCM. The organics were combined and dried over MgSO$_4$, filtered, and concentrated via rotary evaporation. Purification by flash column chromatography (5% ethyl acetate/hexane) afforded the title compound as colorless oil (950 mg, 91% yield).

3-bromoprop-1-en-2-yl diethylcarbamate

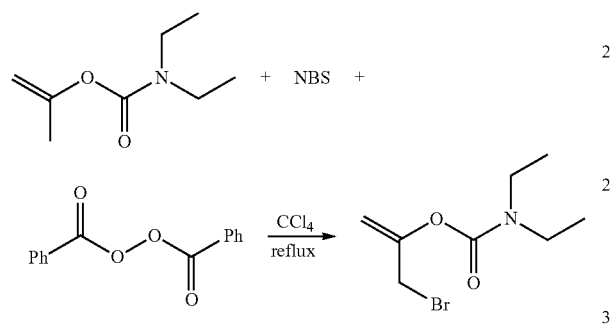

NBS (N-Bromosuccinimide)(543 mg, 3.06 mmol, 1.20 equiv), prop-1-en-2-yl diethylcarbamate (401 mg, 2.54 mmol, 1.00 equiv) and benzoyl peroxide (61.5 mg, 0.254 mmol, 0.100 equiv) were refluxed in dry CCl$_4$ (24 mL) overnight. The reaction was quenched with brine, and the aqueous layer was extract with 2×20 mL ethyl acetate. The organics were combined and dried over MgSO$_4$, filtered, and concentrated via rotary evaporation. Purification by flash column chromatography (5% ethyl acetate/hexane) afforded the title compound as colorless oil (179 mg, 30% yield).

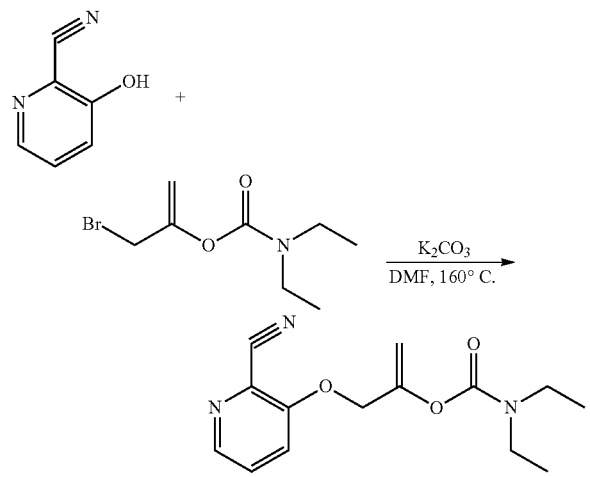

A DMF solution of 3-hydroxypicolinonitrile (281 mg, 2.34 mmol, 2.00 equiv), 3-bromoprop-1-en-2-yl diethylcarbamate (277 mg, 1.17 mmol, 1.00 equiv.) and K$_2$CO$_3$ (970 mg, 7.02 mmol, 6.00 equiv) was refluxed at 160° C. for 15 hours. DMF was removed via a high vacuum rotary evaporator. The mixture was diluted with 20 mL Brine solution and extract with 20 mL ethyl acetate for three times. The organic layers were combined and dried over MgSO$_4$. Purification by flash chromatography (20%-30% ethyl acetate/hexane) gave 3-((2-cyanopyridin-3-yl)oxy)prop-1-en-2-yl diethylcarbamate (123 mg, 38%) as a yellow oil.

3-((2-(6-(pyridin-2-yl)-1,4-dihydro-1,2,4,5-tetrazin-3-yl)pyridin-3-yl)oxy)prop-1-en-2-yl diethylcarbamate

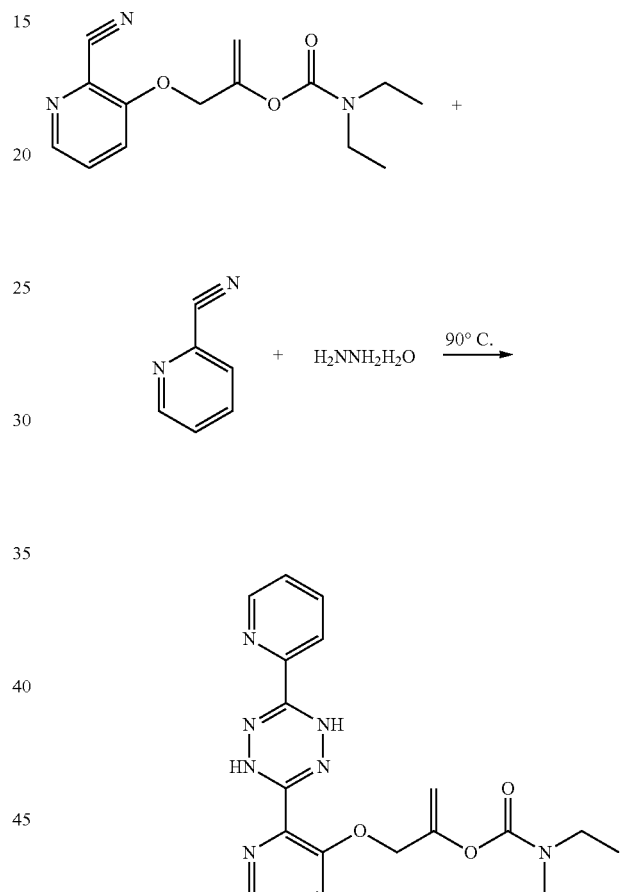

10 mL single neck round-bottom flask was charged with 3-((2-cyanopyridin-3-yl) oxy)prop-1-en-2-yl diethylcarbamate (64.0 mg, 0.232 mmol, 1.00 equiv). In a separate flask, 2-cyanopyridine (0.67 µl, 0.697 mmol, 3.00 equiv) was melted by gentle warming, and added to the flask containing 3-((2-cyanopyridin-3-yl)oxy) prop-1-en-2-yl diethylcarbamate. Hydrazine hydrate (113 µl, 2.32 mmol, 10.0 equiv) was added, and the flask was fitted with reflux condenser and heated to 90° C. overnight under N$_2$. The reaction mixture was cooled to r.t. and 10 mL Brine was added. The aqueous layer was extracted with 3×10 mL ethyl acetate. The organics were combined and dried over MgSO$_4$, filtered, and concentrated via rotary evaporation. Purification by flash column chromatography (10%-15% acetone/hexane) afforded the title compound as yellow oil (14.1 mg, 15% yield).

FeCl₂ Catalyzed Oxidation of a Dihydrotetrazine in the Presence of $H_2O_2$

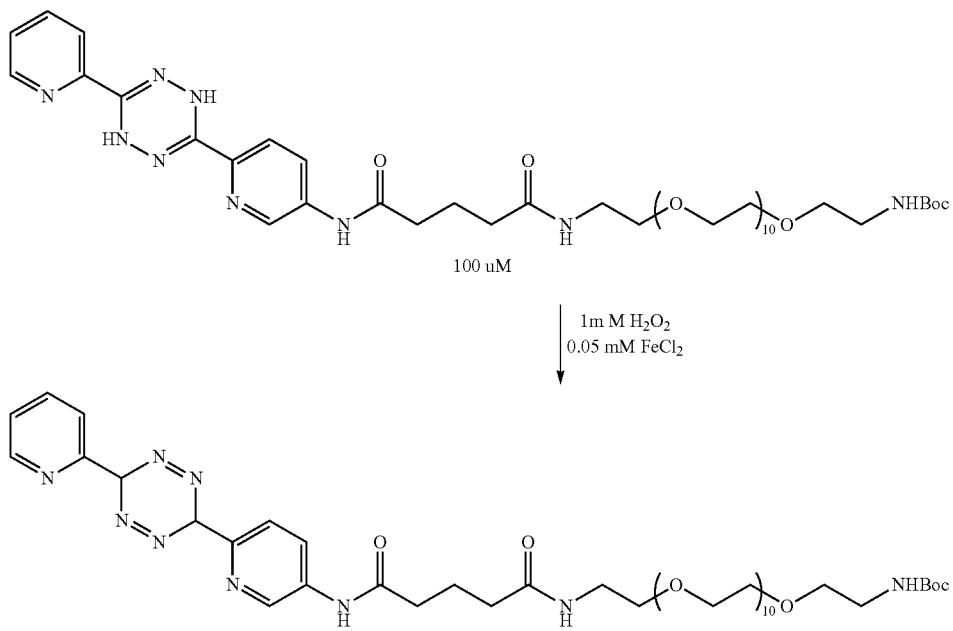

N'-Boc PEG₁₀ dipyridyl-dihydrotetrazine was dissolved in deionized water containing 1 mM $H_2O_2$ to give a final DHTz concentration of 100 μM. The UV absorbance at 330 nm wavelength was monitored over 10 min. Then a 5 mM FeCl₂ stock solution was added and mixed quickly to get a final FeCl₂ concentration of 0.05 mM, followed by continuous monitoring of UV absorbance at 330 nm over 10 min. Oxidation was rapid and complete within ~1 minute.

3-(methylamino)picolinonitrile

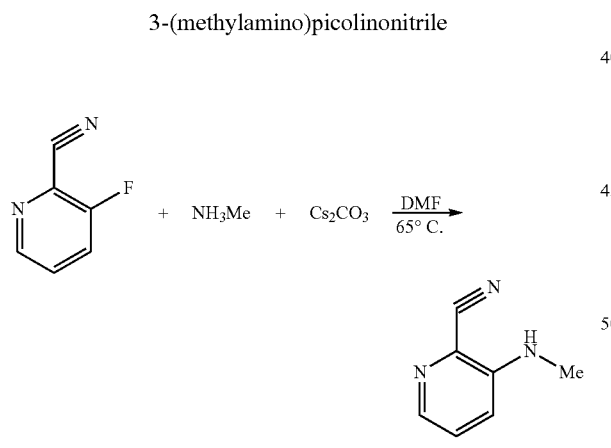

To a solution of 2-cyano-3-fluoropyridine (200 mg, 1.64 mmol, 1.00 equiv) in 5.12 mL DMF were added cesium carbonate (640 mg, 1.97 mmol, 1.20 equiv.) and methylamine (1.97 mL, 3.94 mmol, 2.0M in THF, 2.4 equiv.). The reaction mixture was stirred at 65° C. overnight. After the reaction, DMF was removed via a high vacuum rotary evaporator. The mixture was diluted with 15 mL Brine solution and extract with 15 mL ethyl acetate for three times. The organic layers were combined and dried over MgSO₄. Purification by flash chromatography(35% EA/Hexane) gave 3-(methylamino)picolinonitrile (211 mg, 97%) as a white solid.

6-(6-(3-(methylamino)pyridin-2-yl)-1,4-dihydro-1,2,4,5-tetrazin-3-yl)pyridin-3-ol

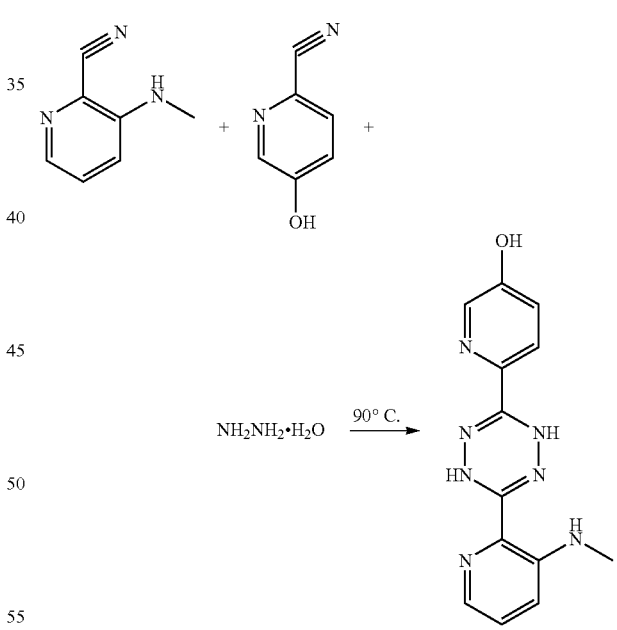

To a 25 mL round bottom flask, 5-hydroxypicolinonitrile (565 mg, 4.70 mmol, 3.00 equiv.), 3-(methylamino)picolinonitrile (206 mg, 1.57 mmol, 1.00 equiv.) and hydrazine monohydrate (1.54 mL, 31.4 mmol, 20.0 equiv.) were added. The reaction mixture was stirred at 90° C. for 24 hours. After the reaction, 20 mL Brine and 20 mL ethyl acetate were added to the mixture. The aqueous layer was extract with 20 mL ethyl acetate for three times. The organic layers were combined, dried over MgSO₄ and concentrated. Purification by flash chromatography(30%-45% EA/Hexane) gave 6-(6-(3-(methylamino)pyridin-2-yl)-1,4-dihydro-1,2,4,5-tetrazin-3-yl)pyridin-3-ol (125 mg, 29%) as a yellow solid.

2-(6-(5-(2,5,8,11,14,17,20,23-octaoxapentacosan-25-yloxy)pyridin-2-yl)-1,4-dihydro-1,2,4,5-tetrazin-3-yl)-N-methylpyridin-3-amine
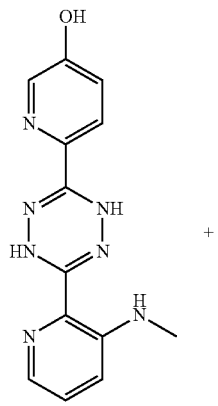
+
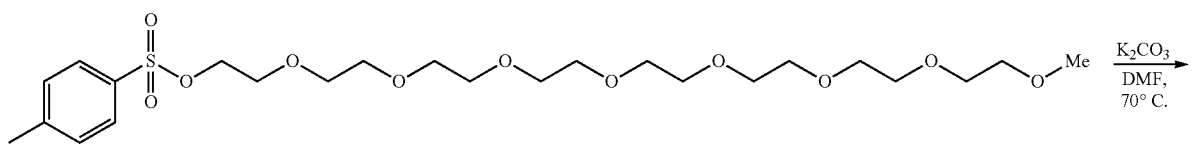
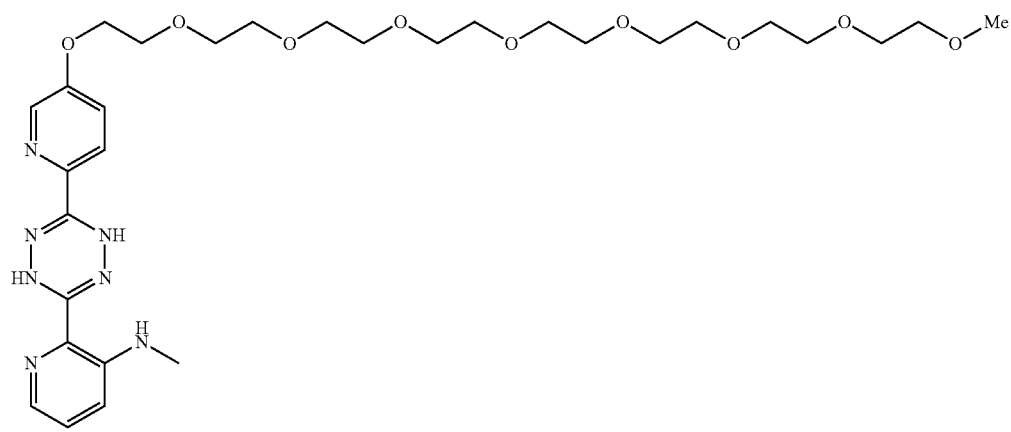

To a DMF (0.700 mL) solution of 6-(6-(3-(methylamino)pyridin-2-yl)-1,4-dihydro-1,2,4,5-tetrazin-3-yl)pyridin-3-ol (20.0 mg, 0.0706 mmol, 1.00 equiv.) and methyl-PEG9-toslate (57.0 mg, 0.106 mmol, 1.50 equiv.) was added potassium carbonate (19.6 mg, 0.142 mmol, 2.00 equiv). The reaction was stirred at 70° C. for 2 hours. After the reaction, DMF was removed via a high vacuum rotary evaporator. The mixture was diluted with 10 mL Brine solution and extract with 10 mL ethyl acetate for three times. The organic layers were combined and dried over MgSO$_4$. Purification by flash chromatography (1% methanol/DCM) gave 2-(6-(5-(2,5,8,11,14,17,20,23-octaoxapentacosan-25-yloxy)pyridin-2-yl)-1,4-dihydro-1,2,4,5-tetrazin-3-yl)-N-methylpyridin-3-amine (27.5 mg, 60%) as a yellow oil.

(E)-N-(2-(6-(5-(2,5,8,11,14,17,20,23-octaoxapentacosan-25-yloxy)pyridin-2-yl)-1,4-dihydro-1,2,4,5-tetrazin-3-yl)pyridin-3-yl)-3-(4-(bis(2-chloroethyl)amino)phenoxy)-N-methylacrylamide

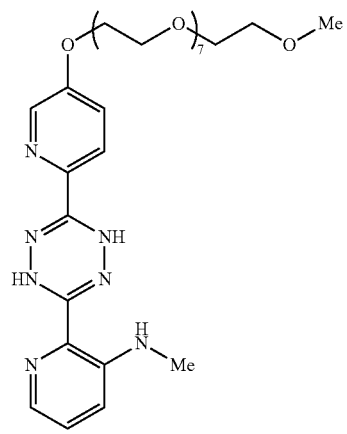

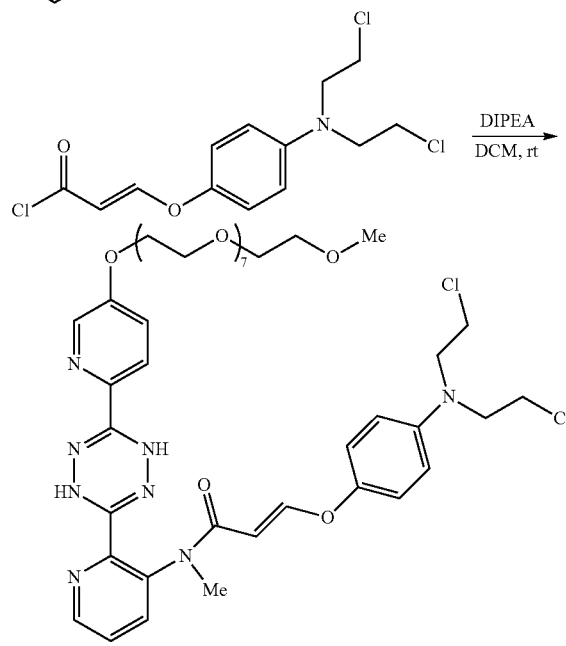

To a flame-dried 10 mL flask containing (E)-3-(4-(bis(2-chloroethyl)amino)phenoxy)acryloyl chloride (52.0 mg, 0.160 mmol, 3.00 equiv.), a dry DCM (0.530 mL) solution of 2-(6-(5-(2,5,8,11,14,17,20,23-octaoxapentacosan-25-yloxy) pyridin-2-yl)-1,4-dihydro-1,2,4,5-tetrazin-3-yl)-N-methylpyridin-3-amine (34.6 mg, 0.0530 mmol, 1.00 equiv.) and DIPEA (41.3 mg, 0.32 mmol, 6.00 equiv.) was added. The reaction mixture was stirred at room temperature for 3 hours. After the reaction, DCM was removed via rotary evaporator. Purification by flash chromatography (40%-60% acetone/hexane) gave (E)-N-(2-(6-(5-(2,5,8,11,14,17,20,23-octaoxapentacosan-25-yloxy)pyridin-2-yl)-1,4-dihydro-1,2,4,5-tetrazin-3-yl) pyridin-3-yl)-3-(4-(bis(2-chloroethyl)amino)phenoxy)-N-methylacrylamide (18.2 mg, 37%) as a yellow oil.

3-(5-(2,5,8,11,14,17,20,23-octaoxapentacosan-25-yloxy)pyridin-2-yl)-6-methylpyridazino[4,3-c][1,5]naphthyridin-5(6H)-one

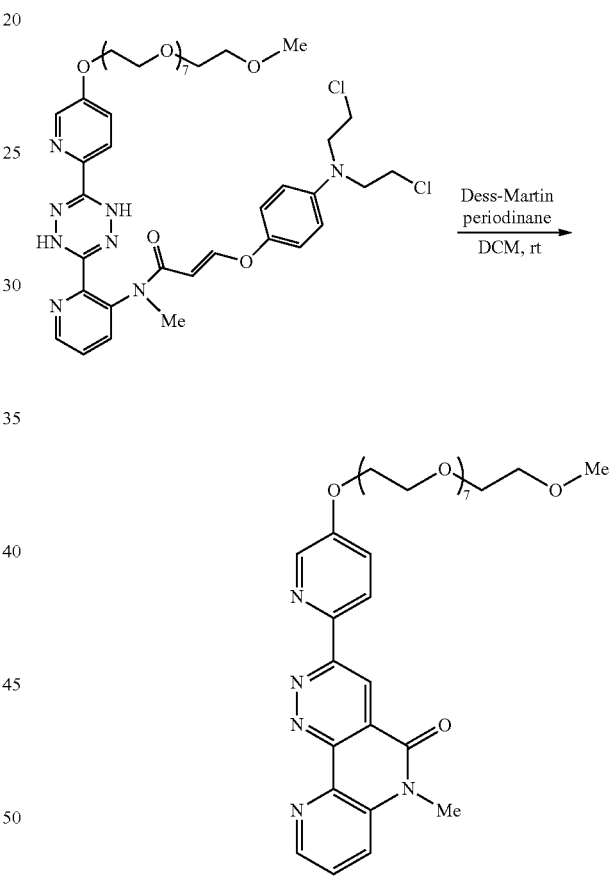

To a dry DCM (1.00 mL) solution of (E)-N-(2-(6-(5-(2,5,8,11,14,17,20,23-octaoxapentacosan-25-yloxy)pyridin-2-yl)-1,4-dihydro-1,2,4,5-tetrazin-3-yl) pyridin-3-yl)-3-(4-(bis(2-chloroethyl)amino)phenoxy)-N-methylacrylamide (11.1 mg, 0.0119 mmol, 1.00 equiv.) was added Dess-Martin periodinane (10.3 mg, 0.0242 mmol, 2.00 equiv). The reaction mixture was stirred at room temperature for 1 hour. After reaction, DCM was removed via rotary evaporator. Purification by flash chromatography (50% acetone/hexane, then 5% methanol/dcm) gave 3-(5-(2,5,8,11,14,17,20,23-octaoxapentacosan-25-yloxy)pyridin-2-yl)-6-methylpyridazino[4,3-c][1,5]naphthyridin-5(6H)-one (4.6 mg, 58%) as a yellow oil.

4-(bis(2-chloroethyl)amino)phenol

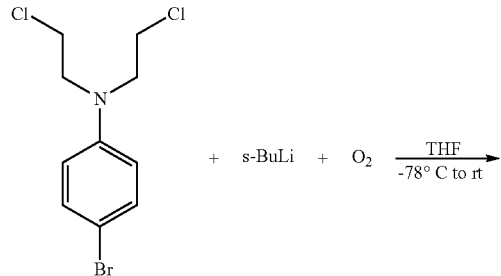

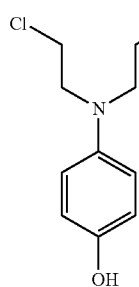

4-Bromo-N,N-bis(2-chloroethyl)aniline was prepared from ((4-bromophenyl) azanediyl)bis(ethane-2,1-diyl) dimethanesulfonate following the procedure previously described (*J. Med. Chem.* 2014, 4498).

4-Bromo-N,N-bis(2-chloroethyl)aniline (200 mg, 0.670 mmol, 1.00 equiv.) was dissolved in 6.70 mL dry THF. The solution was chilled to −78 C. After 10 min, 1.00 mL s-BuLi (1.35 mmol, 2.00 equiv, 1.40 M in cyclohexane) was added to the THF solution dropwise. The reaction was stirred at −78° C. for 20 min. Oxygen was then sparged into the reaction solution for 30 min at −78° C. Oxygen was sparged for another 30 min, during which time the reaction was allowed to warm up to 0° C. The reaction mixture was then stirred at room temperature for one hour. After the reaction, THF was removed via rotary evaporator. The mixture was diluted with 20 mL Brine and 20 mL ethyl acetate. The aqueous layer was extract with 20 mL ethyl acetate for three times. The organic layers were combined, dried over MgSO$_4$ and concentrated. Purification by flash chromatography (10%-15% ethyl acetate/hexane) gave 4-(bis(2-chloroethyl) amino)phenol (55.0 mg, 35%) as a colorless oil.

(E)-methyl 3-(4-(bis(2-chloroethyl)amino)phenoxy) acrylate

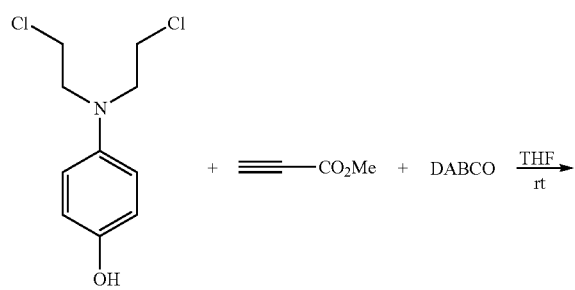

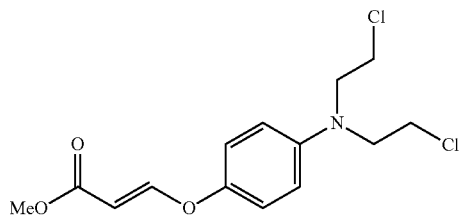

To a stirred solution of 1,4 diazabicyclo[2,2,2] octane (12.8 mg, 0.114 mmol, 0.100 equiv.) and 4-(bis(2-chloroethyl)amino)phenol (265 mg, 1.14 mmol, 1.00 equiv.) in 0.700 mL dry THF at room temperature was added methyl propiolate (111 μl, 1.25 mmol, 1.10 equiv) dropwise. The reaction mixture was stirred overnight at room temperature. After reaction, THF was removed via rotary evaporator. Sodium hydroxide (10% solution, 10 mL) was added and the aqueous was extracted with 10 mL DCM for three times. The organic layers were combined, dried over MgSO$_4$, and concentrated. Purification by flash chromatography (5%-10% ethyl acetate/hexane) gave (E)-methyl 3-(4-(bis(2-chloroethyl)amino)phenoxy)acrylate (276 mg, 76%) as a white solid.

(E)-3-(4-(bis(2-chloroethyl)amino)phenoxy)acrylic Acid

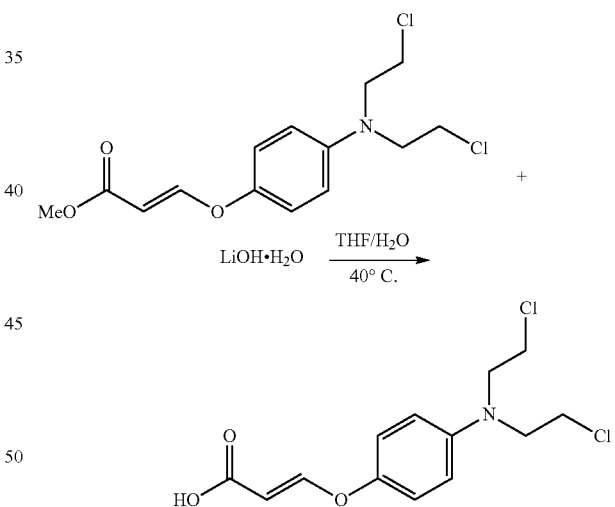

LiOH.H$_2$O (80.0 mg, 1.91 mmol, 2.00 equiv.) was added to 10.4 mL THF/H$_2$O (3:1) solution of (E)-methyl 3-(4-(bis (2-chloroethyl)amino)phenoxy)acrylate (304 mg, 0.950 mmol, 1.00 equiv.). The reaction was stirred at 40° C. for 72 hours. After reaction, the solution was neutralized to pH=7 with 1.0 M HCl. The mixture was diluted with 20 mL Brine and 20 mL ethyl acetate. The aqueous layer was extract with 20 mL ethyl acetate for three times. The organic layers were combined, dried over MgSO$_4$ and concentrated. Purification by flash chromatography (30% ethyl acetate/hexane) gave (E)-3-(4-(bis (2-chloroethyl)amino)phenoxy)acrylic acid (154 mg, 50%) as a colorless solid.

(E)-3-(4-(bis(2-chloroethyl)amino)phenoxy)acryloyl chloride

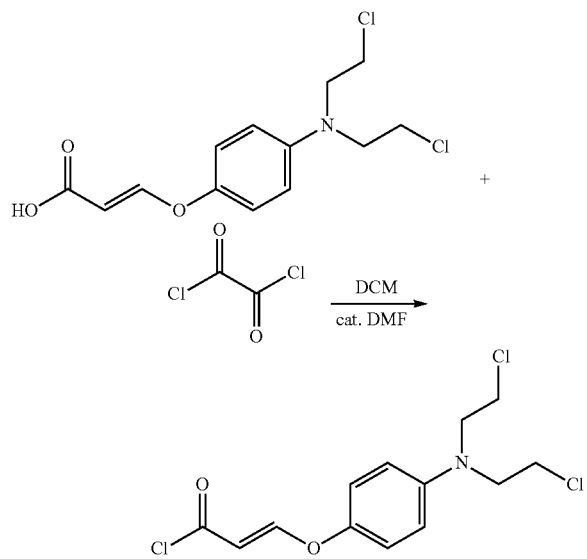

To a dry DCM (11.53 mL) solution of (E)-3-(4-(bis(2-chloroethyl)amino)phenoxy)acrylic acid (141 mg, 0.460 mmol, 1.00 equiv.) was added oxalyl chloride (59.0 µl, 0.700 mmol, 1.50 equiv.) at 0° C. One drop of dry DMF was added to the reaction mixture. The reaction was stirred at room temperature for 1.5 hours. After reaction, the mixture was concentrated via rotary evaporator to give (E)-3-(4-(bis(2-chloroethyl) amino)phenoxy)acryloyl chloride (236 mg, 90%) as a pale green solid, which was used in the next step without further purification.

3-(butylamino)picolinonitrile

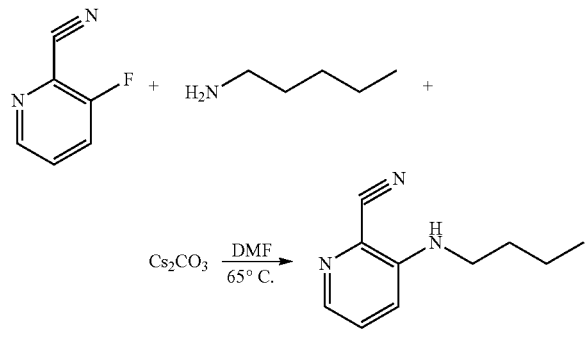

To a solution of 2-cyano-3-fluoropyridine (200 mg, 1.64 mmol, 1.00 equiv) in 5.10 mL DMF were added cesium carbonate (640 mg, 1.97 mmol, 1.20 equiv.) and butylamine (0.195 mL, 1.97 mmol, 1.20 equiv.). The reaction mixture was stirred at 65° C. overnight. After the reaction, DMF was removed via a high vacuum rotary evaporator. The mixture was diluted with 15 mL Brine solution and extract with 15 mL ethyl acetate for three times. The organic layers were combined and dried over MgSO₄. Purification by flash chromatography (20% EA/Hexane) gave 3-(butylamino) picolinonitrile (257 mg, 90%) as a colorless oil.

N-butyl-2-(6-(pyridin-2-yl)-1,4-dihydro-1,2,4,5-tetrazin-3-yl)pyridin-3-amine

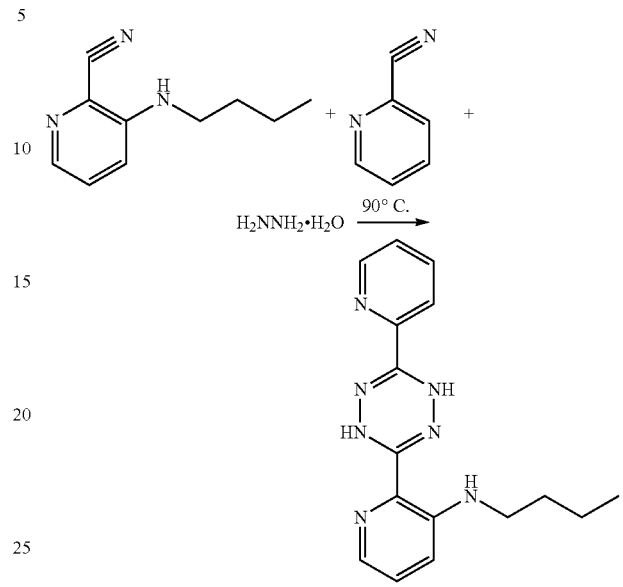

To a 25 mL round bottom flask, 3-(butylamino)picolinonitrile (200 mg, 1.14 mmol, 1.00 equiv.), picolinonitrile (297 mg, 2.85 mmol, 2.50 equiv.) and hydrazine monohydrate (0.445 mL 9.13 mmol, 8.00 equiv.) were added. The reaction mixture was stirred at 90° C. for 24 hours. After the reaction, 10 mL Brine and 10 mL ethyl acetate were added to the mixture. The aqueous layer was extract with 10 mL ethyl acetate for four times. The organic layers were combined, dried over MgSO₄ and concentrated. Purification by flash chromatography(5%-10% EA/Hexane) gave N-butyl-2-(6-(pyridin-2-yl)-1,4-dihydro-1,2,4,5-tetrazin-3-yl)pyridin-3-amine (64.8 mg, 17%) as a yellow solid.

(E)-methyl 3-(4-nitrophenoxy)acrylate

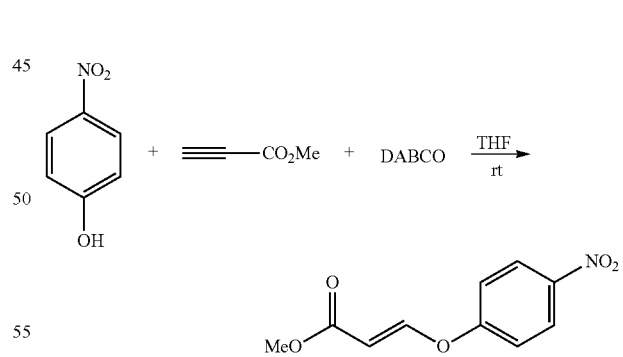

To a stirred solution of 1,4 diazabicyclo[2,2,2] octane (269 mg, 2.40 mmol, 0.100 equiv.) and 4-nitrophenol (3.62 g, 26.0 mmol, 1.10 equiv.) in 15 mL dry THF at room temperature was added methyl propiolate (2.14 mL, 24.0 mmol, 1.00 equiv) dropwise. The reaction mixture was stirred overnight at room temperature. After reaction, THF was removed via rotary evaporator. Sodium hydroxide (10% solution, 100 mL) was added and the aqueous was extracted with 100 mL DCM for three times. The organic layers were combined, dried over MgSO₄, and concentrated. Purification by flash chromatography (5%40% ethyl acetate/hexane) gave (E)-methyl 3-(4-nitrophenoxy) acrylate (4.82 g, 90%) as a white solid.

(E)-3-(4-nitrophenoxy)acrylic Acid

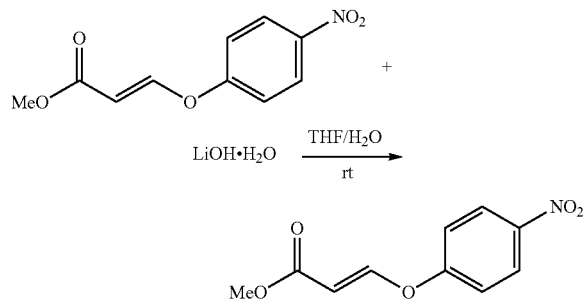

LiOH.H₂O (2.10 g, 50.0 mmol, 2.00 equiv.) was added to 272 mL THF/H₂O (3:1) solution of (E)-methyl 3-(4-nitrophenoxy)acrylate (5.78 g, 25.0 mmol, 1.00 equiv.). The reaction was stirred at room temperature overnight. After reaction, the solution was acidified to pH=3.0 with 1.0 M HCl. The mixture was diluted with 100 mL Brine and 100 mL ethyl acetate. The aqueous layer was extract with 100 mL diethyl ether for three times. The organic layers were combined, dried over MgSO₄ and concentrated. Purification by flash chromatography (1% methanol/dcm) gave (E)-3-(4-(bis(2-chloroethyl) amino)phenoxy)acrylic acid (4.90 g, 90%) as a white solid.

(E)-3-(4-nitrophenoxy)acryloyl Chloride

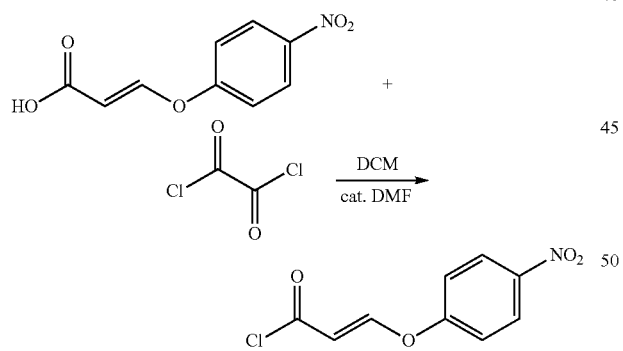

To a dry DCM (4.70 mL) solution of (E)-3-(4-(bis(2-chloroethyl)amino)phenoxy)acrylic acid (300 mg, 1.43 mmol, 1.00 equiv.) was added oxalyl chloride (0.388 mL, 4.59 mmol, 3.20 equiv.) at 0° C. One drop of dry DMF was added to the reaction mixture. The reaction was stirred at room temperature for 4 hours. After reaction, the mixture was concentrated via rotary evaporator to give (E)-3-(4-nitrophenoxy)acryloyl chloride (300 mg, 92%) as a pale yellow solid, which was used in the next step without further purification.

(E)-N-butyl-3-(4-nitrophenoxy)-N-(2-(6-(pyridin-2-yl)-1,4-dihydro-1,2,4,5-tetrazin-3-yl)pyridin-3-yl) acrylamide

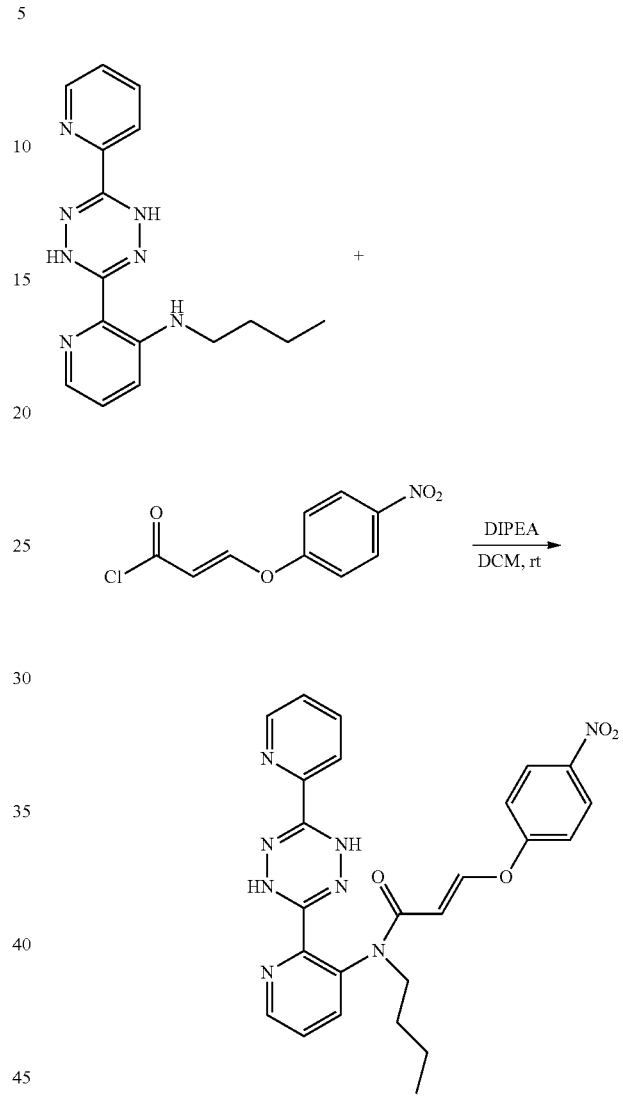

A 10 mL flame-dried flask was charged with (E)-3-(4-nitrophenoxy)acryloyl chloride (100 mg, 0.440 mmol, 2.44 equiv.). A 0.800 mL DCM (dry) solution of N-butyl-2-(6-(pyridin-2-yl)-1,4-dihydro-1,2,4,5-tetrazin-3-yl)pyridin-3-amine (55.0 mg, 0.180 mmol, 1.00 equiv) was added to the flask in one portion, followed by DIPEA (62.5 µl, 0.376 mmol, 2.09 equiv.). The reaction was stirred at room temperature overnight. The reaction was quenched by 10 mL NaHCO₃ (sat.) and 10 mL ethyl acetate. The aqueous layer was extract with 10 mL ethyl acetate for three times. The organic layers were combined, dried over MgSO₄ and concentrated. Purification by flash chromatography (15%-30% ethyl acetate/hexane) gave (E)-N-butyl-3-(4-nitrophenoxy)-N-(2-(6-(pyridin-2-yl)-1,4-dihydro-1,2,4,5-tetrazin-3-yl)pyridin-3-yl)acrylamide (20.2 mg, 22%) as a yellow solid.

6-butyl-3-(pyridin-2-yl)pyridazino[4,3-c][1,5]naph-thyridin-5(6H)-one

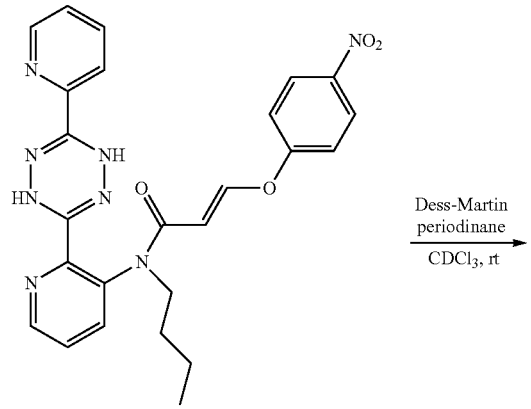

Dess-Martin periodinane (25.6 mg, 0.0604 mmol, 1.50 equiv.) was added to a CDCl₃ 0.500 mL solution of (E)-N-butyl-3-(4-nitrophenoxy)-N-(2-(6-(pyridin-2-yl)-1,4-di-hydro-1,2,4,5-tetrazin-3-yl)pyridin-3-yl)acrylamide (20.2 mg, 0.0420 mmol, 1.00 equiv). The reaction was monitored by NMR. After 20 min, the reaction mixture was concentrated via rotary evaporator. Purification by flash chromatography (50% ethyl acetate/hexane, then 5% methanol/dcm) gave 6-butyl-3-(pyridin-2-yl)pyridazino[4,3-c][1,5] naphthyridin-5(6H)-one (12.9 mg, 97%) as a yellow solid and 4-nitrophenol (4.80 mg, 87%) as colorless solid.

3-((2-hydroxyethyl)amino)picolinonitrile

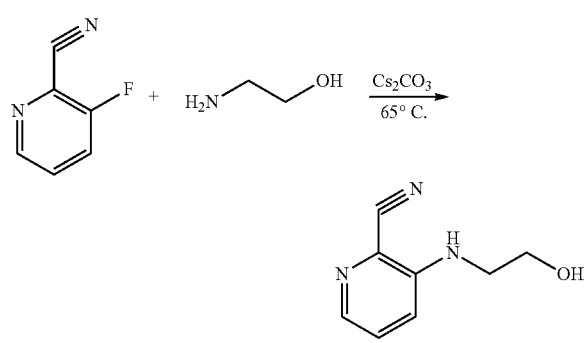

To a solution of 2-cyano-3-fluoropyridine (500 mg, 4.10 mmol, 1.00 equiv) in 12.8 mL DMF were added cesium carbonate (1.60 g, 4.91 mmol, 1.20 equiv.) and ethanolamine (0.295 mL, 4.91 mmol, 1.20 equiv.). The reaction mixture was stirred at 65° C. for 8 hours. After the reaction, DMF was removed via a high vacuum rotary evaporator. The mixture was diluted with 15 mL Brine solution and extract with 15 mL ethyl acetate for three times. The organic layers were combined and dried over MgSO₄. Purification by flash chromatography (1%-5% methanol/dcm) gave 3-((2-hydroxyethyl)amino)picolinonitrile (177 mg, 27%) as a white solid.

2-((2-(6-(pyridin-2-yl)-1,4-dihydro-1,2,4,5-tetrazin-3-yl)pyridin-3-yl)amino)ethanol

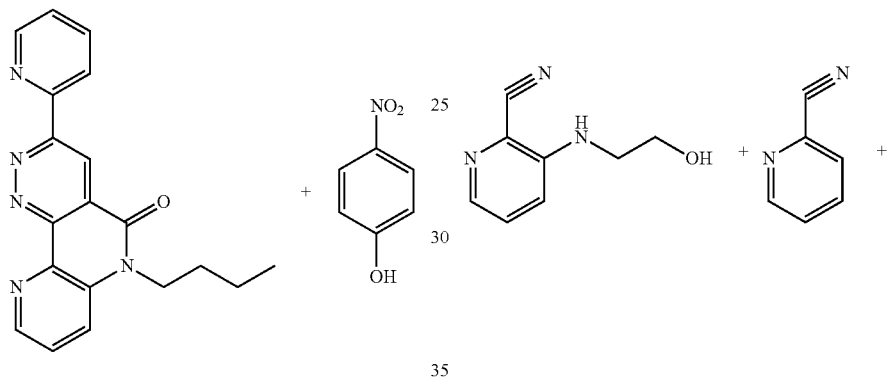

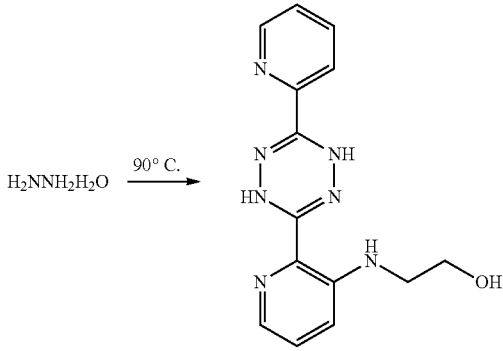

To a 25 mL round bottom flask, 3-((2-hydroxyethyl)amino)picolinonitrile (500 mg, 3.06 mmol, 1.00 equiv.), picolinonitrile (957 mg, 9.19 mmol, 3.00 equiv.) and hydrazine monohydrate (1.50 mL, 30.6 mmol, 10.0 equiv.) were added. The reaction mixture was stirred at 90° C. for overnight. After the reaction, 30 mL Brine and 30 mL ethyl acetate were added to the mixture. The aqueous layer was extract with 30 mL ethyl acetate for four times. The organic layers were combined, dried over MgSO₄ and concentrated. Purification by flash chromatography (15%-50% ethyl acetate/hexane) gave 2-((2-(6-(pyridin-2-yl)-1,4-dihydro-1,2,4,5-tetrazin-3-yl)pyridin-3-yl)amino)ethanol (339 mg, 37%) as a yellow solid.

51

4-nitrophenyl (2-((2-(6-(pyridin-2-yl)-1,2,4,5-tetrazin-3-yl)pyridin-3-yl)amino)ethyl) carbonate

52

2-((2-(6-(pyridin-2-yl)-1,4-dihydro-1,2,4,5-tetrazin-3-yl)pyridin-3-yl)amino)ethyl 2,5,8,11,14,17,20,23,26,29,32,35-dodecaoxaheptatriacontan-37-ylcarbamate

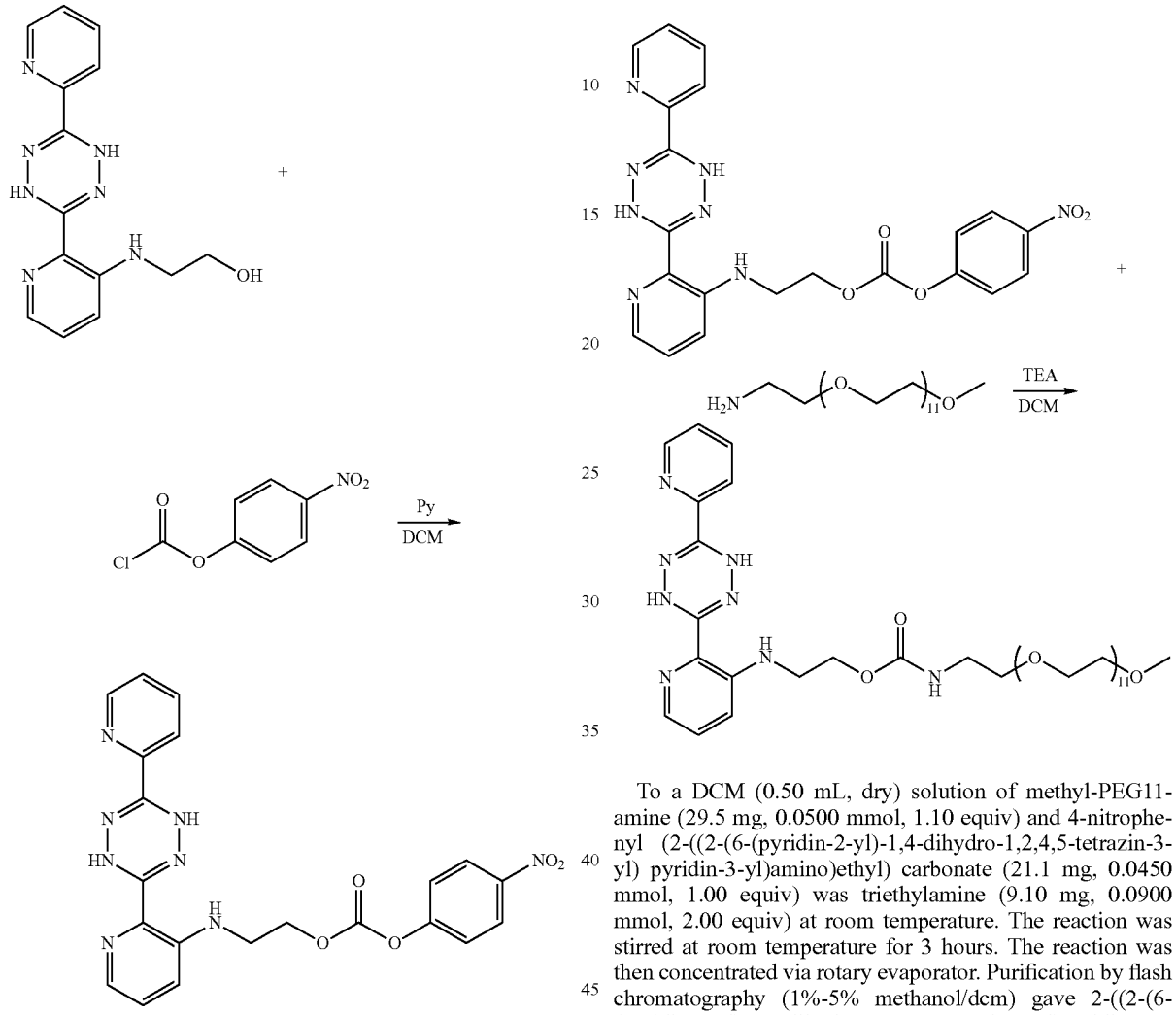

To a DCM (2.20 mL, dry) solution of pyridine (35.3 mg, 0.446 mmol, 2.00 equiv) and 2-((2-(6-(pyridin-2-yl)-1,4-dihydro-1,2,4,5-tetrazin-3-yl)pyridin-3-yl)amino)ethanol (66.3 mg, 0.223 mmol, 1.00 equiv) was added 4-nitrophenyl chloroformate (49.4 mg, 0.245 mmol, 1.10 equiv.) at room temperature. The reaction was stirred at room temperature for 1hour. The reaction was then quenched with 10 mL Brine and 10 mL DCM. The aqueous layer was extract with 10 mL DCM for three times. The organic layers were combined, dried over MgSO₄ and concentrated. Purification by flash chromatography (10%-30% ethyl acetate/hexane) gave 4-nitrophenyl (2-((2-(6-(pyridin-2-yl)-1,4-dihydro-1,2,4,5-tetrazin-3-yl)pyridin-3-yl)amino)ethyl) carbonate (47.6 mg, 46%) as a yellow solid.

To a DCM (0.50 mL, dry) solution of methyl-PEG11-amine (29.5 mg, 0.0500 mmol, 1.10 equiv) and 4-nitrophenyl (2-((2-(6-(pyridin-2-yl)-1,4-dihydro-1,2,4,5-tetrazin-3-yl) pyridin-3-yl)amino)ethyl) carbonate (21.1 mg, 0.0450 mmol, 1.00 equiv) was triethylamine (9.10 mg, 0.0900 mmol, 2.00 equiv) at room temperature. The reaction was stirred at room temperature for 3 hours. The reaction was then concentrated via rotary evaporator. Purification by flash chromatography (1%-5% methanol/dcm) gave 2-((2-(6-(pyridin-2-yl)-1,4-dihydro-1,2,4,5-tetrazin-3-yl)pyridin-3-yl)amino)ethyl 2,5,8,11,14,17,20,23,26,29,32,35-dodecaoxaheptatriacontan-37-ylcarbamate (31.0 mg, 77%) as a yellow oil.

3-((2-cyanopyridin-3-yl)oxy)prop-1-en-2-yl diethylcarbamate 2-pyridinecarboxylic Acid Hydrazide

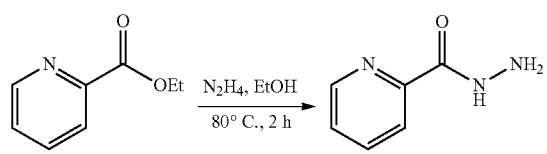 [SMILES: CCOC(=O)c1ccccn1 ; NNC(=O)c1ccccn1]

To a round-bottom flask was added ethyl picolinate (2.5 mL, 18.52 mmol) in ethanol (12 mL) followed by hydrazine monohydrate (1.74 mL, 55.56 mmol). The mixture was refluxed for 2 h. Ethanol was evaporated after reaction mixture cooled down. The light yellow crude product was washed with diethyl ether (15 mL×2). Final product as a white solid (2.3 g, 90%) was collected by vacuum filtration and dried under vacuum. $^1$H NMR (600 MHz, CDCl$_3$) 9.00 (s, 1H), 8.57-8.53 (m, 1H), 8.15 (dd, J=7.8, 1.2 Hz, 1H), 7.85 (td, J=7.7, 1.7 Hz, 1H), 7.44 (ddd, J=7.8, 4.8, 1.2 Hz, 1H), 4.09 (s, 2H); $^{13}$C NMR (100 MHz, CDCl$_3$) 164.84, 149.17, 148.51, 137.47, 126.61, 122.36

N-(carbethoxycarbonyloxy)succinimide

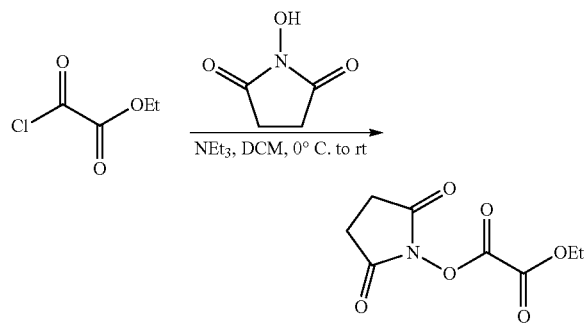

To a dry round-bottom flask was added N-hydroxysuccinimide (2.67 g, 23.27 mmol), anhydrous dichloromethane (10 mL) and trimethylamine (3.24 mL, 23.27 mmol). The mixture was stirred in ice bath for 10 min. Ethyl chlorooxoacetate (2 mL, 17.90 mmol) in anhydrous dichloromethane (20 mL) was added dropwise via syringe pump at 0° C. in 30 min. The mixture was stirred at 0° C. for 30 min, room temperature for 1 h, diluted by dichloromethane (30 mL) and washed by water (20 mL*3). The organic layer was dried with MgSO$_4$, filtered and then solvent was evaporated by rotary evaporator. Crude product (2.85 g, 74%) as light yellow solid was used in the next step without further purification. $^1$H NMR (600 MHz, CDCl$_3$) 4.46 (q, J=7.2 Hz, 1H), 2.90 (s, 2H), 1.43 (t, J=7.2 Hz, 1H); $^{13}$C NMR (100 MHz, CDCl$_3$) 167.89, 154.24, 153.00, 64.76, 25.79, 14.00

Ethyl 2-oxo-2-(2-picolinoylhydrazinyl)acetate

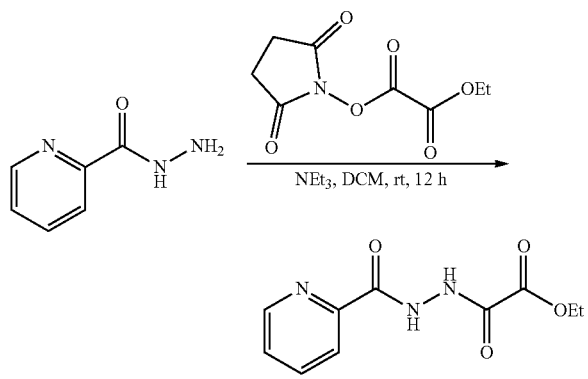

To a dry round-bottom flask was added 2-pyridinecarboxylic acid hydrazide (1.68 g, 12.24 mmol), N-(carbethoxycarbonyloxy)succinimide (2.64 g, 12.24 mmol), triethylamine (2.1 mL, 14.68 mmol) and anhydrous dichloromethane (30 mL). After stirring at room temperature for 12 h, the mixture was diluted by dichloromethane (30 mL) and washed with water (20 mL*3). The organic layer was dried with MgSO$_4$, filtered and evaporated by rotary evaporator. Crude product (2.09 g, 72%) as light yellow solid was used in the next step without further purification. $^1$H NMR (600 MHz, CDCl$_3$) 10.30 (s, 1H), 9.66 (s, 1H), 8.61 (ddd, J=4.8, 1.8, 1.0 Hz, 1H), 8.17 (dt, J=7.9, 1.1 Hz, 1H), 7.89 (td, J=7.7, 1.7 Hz, 1H), 7.51 (ddd, J=7.7, 4.7, 1.2 Hz, 1H), 4.42 (q, J=7.2 Hz, 2H), 1.42 (t, J=7.2 Hz, 3H); $^{13}$C NMR (100 MHz, CDCl$_3$) 160.73, 158.89, 152.58, 148.79, 147.77, 137.64, 127.33, 122.81, 63.78, 14.12

Ethyl 2-chloro-2-((chloro(phenyl)methylene)hydrazono)acetate

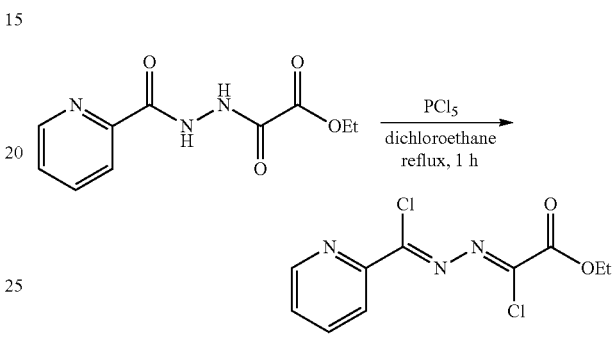

To a dry round-bottom flask was added ethyl 2-oxo-2-(2-picolinoylhydrazinyl)acetate (0.527 g, 2.2 mmol), phosphorous pentachloride (2.3 g, 11.1 mmol) and anhydrous dichloroethane (12 mL). After reflux (85° C.) for 1 h, the mixture was diluted with dichloromethane (50 mL), quenched and washed with cool water (20 mL*3). The organic layer was dried with MgSO$_4$, filtered and evaporated by rotary evaporator. The orange oil-like product (0.15 g, 25%) was collected from column chromatography eluting with hexane/ethyl acetate (7/3). $^1$H NMR (600 MHz, CDCl$_3$) 8.77 (ddd, J=4.8, 1.8, 0.9 Hz, 1H), 8.16 (dt, J=8.0, 1.1 Hz, 1H), 7.84 (td, J=7.8, 1.8 Hz, 1H), 7.46 (ddd, J=7.6, 4.8, 1.2 Hz, 1H), 4.47 (q, J=7.2 Hz, 2H), 1.44 (t, J=7.2 Hz, 3H); $^{13}$C NMR (100 MHz, CDCl$_3$) 158.56, 149.88, 149.84, 142.34, 137.06, 133.74, 126.21, 123.47, 64.28, 14.20

Ethyl 6-(pyridin-2-yl)-1,4-dihydro-1,2,4,5-tetrazine-3-carboxylate

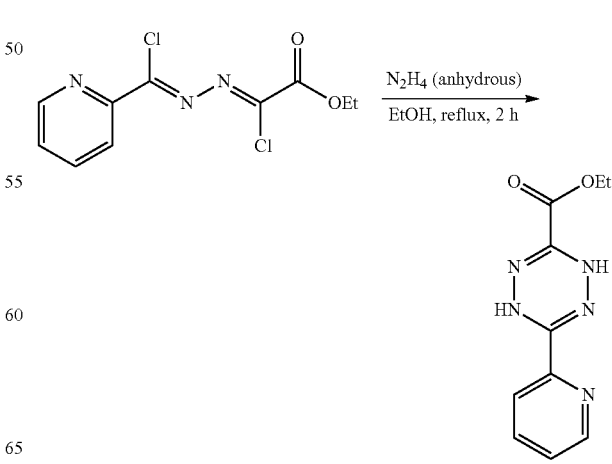

To a dry round-bottom flask was added ethyl 2-chloro-2-((chloro(phenyl)methylene) hydrazono)acetate (0.4 g, 1.46 mmol), anhydrous hydrazine (50 μL, 1.61 mmol) and anhydrous ethanol (6 mL). The mixture was reflux (85° C.) for 2 h and solvent was removed under reduced pressure to yield orange oil like crude product. The crude product was purified by column chromatography loading with dichloromethane and eluting with hexane/ethyl acetate (9/1 to 6/4) to yield yellow solid (0.11 g, 32%). $^1$H NMR (600 MHz, CDCl$_3$) 8.68 (s, 1H), 8.56 (ddd, J=4.9, 1.7, 0.9 Hz, 1H), 7.99 (dt, J=8.0, 1.1 Hz, 1H), 7.76 (td, J=7.8, 1.7 Hz, 1H), 7.40 (s, 1H), 7.37 (ddd, J=7.5, 4.9, 1.2 Hz, 1H), 4.39 (q, J=7.1 Hz, 2H), 1.40 (t, J=7.1 Hz, 4H); $^{13}$C NMR (100 MHz, CDCl$_3$) 159.66, 148.72, 146.73, 145.40, 139.97, 137.10, 125.50, 121.78, 63.26, 14.33 ethyl 6-(pyridin-2-yl)-1,2,4,5-tetrazine-3-carboxylate

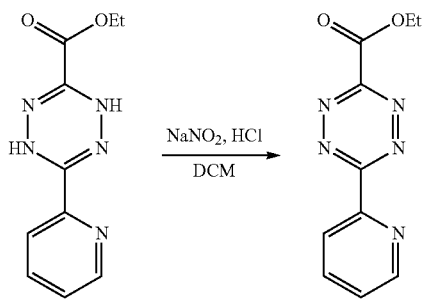 [SMILES: CCOC(=O)C1=NNC(c2ccccn2)=NN1 ; CCOC(=O)c1nnc(-c2ccccn2)nn1]

To a dry round bottom flask was added ethyl 6-(pyridin-2-yl)-1,4-dihydro-1,2,4,5-tetrazine-3-carboxylate (30 mg, 0.129 mmol) and anhydrous dichloromethane (3 mL). To another round bottom flask, connected with the first round bottom flask by needle, was added hydrochloric acid (0.79 mL, 25.73 mmol) and injected nitrogen gas continuously, then sodium nitrite (1.77 g, 25.73 mmol) in water (20 mL) was added by syringe slowly. When pink solution formed in the first round bottom flask, reaction mixture was purified by column chromatography eluting with hexane/ethyl acetate (6/4) to yield pink solid (24 mg, 80.5%). $^1$H NMR (600 MHz, CDCl$_3$) 9.01 (ddd, J=4.7, 1.8, 0.9 Hz, 1H), 8.77 (dt, J=7.9, 1.1 Hz, 1H), 8.04 (td, J=7.8, 1.8 Hz, 1H), 7.62 (ddd, J=7.6, 4.7, 1.2 Hz, 1H), 4.69 (q, J=7.2 Hz, 2H)M 1.54 (t, J=7.2 Hz, 3H); $^{13}$C NMR (100 MHz, CDCl$_3$) 164.42, 160.91, 159.09, 151.48, 149.44, 137.78, 127.38, 125.49, 64.08, 14.32

N,N-bis(2-hydroxyethyl)-6-(pyridin-2-yl)-1,4-dihydro-1,2,4,5-tetrazine-3-carboxamide

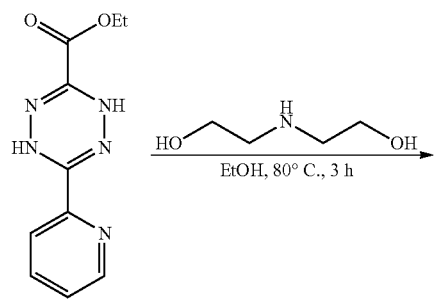

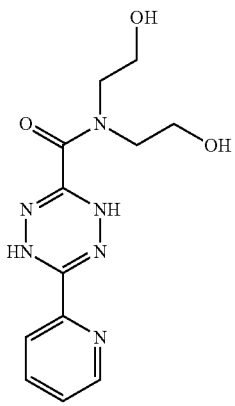

To a dry round bottom flask was added ethyl 6-(pyridin-2-yl)-1,4-dihydro-1,2,4,5-tetrazine-3-carboxylate (29 mg, 0.124 mmol), diethanolamine (36 uL, 0.373 mmol) and anhydrous ethanol (6 mL). After refluxing for 3 h, the mixture was concentrated and purified by column chromatography eluting with dichloromethane/methanol (100/0 to 95/5) to yield yellow oil-like product. $^1$H NMR (600 MHz, CDCl$_3$) 8.58-8.54 (m, 2H), 8.01 (d, J=8.0 Hz, 1H), 7.77 (td, J=7.8, 1.6 Hz, 1H), 7.70 (s, 1H), 7.37 (dd, J=7.5, 4.9 Hz, 1H), 7.26 (s, 1H), 4.15-3.75 (m, 6H), 3.68 (t, J=4.9 Hz, 1H), 1.67 (s, 2H); $^{13}$C NMR (100 MHz, CDCl$_3$) 161.71, 148.55, 146.76, 145.23, 143.31, 137.09, 125.44, 121.80, 60.59, 60.45, 52.35, 52.08

Dihydrotetrazine Oxidation Experiments

General Considerations

UV-Vis measurements were conducted in quartz cuvettes using either a Hewlett Packard 8453 or 8452A spectrophotometer equipped with temperature controlled, stirring cuvette holders. Glassware was cleaned by rinsing twice with phosphate buffered saline (PBS, pH=7.4) containing EDTA (2 mM) followed by triple rinsing with PBS buffer free of EDTA. PBS buffer was prepared by adding the following to Milli-Q purified water: NaCl (8 g/L), KCl (0.2 g/L), Na$_2$HPO$_4$ (1.42 g/L), KH$_2$PO$_4$ (0.24 g/L) and ethylenediaminetetraacetic acid disodium salt (0.672 g/L). The pH of the buffer was then adjusted to 7.4 using either 1M solutions of either HCl or NaOH.

Experiments to study the catalytic photooxidation were conducted at 25° C. in a thermostatted UV-cell with stirring capability and a single top-mounted LED. The LED was mounted in a custom, 3-D printed housing that is displayed below. The wavelength of irradiation was varied by exchanging LED bulbs of variable dominant wavelength (DWL). The LEDs were manufactured by CREE and had the following specifications.

Photo Red (CREE XPEPHR-L1), 660 nm LED (650-670 DWL, photo red)

Green (CREE XPEGRN-L1), 528 nm LED (520-535 DWL, green)

For LEDs, the light intensity was estimated by measuring the light intensity 4 cm from the light source, which is equal to the distance from the LED to the center of the cuvette holder. To measure the intensity of light emitted by the LEDs an International Light IL1400A instrument equipped with a SEL005 sensor was used. The instrument was calibrated to the peak intensity of the LED. All measurements were conducted in a dark room.

Methylene Blue Catalyzed Photooxidation

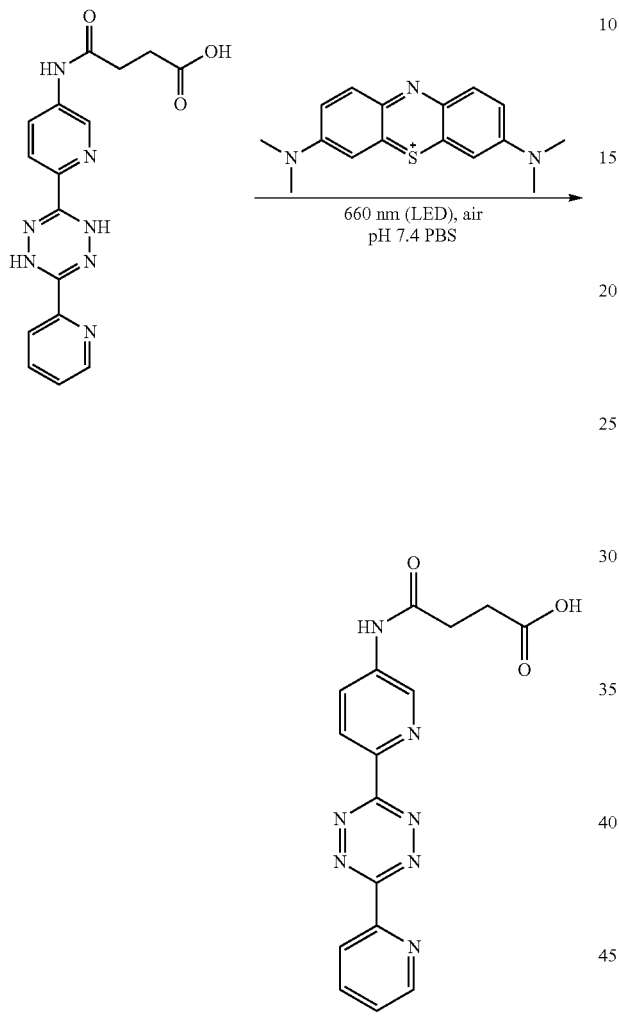

Solutions (1 mL) containing 3a (21 µM) and methylene blue (4 µM) in PBS buffer were prepared in a cuvette from stock solutions. Oxidation of 3a to 4a was monitored by recording absorbance at 325 nm every 30 seconds. Cuvettes for these experiments were washed with EDTA/PBS as described in the General Considerations (section 2.1).

Experiment 1 (continuous irradiation, FIG. 3B, main manuscript): In a cuvette, a solution of methylene blue (4 µM) and 3a (21 µM) was irradiated continuously with red light (660 nm, 9.1 mW/cm²) from an LED until no further oxidation was observed.

Experiment 2 (Toggle experiment, FIG. 3C, main manuscript): In a cuvette, a solution of methylene blue (4 µM) and 3a (21 µM) was irradiated with LED red light (660 nm, 9.1 mW/cm²) for an interval, and the light was turned off. This pulsing was repeated twice, and then the light was left on until no further oxidation was observed.

Experiment 3 (azide quenching experiment, FIG. 3D, main manuscript): In a cuvette, a solution of methylene blue (4 µM) and 3a (21 µM) was irradiated continuously with red light (660 nm, 2.6 mW/cm²). Following 60 seconds of irradiation, solid sodium azide (3.9 mg) was directly added to the cuvette, to give a final NaN₃ concentration of 60 mM. Irradiation and monitoring of reaction progress was continued until no further oxidation was observed.

Carboxyfluorescein Catalyzed Photooxidation

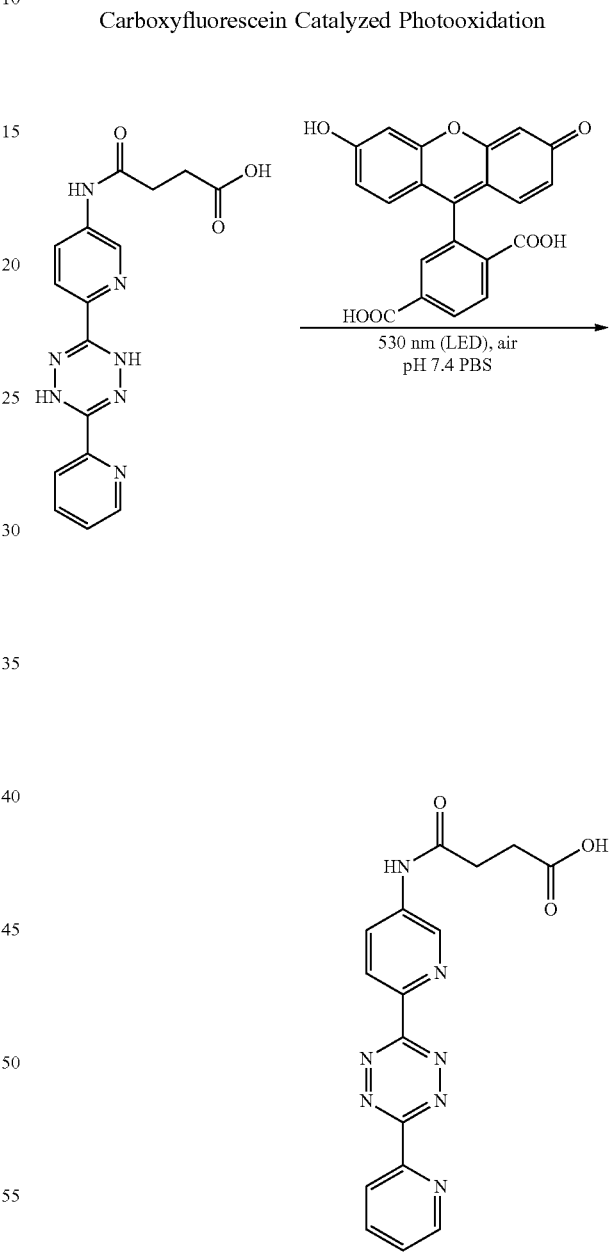

A solution (1 mL) containing 3a (19 µM) and fluorescein (7 µM) in PBS buffer with EDTA (2 mM) was prepared in a cuvette from stock solutions. Oxidation of 3a to 4a was monitored by recording absorbance at 325 nm every 10 seconds. The cuvette was irradiated with LED green light (660 nm) for an interval, and the light was turned off. This pulsing was repeated twice, and then the light was left on until no further oxidation was observed.

Rose Bengal Catalyzed Photooxidation

Horseradish Peroxidase (HRP) Oxidation

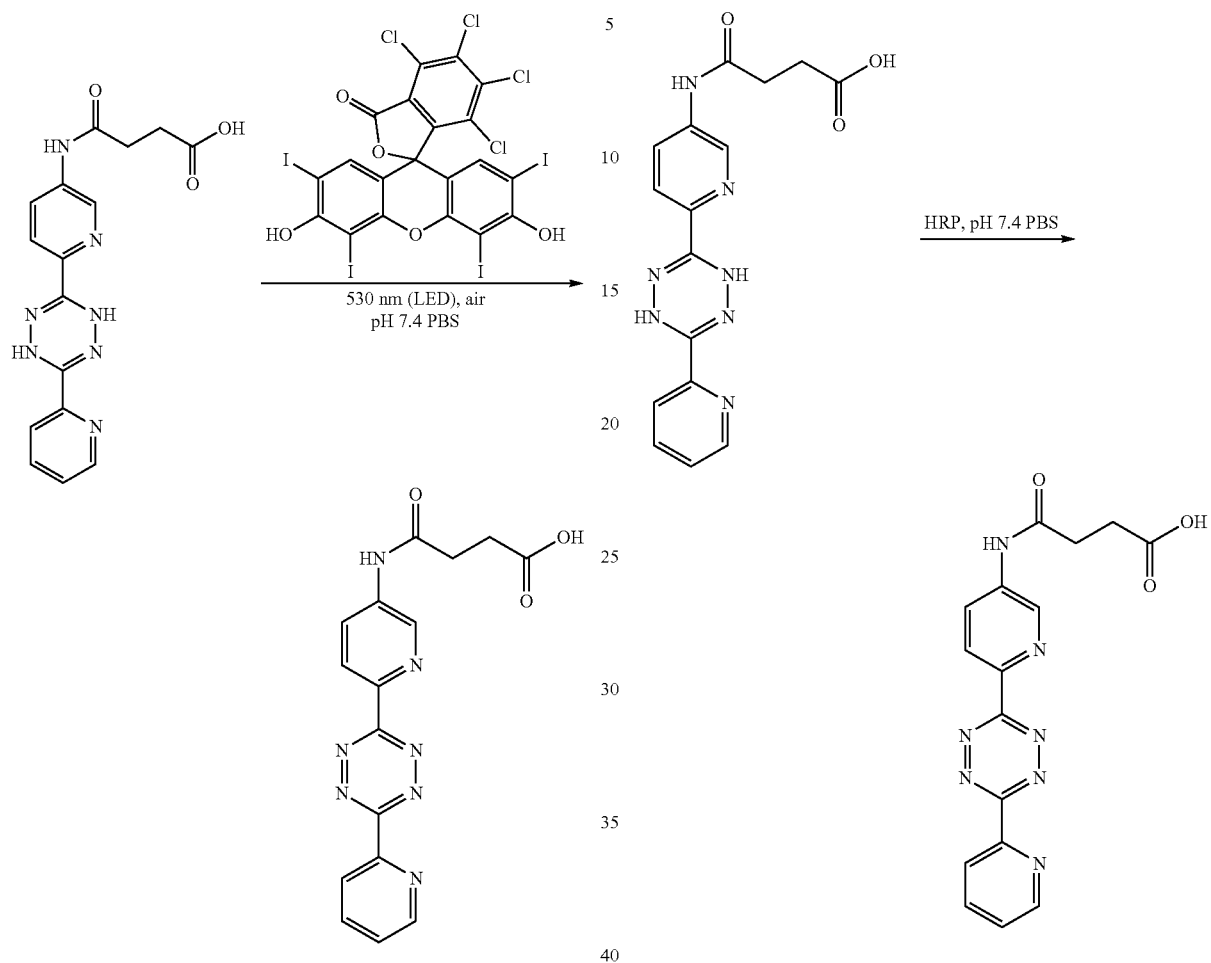

Solutions (1 mL) containing 3a and rose bengal in PBS buffer were prepared in a cuvette from stock solutions. Oxidation of 3a to 4a was monitored by recording absorbance at 325 nm every 30 seconds. Cuvettes for these experiments were washed with EDTA/PBS as described in the General Considerations (section 2.1).

Experiment 1 (continuous irradiation) In a cuvette, a solution of rose bengal (9 μM) and 3a (24 μM) was irradiated continuously with green light (528 nm, 2.2 mW/cm$^2$) from an LED until no further oxidation was observed.

Experiment 2 (Toggle experiment): In a cuvette, a solution of rose bengal (7 μM) and 3a (34 μM) was irradiated with LED green light (528 nm, 2.2 mW/cm$^2$) for an interval and the light was turned off. This pulsing was repeated twice, and then the light was left on until no further oxidation was observed.

Experiment 3 (azide quenching experiment): In a cuvette, a solution of rose bengal (2 μM) and 3a (32 μM) was irradiated continuously with LED green light (528 nm, 2.2 mW/cm$^2$). Following 60 seconds of irradiation, solid sodium azide (3.9 mg) was directly added to the cuvette, to give a final NaN$_3$ concentration of 60 mM. Irradiation and monitoring of reaction progress was continued until no further oxidation was observed.

Solutions (1 mL) containing 3a (30 μm) in PBS buffer were prepared in a cuvette from stock solutions. Oxidation of 3a to 4a was monitored by recording absorbance at 325 nm every 10 seconds while either hydrogen peroxide (2 mM), HRP (15 nM) or both were added (FIG. 4, panel B). For the superoxide dismutase experiment, HRP (15 nM) was added followed by SOD (770 nM) 40 seconds later (FIG. 4, panel C). For the kinetics experiments, solutions (1 mL) containing 3a in PBS buffer with EDTA (2 mM) were prepared in the following concentrations of 3a: 9, 17, 34, 50, 83, 150 and 200 μM. The oxidation rate was determined by observing the conversion of 3a to 4a in the first 10 seconds after mixing in HRP (15 nM) and subtracting the background oxidation prior to the addition of HRP. Kinetic parameters were determined using GraphPad's Prism 6 software from the rate data presented in Table 1.

TABLE 1

| Rate of HRP Oxidation of 3a | |
|---|---|
| [3a] (μM) | Rate × 10$^{-7}$ (M/sec) |
| 8 | 0.34 (+/− 0.04) (3 runs) |
| 17 | 0.56 (+/− 0.04) (3 runs) |
| 34 | 0.89 (+/− 0.04) (3 runs) |
| 50 | 1.2 (+/− 0.2) (3 runs) |

TABLE 1-continued

Rate of HRP Oxidation of 3a

| [3a] (μM) | Rate × $10^{-7}$ (M/sec) |
|---|---|
| 83 | 2.1 (+/− 0.1) (3 runs) |
| 150 | 2.5 (+/− 0.8) (6 runs) |
| 200 | 2.6 (+/− 0.4) (3 runs) |

Dihydrotetrazine Oxidative Stability

A solution (3 mL) containing 3a (35 μM) in PBS buffer was prepared in a cuvette from stock solutions. Oxidation was monitored by recording solution absorbance at 0, 30 and 150 minutes. The cuvette was stored in the dark between measurements.

Comparison of HRP, cytochrome C and hemoglobin: Solutions (1 mL) of 3a (30 μM) in PBS buffer were prepared in a cuvette from stock solutions. To the solutions, either hemoglobin (6.0 μM in protein, 1.5 μM in heme) or cytochrome C (9 μM) were added and while oxidation was monitored every 30 seconds by measuring absorbance at 325 nm.

Tetrazine Hydrolytic Stability

Solutions (1 mL) containing 4a (800 μM) in PBS buffer were prepared in cuvettes from stock solutions. Tetrazine concentration was measured by recording the absorbance at 525 nm every 20 minutes while holding the cuvette at either 25 for 24 hours. In PBS buffer at 25° C., tetrazine 4a (800 μM) shows 98% and 83% fidelity after 2 hours and 24 hours.

Azide $^1O_2$ Quenching Control Experiment with 1,3-Diphenylisobenzofuran

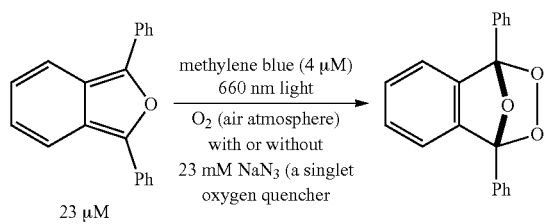

This experiment provides evidence that photolysis of 4 μM methylene blue solution generates singlet oxygen, and that $NaN_3$ (23 mM or higher) is an effective quencher of singlet oxygen under these conditions.

A solution (1 mL) containing 1,3-diphenylisobenzofuran (23 μM) and methylene blue (4 μM) in methanol was prepared in a cuvette from stock solutions. Consumption of 1,3-diphenylisobenzofuran was monitored by recording the solution absorbance at 410 nm every 10 seconds while the cuvette was continuously irradiated with red light (centered at 660 nm, 9.1 mW/cm$^2$) from an LED until completion. In a second, similarly prepared cuvette, sodium azide (23 mM) was added before irradiating with light. The reaction without $NaN_3$ was approximately 180% faster than the reaction with $NaN_3$.

Electrochemical Measurements

All electrochemistry was performed using a CHI-620D potentiostat/galvanostat. Cyclic voltammetry was performed using a standard three-electrode configuration. CV scans were recorded for quiescent solutions using a platinum disk working electrode (2.0 mm diameter CH Instruments) and a platinum wire auxiliary electrode. All potentials were measured against a Ag/AgCl reference electrode (CH Instruments, 1 M KCl). CV and DPV experiments were performed in a nitrogen saturated 0.1 M potassium phosphate ($KH_2PO_4$) buffered solution at pH 7.0. The concentration of the analyte was 1.0 mM for all experiments.

Spectroelectrochemical Measurements

Controlled potential electrolysis of the analyte was carried out using a CHI-620D potentiostat/galvanostat and a standard three-electrode configuration using a platinum mesh working electrode, a platinum wire auxiliary electrode and a 1M KCl, Ag/AgCl reference electrode. The experiment was performed in a 0.1 cm quartz spectroelectrochemical cell with nitrogen saturated 0.1 M potassium phosphate ($KH_2PO_4$) buffered solution at pH 7. The concentration of the analyte was 1.0 mM. Absorbance spectra were acquired on a StellarNet CCD array UV-vis spectrometer and acquired every 5 seconds for the duration of the experiment.

DHTz-Enriched Microfiber Fabrication Experiments

Preparation of DHTz-Microfibers

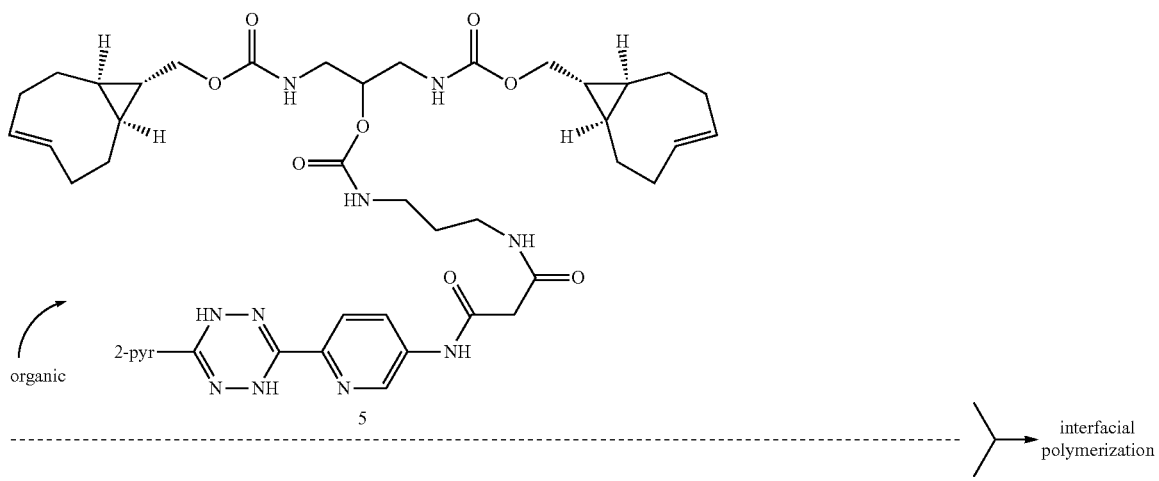

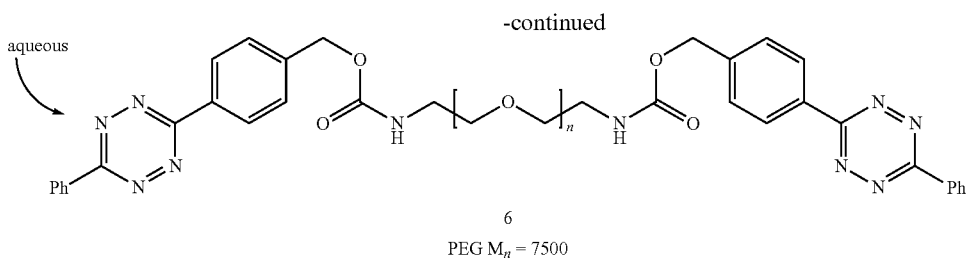

6
PEG M$_n$ = 7500

Interfacial polymerization was conducted in accord with the inventors' previously described procedure, described in S. Liu, H. Zhang, R. A. Remy, F. Deng, M. E. Mackay, J. M. Fox, X. Jia, *Adv. Mater.* 2015, 27, 2783-90. The DHTz-containing bis-sTCO monomer (5) was dissolved in ethyl acetate at a concentration of 1.2 mM. The known PEG-based bis-tetrazine monomer 6 (prepared as described in S. Liu, H. Zhang, R. A. Remy, F. Deng, M. E. Mackay, J. M. Fox, X. Jia, *Adv. Mater.* 2015, 27, 2783-90) was dissolved in water at a concentration of 0.15 mM. To a 60-mm diameter petri dish was added 3 mL of the aqueous solution of the bis-tetrazine monomer 6. The solution of 5 (3 mL) in ethyl acetate was carefully added over the aqueous phase without disturbing the interface. Upon contact, a polymer thin film formed at the interface. The thin film was grasped gently using sharp tweezers and the fiber that was pulled from the interface was connected to a collecting frame that was constructed of copper wire. The fiber was collected by manually rotating the frame. The microfibers were dried affixed onto precleaned glass slides using adhesive silicon isolators (Purchased from Grace Bio-Labs, product #665301).

To 'cap' any unreacted tetrazine end groups from the monomer 6, the fibers were treated with the water soluble sTCO derivative S5 (shown below, prepared as described in H. Zhang, K. T. Dicker, X. Xu, X. Jia, J. M. Fox, *ACS Macro Lett.* 2014, 3, 727-731). Thus, to a silicon isolator containing DHTz-enriched microfibers was added PBS solution of S5 (1 mM). The microfibers were allowed to soak in the solution for 1 minute before the capping solution was removed. The microfibers were then rinsed using PBS solution for 3 times.

S5

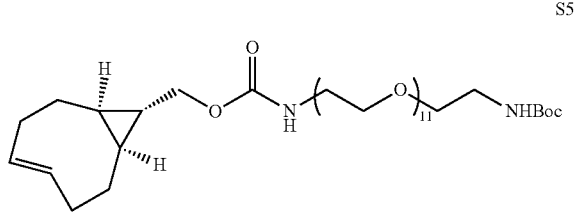

Activation and modification of the fibers was conducted inside the silicon isolators following the procedures that are outlined below. All the confocal microscope images were shot at 10× magnification unless noted otherwise.

Alexa Fluor® 647 Tagging Experiment and Control Experiments

To silicon isolator containing DHTz-functionalized microfibers was added a PBS solution of rose bengal (100 µM). The microfibers were allowed to soak in the solution for 5 minutes before rose bengal solution was removed. The microfibers were then rinsed three times with PBS buffer (~200×3 µL). The red microfibers were then immersed in PBS solution and irradiated with a 200-watt incandescent lamp for 5 minutes followed by rinsing with three portions of PBS buffer (~200×3 µL, prepared as described in S. Liu, H. Zhang, R. A. Remy, F. Deng, M. E. Mackay, J. M. Fox, X. Jia, *Adv. Mater.* 2015, 27, 2783-90). The microfibers were then treated with a PBS solution of Alexa-sTCO (1 µM) for 1 minute followed by rinsing with three portions of PBS buffer (~200×3 µL). Samples were imaged with a Zeiss LSM 5 Live DuoScan high-speed confocal microscope (Carl Zeiss, Maple Grove, Minn.).

Control without light: The procedure was identical to that described above, except that the fibers were prepared in a dark room without exposure to light.

Control without sensitizer: The microfibers were immersed in PBS buffer and irradiated with a 200-watt incandescent lamp for 5 minutes and subsequently rinsed three times with PBS buffer (~200×3 µL). The microfibers were then treated with a PBS solution of Alexa-sTCO (1 µM) for 1 minute followed by three rinses with PBS buffer (~200×3 µL). Samples were imaged with a Zeiss LSM 5 Live DuoScan high speed confocal microscope (Carl Zeiss, Maple Grove, Minn.).

Clover Protein Tagging Experiment and Control Experiment

In a silicon isolator, DHTz-functionalized microfibers were immersed in a PBS solution of methylene blue (100 µM) and irradiated with a 200-watt incandescent lamp for 5 minutes. The microfibers were then rinsed with three portions of PBS buffer (~200×3 µL) and treated with a PBS solution of Clover-sTCO (5 µM) for 1 minute followed by rinsing with three portions of PBS buffer (200×3 µL). Samples were imaged with a Zeiss LSM 5 Live DuoScan high-speed confocal microscope (Carl Zeiss, Maple Grove, Minn.)

Control without sensitizer: The microfibers were immersed in PBS solution and irradiated with a 200-watt incandescent lamp for 5 minutes followed by rinsing with three portions of PBS buffer (~200×3 µL). The microfibers were then treated by PBS solution of Clover-sTCO (5 µM) for 1 minute followed by rinsing with three portions of PBS buffer (200×3 µL). Samples were imaged with a Zeiss LSM 5 Live DuoScan high-speed confocal microscope (Carl Zeiss, Maple Grove, Minn.).

Oxidation of DHTz-Microfibers by Horseradish Peroxidase (HRP)

To silicon isolator containing DHTz-microfibers was added a PBS solution of HRP (10 µM). After the microfibers had been immersed in the solution for 1 hour, they were rinsed with three portions of PBS buffer (~200×3 µL). The microfibers were then treated with a PBS solution of Alexa-sTCO (1 µM) for 1 minute followed by rinsing with three portions of PBS buffer (~200×3 µL). Samples were imaged with a Zeiss LSM 5 Live DuoScan high-speed confocal microscope (Carl Zeiss, Maple Grove, Minn.).

Control without HRP: The microfibers were submerged in PBS solution for 1 hour followed by PBS solution rinsing for 3 times. The microfibers were then treated by PBS solution of Alexa-sTCO (1 µM) for 1 minute followed by rinsing with three portions of PBS buffer (~200×3 µL). Samples were imaged with a Zeiss LSM 5 Live DuoScan high-speed confocal microscope (Carl Zeiss, Maple Grove, Minn.).

RGD Peptide Tagging Experiment and Control Experiments

DHTz-microfibers were affixed to a silicone well (9 mm diameter) supported on a poly(2-hydroxyethyl methacrylate) (pHEMA)-coated 1-well Nunc® chamber using silicone isolators (Grace Bio-Labs, product #665301). The fibers were immersed in a solution of methylene blue (100 µM) in PBS, and then irradiated with a 200-watt incandescent lamp for 5 minutes followed by rinsing with three portions of PBS buffer (~200×3 µL). The microfibers were then immersed in a PBS solution of RGD-sTCO (10 µM) for 1 min followed by rinsing with three portions of PBS buffer (~200×3 µL).

Control without sensitizer: In a silicone well, the DHTz-microfibers were immersed in PBS buffer and irradiated with a 200-watt incandescent lamp for 5 minutes followed by rinsing with three portions of PBS buffer (~200×3 µL). The microfibers were then immersed in a PBS solution of RGD-sTCO (10 µM) for 1 min followed by rinsing with three portions of PBS buffer (~200×3 µL).

Control without RGD: The DHTz-microfibers were immersed in a solution of methylene blue (100 µm) in PBS, and irradiated with a 200-watt incandescent lamp for 5 minutes followed by rinsing with three portions of PBS buffer (~200×3 µL).

Control without RGD or sensitizer: The DHTz-microfibers were immersed in PBS and irradiated with a 200-watt incandescent lamp for 5 minutes followed by rinsing with three portions of PBS buffer (~200×3 µL).

Cell Culture and Confocal Imaging

Fibroblasts (NIH 3T3, ATCC, Manassas, Va.) were maintained in DMEM media supplemented with 10% fetal bovine serum (FBS) and 1% Pen-Strep (Invitrogen, Carlsbad, Calif.). DHTz-microfibers were affixed to a silicone well (9 mm diameter) supported on a poly(2-hydroxyethyl methacrylate) (pHEMA)-coated 1-well Nunc® chamber using silicone isolators (Grace Bio-labs, Bend, Oreg.). The fibers were washed with sterile PBS and cell culture media three times respectively before being sterilized under UV for 15 minutes. A 200 µL suspension of cells with a density of $0.5 \times 10^6$ cells/mL was added into each well and cultured at 37° C. for 20 hours before confocal imaging under transmitted light. Samples were imaged with a Zeiss LSM 5 Live DuoScan high-speed confocal microscope (Carl Zeiss, Maple Grove, Minn.).

Fe-Porphyrin Catalyzed Oxidation

Fe(III)tetrakis (1-methyl-4-pyridyl) porphyrin pentachlorideporphyrin pentachloride (Fe-TMPyP) Catalyzed Oxidation

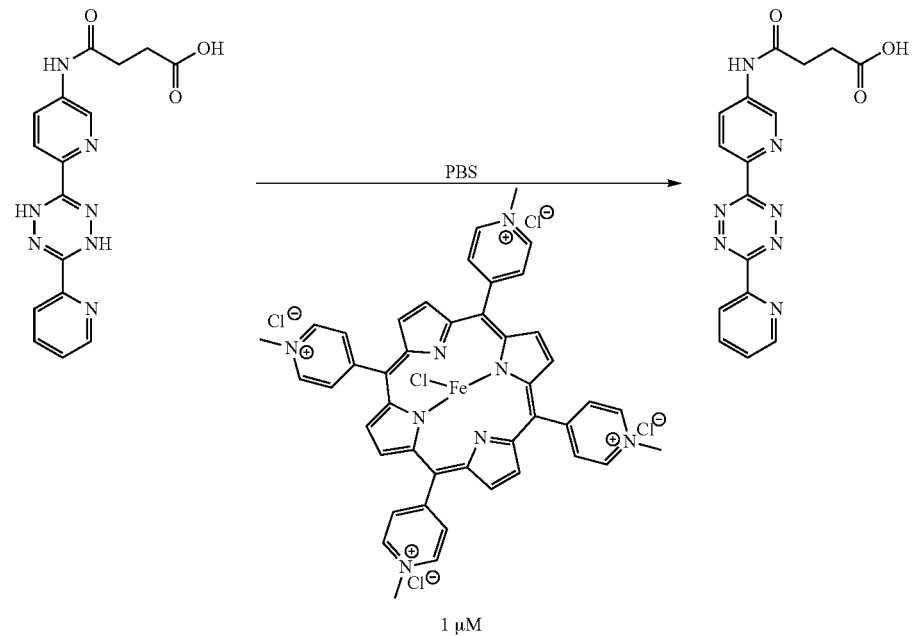

4-Oxo-4-((6-(6-(pyridin-2-yl)-1,4-dihydro-1,2,4,5-tetrazin-3-yl)pyridin-3-yl) amino)butanoic acid (35 uM in PBS (pH 7.4), 2 mL) was placed in a 1 cm×1 cm cuvette with a strongly stirred magnetic stir bar in an atmosphere of air. A solution of Fe-TMPyP (50 uM in PBS (pH 7.4), 20 uL) was added to the cuvette. The reaction was monitored by a UV-Vis spectrometer at 280 nm and 325 nm. The spectra result showed the reaction went to 50% completion within 1 minute and went to 95% completion within 5 minutes.

Fe(III)5,10,15,20-tetrakis(4-sulfonatophenyl)porphyrinato chloride (Fe TPPS) Catalyzed Oxidation

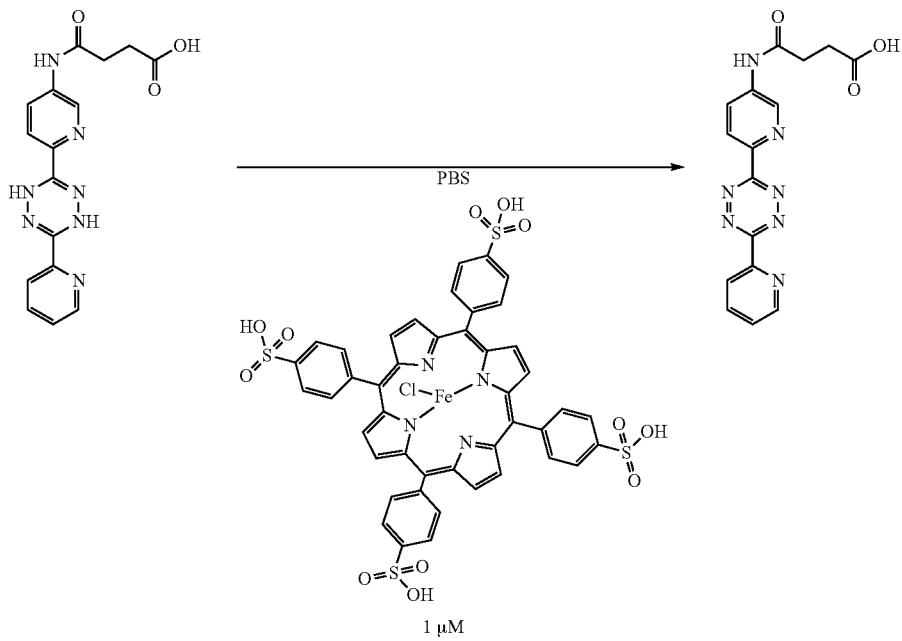

4-Oxo-4-((6-(6-(pyridin-2-yl)-1,4-dihydro-1,2,4,5-tetrazin-3-yl)pyridin-3-yl) amino)butanoic acid (35 uM in PBS (pH 7.4), 2 mL) was placed in a 1 cm×1 cm cuvette with a strongly stirred magnetic stir bar in an atmosphere of air. A solution of Fe-TPPS (50 uM in PBS (pH 7.4), 20 uL) was added to the cuvette. The reaction was monitored by a UV-Vis spectrometer at 280 nm and 325 nm. The spectra result showed the reaction went to 50% completion within 5 minutes.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A method for catalytically converting a dihydrotetrazine 1 into a tetrazine 2, wherein one R group on the dihydrotetrazine 1 is a substituted or unsubstituted aryl, heteroaryl, alkyl, alkenyl, alkynyl, carbonyl, or heteroatom-containing group, and the other R group is selected from the group consisting of H and substituted or unsubstituted aryl, heteroaryl, alkyl, alkenyl, alkynyl, carbonyl, or heteroatom-containing groups;

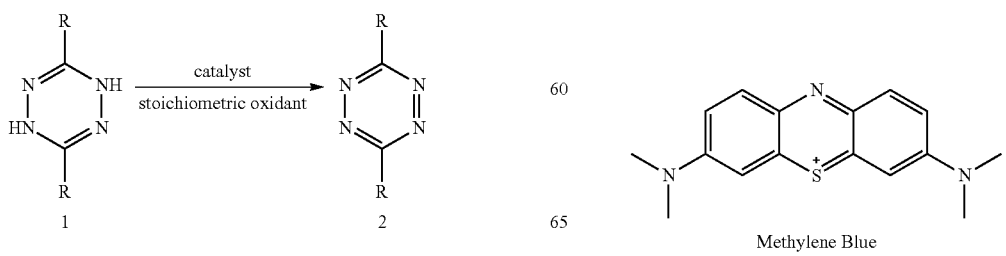

wherein the method comprises oxidizing dihydrotetrazine 1 in a reaction medium in the presence of a catalyst and a stoichiometric oxidant, and wherein the catalyst is a photocatalyst and light is utilized to activate the catalyst.

2. The method according to claim 1, wherein the photocatalyst is one of the following compounds or a derivative thereof:

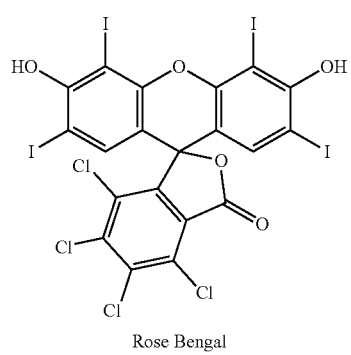

Rose Bengal

Methylene Blue

-continued
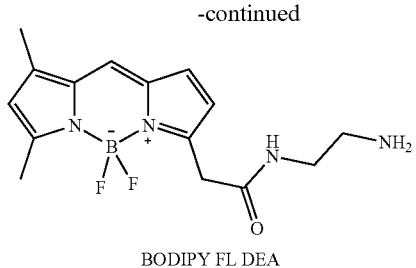
BODIPY FL DEA
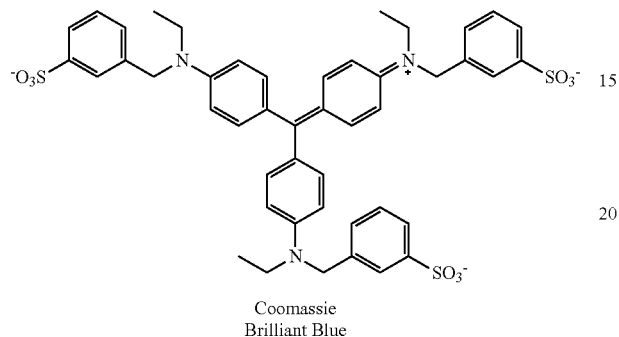
Coomassie Brilliant Blue
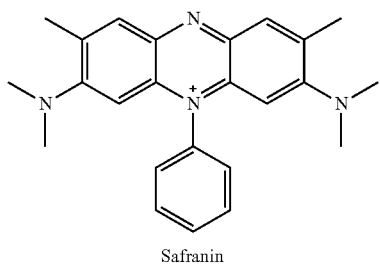
Safranin
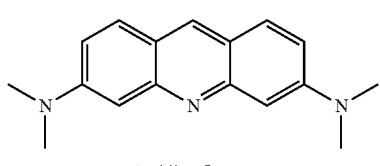
Acridine Orange
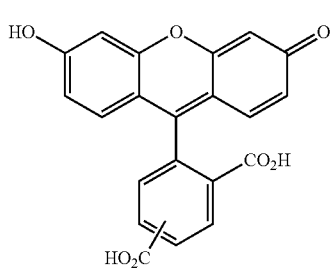
Fluoroceins
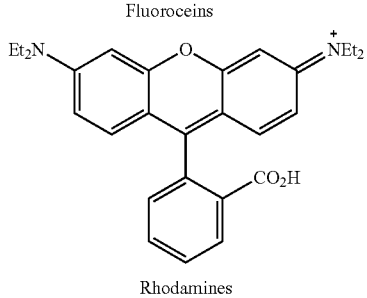
Rhodamines
-continued
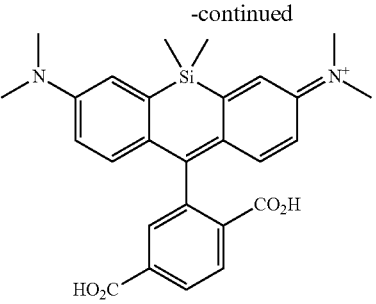
Si-Rhodamine
(purchased from spirochrome SC004-1 mg)
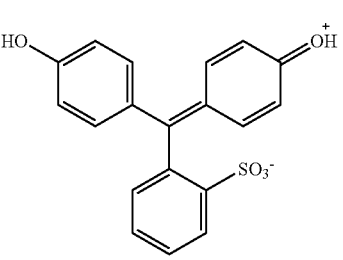
Phenot Red
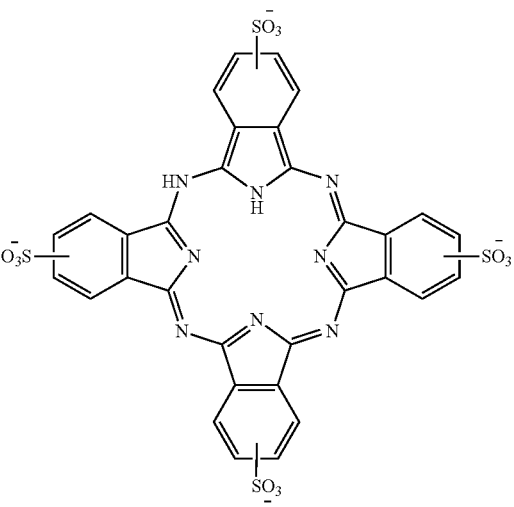
Phthalocyanine tetrasulfonate
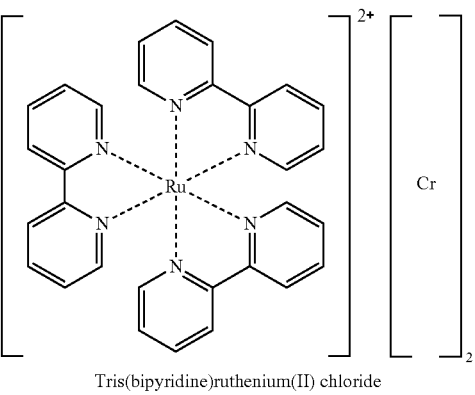
Tris(bipyridine)ruthenium(II) chloride -continued

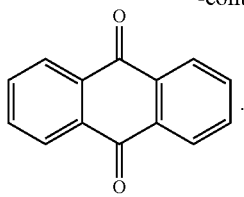

Anthraquinone

3. The method according to claim 1, wherein the stoichiometric oxidant is at least one of $O_2$, atmospheric $O_2$, hydrogen peroxide, or a disulfide.

4. The method according to claim 3, wherein the $O_2$ is at a concentration lower than that found under atmospheric conditions.

5. The method according to claim 1, wherein the dihydrotetazine 1 has one of the following structures:

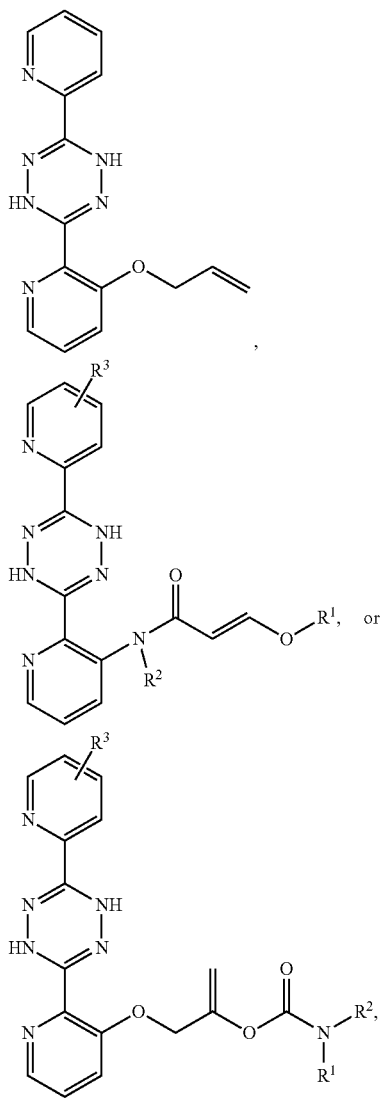

wherein $R^1$, $R^2$ and $R^3$ are each individually selected from the group consisting of H, aryl, heteroaryl, alkyl, alkenyl, alkynyl, carbonyl, and heteroatom-containing groups.

6. The method according to claim 5, wherein the dihydrotetazine 1 has one of the following structures:

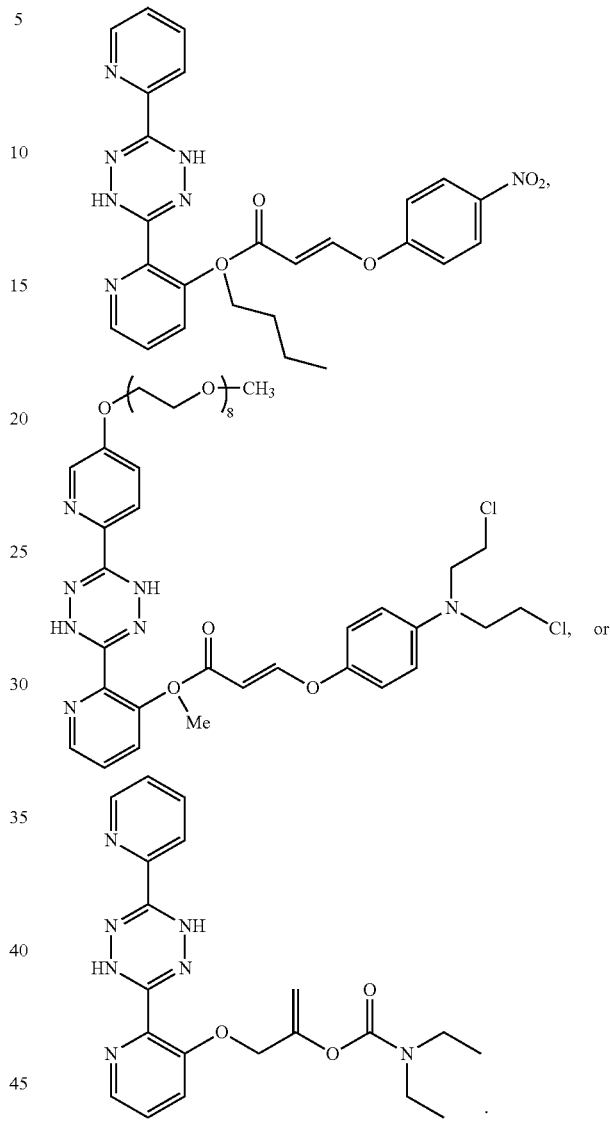

7. The method according to claim 1, wherein the dihydrotetazine 1 has the following structure:

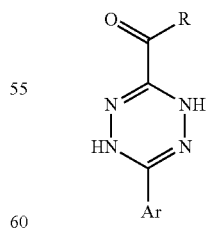

wherein R is selected from the group consisting of H, aryl, heteroaryl, alkyl, alkenyl, alkynyl, and heteroatom-containing groups, and Ar is an aromatic or heteroaromatic group.

8. The method according to claim 7, wherein the dihydrotetazine 1 has one of the following structures:

9. The method according to claim 1, wherein the tetrazine 2 has one of the following structures:
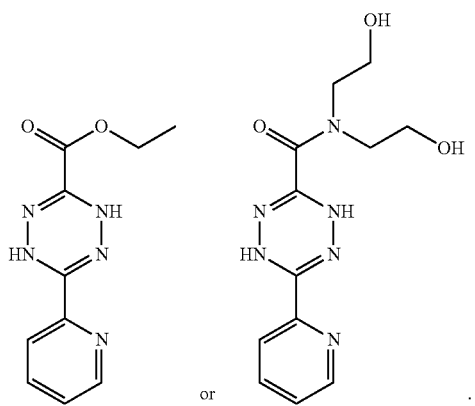 [SMILES: CCOC(=O)C1=NNC(c2ccccn2)=NN1 ; O=C(C1=NNC(c2ccccn2)=NN1)N(CCO)CCO] or 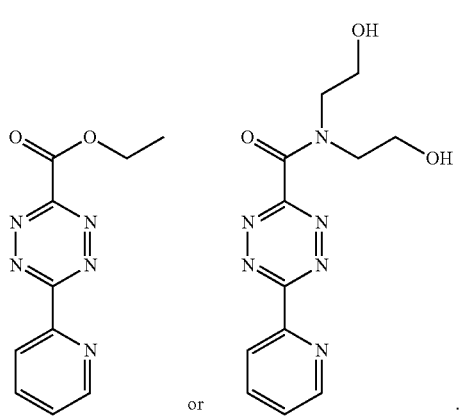 [SMILES: CCOC(=O)c1nnc(-c2ccccn2)nn1 ; O=C(c1nnc(-c2ccccn2)nn1)N(CCO)CCO] .
* * * * *

UNITED STATES PATENT AND TRADEMARK OFFICE
CERTIFICATE OF CORRECTION

Page 1 of 2

PATENT NO. : 10,875,840 B2
APPLICATION NO. : 16/062423
DATED : December 29, 2020
INVENTOR(S) : Joseph Fox et al.

It is certified that error appears in the above-identified patent and that said Letters Patent is hereby corrected as shown below:

On the Title Page

Item (57), In Abstract, Scheme [I], as shown below:

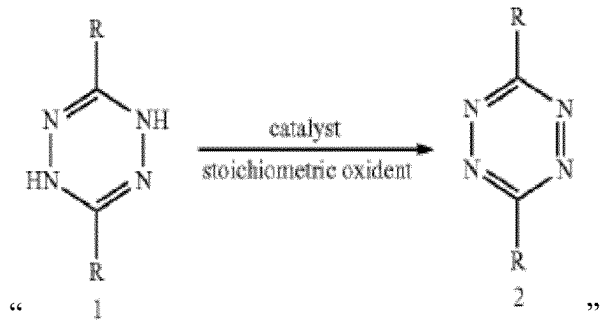

"

Should read as follows:

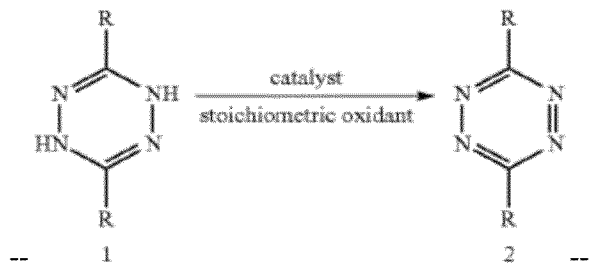

--

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,875,840 B2

In the Claims

In Claim 6, Lines 19-33, the chemical structure, as shown below:

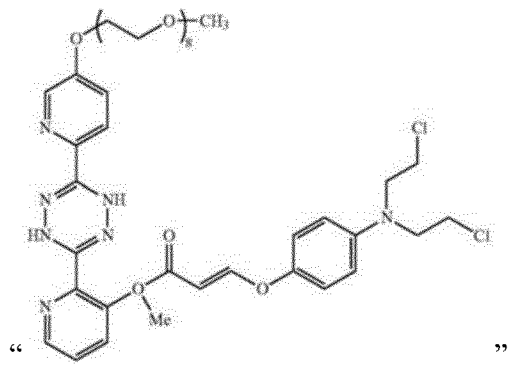

"                                        "

Should read as follows:

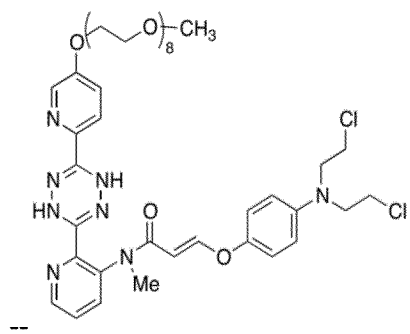

--                              --